(12) United States Patent
Liotta et al.

(10) Patent No.: US 7,524,964 B2
(45) Date of Patent: Apr. 28, 2009

(54) TETRAHYDROTHIOPYRANO PYRAZOLE CANNABINOID MODULATORS

(75) Inventors: Fina Liotta, Westfield, NJ (US); Huajun Lu, Bridgewater, NJ (US); Mingde Xia, Belle Mead, NJ (US); Michael P. Wachter, Bloomsbury, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 11/952,375

(22) Filed: Dec. 7, 2007

(65) Prior Publication Data

US 2008/0085899 A1 Apr. 10, 2008

Related U.S. Application Data

(63) Continuation of application No. 11/376,844, filed on Mar. 16, 2006, now abandoned.

(60) Provisional application No. 60/666,898, filed on Mar. 31, 2005.

(51) Int. Cl.
*C07D 211/32* (2006.01)
*C07D 231/54* (2006.01)

(52) U.S. Cl. .................... 546/199; 548/360.5
(58) Field of Classification Search .............. 546/199; 548/360.5
See application file for complete search history.

(56) References Cited

FOREIGN PATENT DOCUMENTS

| WO | WO 01/32663 | 5/2001 |
|---|---|---|
| WO | WO 2004/094421 | 11/2004 |

OTHER PUBLICATIONS

Masferrer et al. (CAPLUS abstract of US 20030220376).*
Tanaka et al. (CAPLUS abstract of WO 9732848).*
Rovnyak, George C. et al., "Synthesis and antinflammatory activity of hexahydrothiopyrano[4,3- c]pyrazoles and related analogs", ournal of Medicinal Chemistry, vol. 25, No. 12, pp. 1482-1488, Coden: JMCMAR.

* cited by examiner

*Primary Examiner*—Kamal A Saeed
*Assistant Examiner*—Robert Havlin
(74) *Attorney, Agent, or Firm*—Thomas Dodd

(57) ABSTRACT

The invention relates to a CB modulator compound of Formula (I)

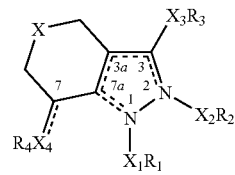

or a pharmaceutically acceptable form thereof and a method for use in treating, ameliorating or preventing a CB receptor mediated syndrome, disorder or disease.

14 Claims, No Drawings

TETRAHYDROTHIOPYRANO PYRAZOLE CANNABINOID MODULATORS

CROSS-REFERENCE TO RELATED APPLICATIONS

This application is a Continuation of application Ser. No. 11/376,844, filed Mar. 16, 2006 now abandoned.

This present application claims benefit of U.S. Provisional Patent Application Ser. No. 60/666,898, filed Mar. 31, 2005, which is incorporated herein by reference in its entirety and for all purposes.

BACKGROUND OF THE INVENTION

Before the discovery of the cannabinoid CB1 and CB2 receptors, the term cannabinoid (CB) was used to describe the biologically active components of *cannabis sativa*, the most abundant of which are delta-9-tetrahydrocannabinol (THC) and cannabidiol.

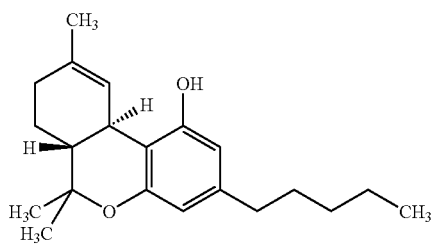

THC

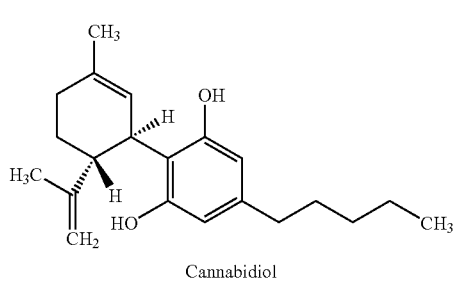

Cannabidiol

THC is a moderately potent partial agonist of the CB1 and CB2 receptors and is considered the "classical cannabinoid," a term now used to refer to other analogues and derivatives that are structurally related to the tricyclic dibenzopyran THC core. The term "non-classical cannabinoid" refers to CB agonists structurally related to cannabidiol.

Pharmacological investigations have concentrated on selective CB receptor modulators of the pyrazole structural class, which include SR 141716A (the monohydrochloride salt of SR 141716) and SR 144528. SR 141716A was the first potent and selective CB1 receptor antagonist.

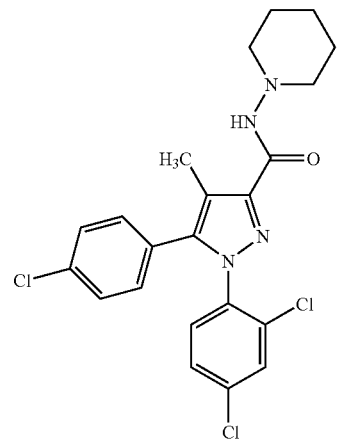

SR 141716

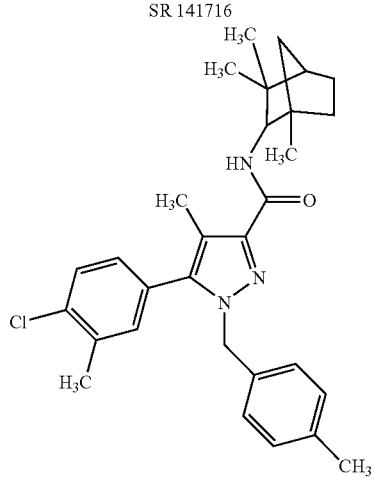

SR 144528

Pyrazole CB modulators are among the many different structural classes which have aided the development of CB pharmacology, have helped to determine the biological effects mediated by the CB receptors, will lead to further refinement of current compounds, and will be a source of new chemical classes in the future.

Certain compounds (including SR 141716, SR 144528 and the like) that were originally classified as selective antagonists are now considered to act as "inverse agonists" rather than pure antagonists. Inverse agonists have the ability to decrease the constitutive level of receptor activation in the absence of an agonist instead of only blocking the activation induced by agonist binding at the receptor. The constitutive activity of CB receptors has important implications since there is a level of continuous signaling by CB1 even in the absence of an agonist. For example, SR 141716A increases CB1 protein levels and sensitizes cells toward agonist action, thus indicating that inverse agonists may be another class of ligands used to modulate the endocannabinoid system and the downstream signaling pathways activated by cannabinoid receptors.

Advances in the synthesis of CB and cannabimimetic ligands have furthered the development of receptor pharmacology and provided evidence for the existence of additional CB receptor sub-types. However, there remains an ongoing need for the identification and development of small molecule CB1 or CB2 receptor modulators for the treatment of a variety of CB receptor modulated syndromes, disorders, and diseases.

All documents cited herein are incorporated by reference.

SUMMARY OF THE INVENTION

This invention is directed to tetrahydrothiopyrano pyrazole CB modulator compounds and a method for use in treating, ameliorating or preventing a CB receptor mediated syndrome, disorder or disease.

The invention relates to a CB modulator compound of Formula (I)

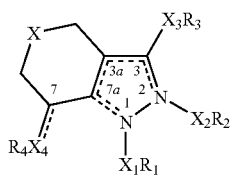

or a pharmaceutically acceptable form thereof and a method for use in treating, ameliorating or preventing a CB receptor mediated syndrome, disorder or disease.

DESCRIPTION OF THE INVENTION

This invention is directed to a compound of Formula (I):

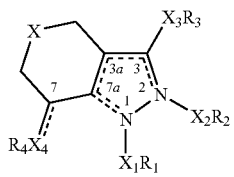

wherein the dashed lines between positions 2-3 and positions 3a-7a in Formula (I) each represent the location for a double bond when $X_1R_1$ is present;

the dashed lines between positions 3-3a and positions 7a-1 in Formula (I) each represent the location for a double bond when $X_2R_2$ is present;

the dashed line between position 7 and $X_4R_4$ in Formula (I) represents the location for a double bond;

X is sulfur, sulfoxo or sulfonyl;

$X_1$ is absent or is lower alkylene;

$X_2$ is absent or is lower alkylene;

wherein only one of $X_1R_1$ and $X_2R_2$ are present;

$X_3$ is absent or is lower alkylene or lower alkylidene;

when the dashed line between position 7 and $X_4R_4$ is absent, then $X_4$ is absent or is lower alkylene;

when the dashed line between position 7 and $X_4R_4$ is present, then $X_4$ is absent;

$R_1$ is hydrogen, aryl, $C_3$-$C_{12}$ cycloalkyl, or heterocyclyl, wherein each of aryl, $C_3$-$C_{12}$ cycloalkyl, or heterocyclyl is optionally substituted at one or more positions by halogen, lower alkyl, hydroxy or lower alkoxy;

$R_2$ is hydrogen, aryl, $C_3$-$C_{12}$ cycloalkyl, or heterocyclyl, wherein each of aryl, $C_3$-$C_{12}$ cycloalkyl, or heterocyclyl is optionally substituted at one or more positions by halogen, lower alkyl, hydroxy or lower alkoxy;

$R_3$ is —C(O)-heterocyclyl or -Z-N($R_6$)-$Z_1R_7$ (optionally substituted on heterocyclyl by one or more hydroxy, halogen, amino, lower alkyl, carboxy, alkoxycarbonyl, lower alkoxy, lower alkoxy-lower alkylene-, hydroxy-alkylene-, aryloxy or arylalkoxy);

when the dashed line between position 7 and $X_4R_4$ is absent, then $R_4$ is hydrogen, hydroxy, lower alkyl, lower alkoxy, halogen, aryl (optionally substituted on aryl at one or more positions by hydroxy, lower alkyl, lower alkoxy or halogen), heterocyclyl (optionally substituted on heterocyclyl at one or more positions by hydroxy, lower alkyl, lower alkoxy or halogen) or $C_3$-$C_{12}$ cycloalkyl (optionally substituted on $C_3$-$C_{12}$ cycloalkyl at one or more positions by hydroxy, lower alkyl, lower alkoxy or halogen);

when the dashed line between position 7 and $X_4R_4$ is present, then $R_4$ is CH-aryl (optionally substituted on aryl at one or more positions by hydroxy, lower alkyl, lower alkoxy or halogen) or CH-heterocyclyl (optionally substituted on heterocyclyl at one or more positions by hydroxy, lower alkyl, lower alkoxy or halogen);

$R_6$ and $R_7$ are each individually hydrogen, lower alkyl, —$NR_8R_9$, aryl (optionally substituted on aryl by one or more hydroxy, halogen, lower alkyl, carboxy, alkoxycarbonyl, lower alkoxy, hydroxy-alkylene-, aryloxy or arylalkoxy), $C_3$-$C_{12}$ cycloalkyl (optionally substituted on $C_3$-$C_{12}$ cycloalkyl by one or more hydroxy, halogen, amino, lower alkyl, carboxy, alkoxycarbonyl, lower alkoxy, hydroxy-alkylene-, aryloxy, arylalkoxy or lower alkylene) or heterocyclyl (optionally substituted on heterocyclyl by one or more hydroxy, halogen, amino, lower alkyl, carboxy, alkoxycarbonyl, lower alkoxy, lower alkoxy-lower alkylene-, hydroxy-alkylene-, aryloxy or arylalkoxy);

$R_8$ and $R_9$ are each individually hydrogen, alkyl, heterocyclyl, $C_3$-$C_{12}$ cycloalkyl, or aryl (optionally substituted on aryl by one or more lower alkyl, hydroxy, alkoxy, halogen, heterocyclyl or aryl-lower alkylene-);

Z is carbonyl or sulfonyl;

$Z_1$ is absent or is lower alkylene optionally substituted at one or more positions by halogen, hydroxy, lower alkoxy, carboxy or lower alkoxycarbonyl;

or a pharmaceutically acceptable salt, isomer, prodrug, metabolite or polymorph thereof.

An example of the present invention is a compound of Formula (I) wherein $X_1$ is absent or is lower alkylene and $R_1$ is hydrogen, $C_3$-$C_{12}$ cycloalkyl or aryl (optionally substituted on aryl at one or more positions by lower alkyl, lower alkoxy or halogen).

An example of the present invention is a compound of Formula (I) wherein when the dashed line between position 7 and $X_4R_4$ is absent, then $X_4$ is absent or is lower alkylene and $R_4$ is hydrogen, hydroxy, lower alkyl, lower alkoxy, halogen, aryl (optionally substituted on aryl at one or more positions by lower alkoxy or halogen), heterocyclyl (optionally substituted on heterocyclyl at one or more positions by halogen) or $C_3$-$C_8$ cycloalkyl.

An example of the present invention is a compound of Formula (I) wherein when the dashed line between positions 7 and $X_4R_4$ is absent, then $X_4$ is absent and $R_4$ is hydrogen.

An example of the present invention is a compound of Formula (I) wherein $X_3$ is absent or is lower alkylidene; $R_3$ is —C(O)-heterocyclyl or -Z-N($R_6$)-$Z_1R_7$ (optionally substituted on heterocyclyl by one or more hydroxy, halogen, amino, lower alkyl, carboxy, alkoxycarbonyl, lower alkoxy, lower alkoxy-lower alkylene-, hydroxy-alkylene-, aryloxy or arylalkoxy); Z is carbonyl or sulfonyl; $Z_1$ is absent or is lower alkylene; and $R_6$ and $R_7$ are each individually hydrogen, lower alkyl, —$NR_8R_9$, aryl (optionally substituted on aryl by one or more hydroxy, halogen, lower alkyl, carboxy, alkoxycarbonyl, lower alkoxy, hydroxy-alkylene-, aryloxy or arylalkoxy), $C_3$-$C_{12}$ cycloalkyl (optionally substituted on $C_3$-$C_{12}$ cycloalkyl by one or more hydroxy, halogen, amino, lower alkyl, carboxy, alkoxycarbonyl, lower alkoxy, hydroxy-alkylene-, aryloxy, arylalkoxy or lower alkylene) or heterocyclyl (optionally substituted on heterocyclyl by one or more hydroxy, halogen, amino, lower alkyl, carboxy, alkoxycarbonyl, lower alkoxy, lower alkoxy-lower alkylene-, hydroxy-alkylene-, aryloxy or arylalkoxy), wherein $R_8$ and $R_9$ are each individually hydrogen, alkyl, heterocyclyl, $C_3$-$C_{12}$ cycloalkyl or aryl (optionally substituted on aryl by one or more lower alkyl, hydroxy, alkoxy, halogen, heterocyclyl or aryl-lower alkylene-).

An example of the present invention is a compound of Formula (I) wherein $X_3$ is absent or is lower alkylidene; $R_3$ is —C(O)-heterocyclyl or -Z-N($R_6$)-$Z_1R_7$; Z is carbonyl or sulfonyl; $Z_1$ is absent or is lower alkylene; and $R_6$ and $R_7$ are each individually hydrogen, lower alkyl, —NR$_8$R$_9$, aryl (optionally substituted on aryl by one or more hydroxy, halogen, lower alkyl, lower alkoxy or hydroxy-alkylene-), $C_3$-$C_{12}$ cycloalkyl (optionally substituted on $C_3$-$C_{12}$ cycloalkyl by one or more hydroxy, halogen, amino, lower alkyl, carboxy, alkoxycarbonyl, lower alkoxy or hydroxy-alkylene-), or heterocyclyl (optionally substituted on heterocyclyl by one or more hydroxy, halogen, amino, lower alkyl, carboxy, alkoxycarbonyl, lower alkoxy, lower alkoxy-lower alkylene- or hydroxy-alkylene-), wherein $R_8$ and $R_9$ are each individually hydrogen, alkyl, heterocyclyl, $C_3$-$C_{12}$ cycloalkyl or aryl (optionally substituted on aryl by one or more lower alkyl, hydroxy, alkoxy or halogen).

An example of the present invention is a compound of Formula (I) wherein $X_3$ is absent or is lower alkylidene; $R_3$ is —C(O)-heterocyclyl or -Z-N($R_6$)-$Z_1R_7$; Z is carbonyl or sulfonyl; $Z_1$ is absent or is lower alkylene; and $R_6$ and $R_7$ are each individually hydrogen, lower alkyl, —NR$_8$R$_9$, aryl, $C_3$-$C_{12}$ cycloalkyl (optionally substituted on $C_3$-$C_{12}$ cycloalkyl by one or more hydroxy, lower alkyl or alkoxycarbonyl), or heterocyclyl (optionally substituted on heterocyclyl by one or more lower alkyl, alkoxycarbonyl, lower alkoxy-lower alkylene- or hydroxy-alkylene-), wherein $R_8$ and $R_9$ are each individually hydrogen, alkyl, $C_3$-$C_{12}$ cycloalkyl or aryl (optionally substituted on aryl by one or more halogen).

An example of the present invention is a compound of Formula (I) wherein $X_2$ is absent or is lower alkylene; and, $R_2$ is $C_3$-$C_{12}$ cycloalkyl or aryl (optionally substituted on aryl at one or more positions by lower alkyl, lower alkoxy or halogen).

An example of the present invention is a compound of Formula (I) wherein when the dashed line between position 7 and $X_4R_4$ is present, then $X_4$ is absent and $R_4$ is CH-aryl (optionally substituted on aryl at one or more positions by hydroxy, lower alkyl, lower alkoxy or halogen) or CH-heterocyclyl (optionally substituted on heterocyclyl at one or more positions by hydroxy, lower alkyl, lower alkoxy or halogen).

An example of the present invention is a compound of Formula (I) wherein when the dashed line between position 7 and $X_4R_4$ is present, then $X_4$ is absent and $R_4$ is CH-aryl (optionally substituted on aryl at one or more positions by lower alkyl, lower alkoxy or halogen) or CH-heterocyclyl (optionally substituted on heterocyclyl at one or more positions by lower alkyl, lower alkoxy or halogen).

An example of the present invention is a compound of Formula (I) wherein when the dashed line between position 7 and $X_4R_4$ is present, then $X_4$ is absent and $R_4$ is CH-phenyl, CH-thienyl or CH-furyl (optionally substituted on phenyl, thienyl or furyl at one or more positions by lower alkyl, lower alkoxy or halogen).

An example of the present invention is a compound of Formula (I) wherein X is sulfur, sulfoxo or sulfonyl; $X_1$ is absent or is lower alkylene; $R_1$ is hydrogen, $C_3$-$C_{12}$ cycloalkyl or aryl (optionally substituted on aryl at one or more positions by lower alkyl, lower alkoxy or halogen); when the dashed line between positions 7 and $X_4R_4$ is absent, then $X_4$ is absent and $R_4$ is hydrogen; $X_3$ is absent or is lower alkylidene; $R_3$ is —C(O)-heterocyclyl or -Z-N($R_6$)-$Z_1R_7$; Z is carbonyl or sulfonyl; $Z_1$ is absent or is lower alkylene; $R_6$ and $R_7$ are each individually hydrogen, lower alkyl, —NR$_8$R$_9$, aryl, $C_3$-$C_{12}$ cycloalkyl (optionally substituted on $C_3$-$C_{12}$ cycloalkyl by one or more hydroxy, lower alkyl or alkoxycarbonyl) or heterocyclyl (optionally substituted on heterocyclyl by one or more lower alkyl, alkoxycarbonyl, lower alkoxy-lower alkylene- or hydroxy-alkylene-), wherein $R_8$ and $R_9$ are each individually hydrogen, alkyl, $C_3$-$C_{12}$ cycloalkyl or aryl (optionally substituted on aryl by one or more halogen); $X_2$ is absent or is lower alkylene; $R_2$ is $C_3$-$C_{12}$ cycloalkyl or aryl (optionally substituted on aryl at one or more positions by lower alkyl, lower alkoxy or halogen); and, when the dashed line between position 7 and $X_4R_4$ is present, then $X_4$ is absent and $R_4$ is CH-phenyl, CH-thienyl or CH-furyl (optionally substituted on phenyl, thienyl or furyl at one or more positions by lower alkyl, lower alkoxy or halogen).

An example of the invention is a compound of Formula (Ia)

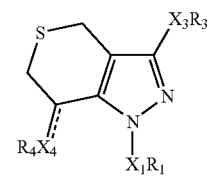

wherein $X_1R_1$, $X_3R_3$, and $X_4R_4$ are dependently selected from

| Cpd | $X_1R_1$ | $X_3R_3$ | $X_4R_4$ |
|---|---|---|---|
| 1 | $CH_2$-phenyl | C(O)NH—CH(phenyl)-R—$CH_3$ | H |
| 3 | $CH_2$-phenyl | CH=CHSO$_2$NH—CH(phenyl)-S—$CH_3$ | H |
| 7 | $CH_2$-phenyl | CH=CHSO$_2$NH—CH(phenyl)-R—$CH_3$ | H |
| 11 | $CH_2$-phenyl | CH=CHSO$_2$NH—CH(cyclohexyl)-R—$CH_3$ | H |
| 12 | $CH_2$-phenyl | CH=CHSO$_2$NH—CH(cyclohexyl)-S—$CH_3$ | H |
| 19 | $CH_2$-phenyl | C(O)NH-1,3,3-($CH_3$)$_3$-bicyclo[2.2.1]hept-2-yl | H |
| 32 | $CH_2$-phenyl | CH=CHC(O)NH—CH(phenyl)-S—$CH_3$ | H |
| 33 | $CH_2$-phenyl | CH=CHC(O)NH—CH(phenyl)-R—$CH_3$ | H |
| 38 | 2,4-$F_2$-phenyl | CH=CHSO$_2$NH—CH(phenyl)-S—$CH_3$ | $CH_2$-3-F-phenyl |
| 39 | 2,4-$F_2$-phenyl | CH=CHSO$_2$NH—CH(cyclohexyl)-R—$CH_3$ | $CH_2$-3-F-phenyl |
| 40 | 2,4-$F_2$-phenyl | CH=CHSO$_2$NH-piperidin-1-yl | $CH_2$-3-F-phenyl |

-continued

| Cpd | $X_1R_1$ | $X_3R_3$ | $X_4R_4$ |
|---|---|---|---|
| 41 | 2,4-$F_2$-phenyl | CH=CHSO$_2$NH-morpholin-4-yl | CH$_2$-3-F-phenyl |
| 46 | 2,4-Cl$_2$-phenyl | CH=CHSO$_2$NH—CH(phenyl)-S—CH$_3$ | CH$_2$-3-Cl-phenyl |
| 47 | H | CH=CHSO$_2$NH—CH(phenyl)-S—CH$_3$ | CH$_2$-3-F-phenyl |
| 48 | H | CH=CHSO$_2$NH—CH(cyclohexyl)-R—CH$_3$ | CH$_2$-3-F-phenyl |
| 52 | 2,4-Cl$_2$-phenyl | C(O)NHNH-2,4-Cl$_2$-phenyl | (Z)-CH-4-F-phenyl |
| 54 | 2,4-Cl$_2$-phenyl | C(O)NH-piperidin-1-yl | (Z)-CH-4-F-phenyl |
| 55 | 2,4-Cl$_2$-phenyl | C(O)-piperidin-1-yl | (Z)-CH-4-F-phenyl |
| 56 | 2,4-Cl$_2$-phenyl | C(O)NH-pyrrolidin-1-yl | (Z)-CH-4-F-phenyl |
| 57 | 2,4-Cl$_2$-phenyl | C(O)-pyrrolidin-1-yl | (Z)-CH-4-F-phenyl |
| 58 | 2,4-Cl$_2$-phenyl | C(O)NH-(1R-2S)-2-OH-indan-1-yl | (Z)-CH-4-F-phenyl |
| 59 | 2,4-Cl$_2$-phenyl | C(O)NH-(1S,2R)-2-OH-indan-1-yl | (Z)-CH-4-F-phenyl |
| 60 | 2,4-Cl$_2$-phenyl | C(O)NH-(1R,2R)-2-OH-cyclopentyl | (Z)-CH-4-F-phenyl |
| 61 | 2,4-Cl$_2$-phenyl | C(O)NH-(1R,2R)-2-OH-cyclohexyl | (Z)-CH-4-F-phenyl |
| 62 | 2,4-Cl$_2$-phenyl | C(O)NH-CH(phenyl)-S—CH$_3$ | (Z)-CH-4-F-phenyl |
| 63 | 2,4-Cl$_2$-phenyl | C(O)NH-CH(phenyl)-R—CH$_3$ | (Z)-CH-4-F-phenyl |
| 64 | 2,4-Cl$_2$-phenyl | C(O)NH-4-C(O)OC(CH$_3$)$_3$-piperazin-1-yl | (Z)-CH-4-F-phenyl |
| 72 | 2,4-Cl$_2$-phenyl | C(O)NHCH$_2$-pyridin-2-yl | (Z)-CH-4-F-phenyl |
| 93 | 4-Cl-phenyl | C(O)NH-piperidin-1-yl | (Z)-CH-4-F-phenyl |
| 94 | 4-Cl-phenyl | C(O)NH-CH(phenyl)-R—CH$_3$ | (Z)-CH-4-F-phenyl |
| 102 | 4-Cl-phenyl | C(O)NH-pyrrolidin-1-yl | (Z)-CH-4-F-phenyl |
| 103 | 4-Cl-phenyl | C(O)NH-hexahydro-cyclopenta[c]pyrrol-2-yl | (Z)-CH-4-F-phenyl |
| 111 | 2,4-Cl$_2$-phenyl | C(O)NH-2,6-(CH$_3$)$_2$-piperidin-1-yl | (Z)-CH-4-F-phenyl |
| 112 | 2,4-Cl$_2$-phenyl | C(O)NH-azepan-1-yl | (Z)-CH-4-F-phenyl |
| 113 | 2,4-Cl$_2$-phenyl | C(O)NH-4-CH$_3$-piperazin-1-yl | (Z)-CH-4-F-phenyl |
| 114 | 2,4-Cl$_2$-phenyl | C(O)NH-4-(CH$_2$)$_2$OH-piperazin-1-yl | (Z)-CH-4-F-phenyl |
| 115 | 2,4-Cl$_2$-phenyl | C(O)NHNH-cyclohexyl | (Z)-CH-4-F-phenyl |
| 116 | 2,4-Cl$_2$-phenyl | C(O)NH-hexahydro-cyclopenta[c]pyrrol-2-yl | (Z)-CH-4-F-phenyl |
| 122 | 2,4-Cl$_2$-phenyl | C(O)NH-(2R)-2-CH$_2$OCH$_3$-pyrrolidin-1-yl | (Z)-CH-4-F-phenyl |
| 123 | 2,4-Cl$_2$-phenyl | C(O)NH-(2S)-2-CH$_2$OCH$_3$-pyrrolidin-1-yl | (Z)-CH-4-F-phenyl |
| 127 | 2,4-Cl$_2$-phenyl | C(O)NH-(R—CH)(pyridin-2-yl)-CH$_3$ | (Z)-CH-4-F-phenyl |
| 129 | 2,4-Cl$_2$-phenyl | C(O)NH—CH(phenyl)-R—CH$_3$ | (Z)-CH-4-Br-phenyl |
| 130 | 2,4-Cl$_2$-phenyl | C(O)NH-piperidin-1-yl | (Z)-CH-4-Br-phenyl |

An example of the invention is a compound of Formula (Ib)

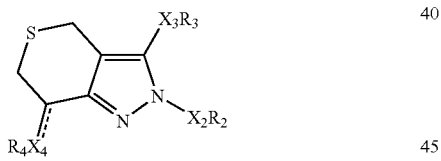

wherein $X_2R_2$, $X_3R_3$, and $X_4R_4$ are dependently selected from

| Cpd | $X_2R_2$ | $X_3R_3$ | $X_4R_4$ |
|---|---|---|---|
| 2 | CH$_2$-phenyl | CH=CHSO$_2$NH—CH(phenyl)-R—CH$_3$ | H |
| 5 | CH$_2$-phenyl | CH=CHSO$_2$NH—CH(phenyl)-S—CH$_3$ | H |
| 6 | CH$_2$-phenyl | CH=CHSO$_2$NH—CH(cyclohexyl)-R—CH$_3$ | H |
| 8 | CH$_2$-phenyl | CH=CHSO$_2$NH—CH(cyclohexyl)-S—CH$_3$ | H |
| 78 | 2,4-Cl$_2$-phenyl | C(O)NH—CH(phenyl)-R—CH$_3$ | (Z)-CH-4-F-phenyl |
| 88 | 2,4-Cl$_2$-phenyl | C(O)NH—piperidin-1-yl | (Z)-CH-4-F-phenyl |
| 89 | 2,4-Cl$_2$-phenyl | C(O)NH—CH(cyclohexyl)-R—CH$_3$ | (Z)-CH-4-F-phenyl |
| 90 | 2,4-Cl$_2$-phenyl | C(O)NH—CH(cyclohexyl)-S—CH$_3$ | (Z)-CH-4-F-phenyl |
| 91 | 2,4-Cl$_2$-phenyl | C(O)NH—CH(phenyl)-S—CH$_3$ | (Z)-CH-4-F-phenyl |
| 92 | 2,4-Cl$_2$-phenyl | C(O)NH-hexahydro-cyclopenta[c]pyrrol-2-yl | (Z)-CH-4-F-phenyl |

An example of the invention is a compound of Formula (Ic)

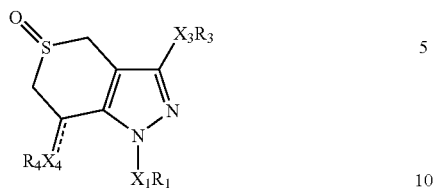

wherein $X_1R_1$, $X_3R_3$, and $X_4R_4$ are dependently selected from

| Cpd | $X_1R_1$ | $X_3R_3$ | $X_4R_4$ |
|---|---|---|---|
| 21 | $CH_2$-phenyl | C(O)NH-1,3,3-$(CH_3)_3$-bicyclo[2.2.1]hept-2-yl | H |
| 25 | $CH_2$-phenyl | CH=CHSO$_2$NH—CH(cyclohexyl)-CH$_3$ | H |
| 29 | $CH_2$-phenyl | CH=CHSO$_2$NH—CH(phenyl)-CH$_3$ | H |
| 30 | $CH_2$-phenyl | CH=CHSO$_2$NH—CH(phenyl)-R—CH$_3$ | H |
| 31 | $CH_2$-phenyl | CH=CHSO$_2$NH—CH(phenyl)-S—CH$_3$ | H |
| 34 | $CH_2$-phenyl | CH=CHC(O)NH—CH(phenyl)-S—CH$_3$ | H |
| 35 | $CH_2$-phenyl | CH=CHC(O)NH-CH(phenyl)-R—CH$_3$ | H |
| 74 | 2,4-Cl$_2$-phenyl | C(O)NH—CH(phenyl)-S—CH$_3$ | (Z)-CH-4-F-phenyl |
| 75 | 2,4-Cl$_2$-phenyl | C(O)NH—CH(phenyl)-R—CH$_3$ | (Z)-CH-4-F-phenyl |
| 76 | 2,4-Cl$_2$-phenyl | C(O)NH-(1R,2R)-2-OH-cyclopentyl | (Z)-CH-4-F-phenyl |
| 77 | 2,4-Cl$_2$-phenyl | C(O)NHNH-2,4-Cl$_2$-phenyl | (Z)-CH-4-F-phenyl |
| 79 | 2,4-Cl$_2$-phenyl | C(O)NH-piperidin-1-yl | (Z)-CH-4-F-phenyl |
| 80 | 2,4-Cl$_2$-phenyl | C(O)NHCH$_2$-pyridin-2-yl | (Z)-CH-4-F-phenyl |
| 96 | 4-Cl-phenyl | C(O)NH-piperidin-1-yl | (Z)-CH-4-F-phenyl |

An example of the invention is a compound of Formula (Id)

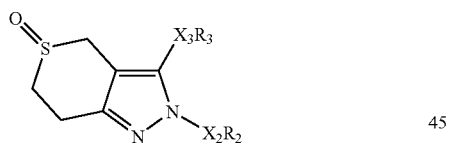

wherein $X_2R_2$ and $X_3R_3$ are dependently selected from

| Cpd | $X_2R_2$ | $X_3R_3$ |
|---|---|---|
| 22 | $CH_2$-phenyl | CH=CHSO$_2$NH—CH(phenyl)-CH$_3$ |
| 23 | $CH_2$-phenyl | CH=CHSO$_2$NH—CH(phenyl)-R—CH$_3$ |
| 24 | $CH_2$-phenyl | CH=CHSO$_2$NH—CH(phenyl)-S—CH$_3$ |
| 26 | $CH_2$-phenyl | CH=CHSO$_2$NH—CH(cyclohexyl)-CH$_3$ |
| 27 | $CH_2$-phenyl | CH=CHSO$_2$NH—CH(cyclohexyl)-R—CH$_3$ |
| 28 | $CH_2$-phenyl | CH=CHSO$_2$NH—CH(cyclohexyl)-S—CH$_3$ |

An example of the invention is a compound of Formula (Ie)

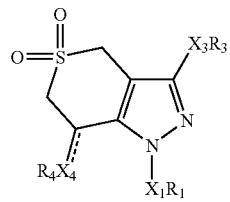

wherein $X_1R_1$, $X_3R_3$, and $X_4R_4$ are dependently selected from

| Cpd | $X_1R_1$ | $X_3R_3$ | $X_4R_4$ |
|---|---|---|---|
| 9 | $CH_2$-phenyl | CH=CHSO$_2$NH—CH(phenyl)-R—CH$_3$ | H |
| 13 | $CH_2$-phenyl | C(O)NH—CH(phenyl)-R—CH$_3$ | H |
| 14 | $CH_2$-phenyl | CH=CHSO$_2$NH—CH(cyclohexyl)-R—CH$_3$ | H |
| 15 | $CH_2$-phenyl | CH=CHSO$_2$NH—CH(cyclohexyl)-S—CH$_3$ | H |
| 18 | $CH_2$-phenyl | CH=CHSO$_2$NH—CH(phenyl)-S—CH$_3$ | H |
| 20 | $CH_2$-phenyl | C(O)NH-1,3,3-(CH$_3$)$_3$-bicyclo[2.2.1]hept-2-yl | H |
| 36 | $CH_2$-phenyl | CH=CHC(O)NH—CH(phenyl)-S—CH$_3$ | H |
| 37 | $CH_2$-phenyl | CH=CHC(O)NH—CH(phenyl)-R—CH$_3$ | H |
| 42 | 2,4-F$_2$-phenyl | CH=CHSO$_2$NH—CH(phenyl)-S—CH$_3$ | CH$_2$-3-F-phenyl |
| 43 | 2,4-F$_2$-phenyl | CH=CHSO$_2$NH—CH(cyclohexyl)-R—CH$_3$ | CH$_2$-3-F-phenyl |
| 44 | 2,4-F$_2$-phenyl | CH=CHSO$_2$NH-morpholin-4-yl | CH$_2$-3-F-phenyl |
| 45 | 2,4-F$_2$-phenyl | CH=CHSO$_2$NH-piperidin-1-yl | CH$_2$-3-F-phenyl |
| 49 | 2,4-F$_2$-phenyl | C(O)NH-(2R,3 S)-2-C(O)OCH$_2$CH$_3$-bicyclo[2.2.1]heptan-3-yl | R—CH$_2$-3-F-phenyl |
| 50 | 2,4-F$_2$-phenyl | C(O)NH-(2R,3S)-2-C(O)OCH$_2$CH$_3$-bicyclo[2.2.1]heptan-3-yl | S—CH$_2$-3-F-phenyl |
| 51 | 2,4-F$_2$-phenyl | C(O)NH-(1R,2S)-2-OH-indan-1-yl | CH$_2$-3-F-phenyl |
| 53 | 2,4-Cl$_2$-phenyl | C(O)NHNH-2,4-Cl$_2$-phenyl | CH$_2$-4-F-phenyl |
| 65 | 2,4-Cl$_2$-phenyl | C(O)NH—CH(phenyl)-S—CH$_3$ | (Z)-CH-4-F-phenyl |
| 66 | 2,4-Cl$_2$-phenyl | C(O)NH—CH(phenyl)-R—CH$_3$ | (Z)-CH-4-F-phenyl |
| 67 | 2,4-Cl$_2$-phenyl | C(O)NH-(1R,2R)-2-OH-cyclopentyl | (Z)-CH-4-F-phenyl |
| 68 | 2,4-Cl$_2$-phenyl | C(O)NH-(1S,2S)-2-OH-cyclohexyl | (Z)-CH-4-F-phenyl |
| 69 | 2,4-Cl$_2$-phenyl | C(O)NH-(1R,2S)-2-OH-indan-1-yl | (Z)-CH-4-F-phenyl |
| 70 | 2,4-Cl$_2$-phenyl | C(O)NH-(1S,2R)-2-OH-indan-1-yl | (Z)-CH-4-F-phenyl |
| 71 | 2,4-Cl$_2$-phenyl | C(O)NH$_2$ | (Z)-CH-4-F-phenyl |
| 73 | 2,4-Cl$_2$-phenyl | C(O)NH—CH$_2$-pyridin-2-yl | (Z)-CH-4-F-phenyl |
| 81 | 2,4-Cl$_2$-phenyl | C(O)NH-piperidin-1-yl | (Z)-CH-4-F-phenyl |
| 95 | 4-Cl-phenyl | C(O)NH—CH(phenyl)-R—CH$_3$ | (Z)-CH-4-F-phenyl |
| 97 | 4-Cl-phenyl | C(O)NH-hexahydro-cyclopenta[c]pyrrol-2-yl | (Z)-CH-4-F-phenyl |
| 98 | 4-Cl-phenyl | C(O)-piperidin-1-yl | (Z)-CH-4-F-phenyl |
| 99 | 4-Cl-phenyl | C(O)-NH-piperidin-1-yl | (Z)-CH-4-F-phenyl |
| 100 | 4-Cl-phenyl | C(O)NHN(CH$_3$)-phenyl | (Z)-CH-4-F-phenyl |
| 101 | 2,4-Cl$_2$-phenyl | C(O)-piperidin-1-yl | (Z)-CH-4-F-phenyl |
| 104 | 2,4-Cl$_2$-phenyl | C(O)NH-hexahydro-cyclopenta[c]pyrrol-2-yl | (Z)-CH-4-F-phenyl |
| 105 | 2,4-F$_2$-phenyl | C(O)NH-hexahydro-cyclopenta[c]pyrrol-2-yl | (Z)-CH-4-F-phenyl |
| 106 | 2,4-F$_2$-phenyl | C(O)NH-piperidin-1-yl | (Z)-CH-4-F-phenyl |
| 107 | 2,4-Cl$_2$-phenyl | C(O)NH-azepan-1-yl | (Z)-CH-4-F-phenyl |
| 108 | 2,4-Cl$_2$-phenyl | C(O)NH-2,6-(CH$_3$)$_2$-piperidin-1-yl | (Z)-CH-4-F-phenyl |
| 109 | 2,4-Cl$_2$-phenyl | C(O)NH-4-CH$_3$-piperazin-1-yl | (Z)-CH-4-F-phenyl |
| 110 | 2,4-Cl$_2$-phenyl | C(O)NH-4-(CH$_2$)$_2$OH-piperazin-1-yl | (Z)-CH-4-F-phenyl |
| 117 | 2,4-Cl$_2$-phenyl | C(O)NH—CH(phenyl)-R—CH$_3$ | (Z)-CH-5-Cl-fur-2-yl |
| 118 | 2,4-Cl$_2$-phenyl | C(O)NH—CH(cyclohexyl)-R—CH$_3$ | (Z)-CH-5-Cl-fur-2-yl |
| 119 | 2,4-Cl$_2$-phenyl | C(O)NH-piperidin-1-yl | (Z)-CH-5-Cl-fur-2-yl |
| 120 | 2,4-Cl$_2$-phenyl | C(O)NH-azepan-1-yl | (Z)-CH-5-Cl-fur-2-yl |
| 121 | 2,4-Cl$_2$-phenyl | C(O)NH-hexahydro-cyclopenta[c]pyrrol-2-yl | (Z)-CH-5-Cl-fur-2-yl |
| 124 | 2,4-Cl$_2$-phenyl | C(O)NH-(R—CH)(pyridin-2-yl)-CH$_3$ | (Z)-CH-4-F-phenyl |
| 125 | 2,4-Cl$_2$-phenyl | C(O)NH-(2S)-2-CH$_2$OCH$_3$-pyrrolidin-1-yl | (Z)-CH-4-F-phenyl |
| 126 | 2,4-Cl$_2$-phenyl | C(O)NH-(2R)-2-CH$_2$OCH$_3$-pyrrolidin-1-yl | (Z)-CH-4-F-phenyl |
| 128 | 2,4-Cl$_2$-phenyl | C(O)NH—CH(phenyl)-R—CH$_3$ | H |

An example of the invention is a compound of Formula (If)

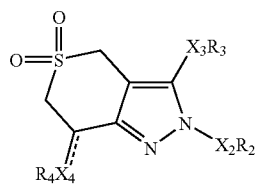

(5)

wherein $X_2R_2$, $X_3R_3$, and $X_4R_4$ are dependently selected from

| Cpd | $X_2R_2$ | $X_3R_3$ | $X_4R_4$ |
|---|---|---|---|
| 4 | $CH_2$-phenyl | CH=CHSO$_2$NH—CH(phenyl)-R—CH$_3$ | H |
| 10 | $CH_2$-phenyl | CH=CHSO$_2$NH—CH(phenyl)-S—CH$_3$ | H |
| 16 | $CH_2$-phenyl | CH=CHSO$_2$NH—CH(cyclohexyl)-R—CH$_3$ | H |
| 17 | $CH_2$-phenyl | CH=CHSO$_2$NH—CH(cyclohexyl)-S—CH$_3$ | H |
| 82 | 2,4-Cl$_2$-phenyl | C(O)NH—CH(phenyl)-R—CH$_3$ | (Z)-CH-4-F-phenyl |
| 83 | 2,4-Cl$_2$-phenyl | C(O)NH-piperidin-1-yl | (Z)-CH-4-F-phenyl |
| 84 | 2,4-Cl$_2$-phenyl | C(O)NH—CH(cyclohexyl)-R—CH$_3$ | (Z)-CH-4-F-phenyl |
| 85 | 2,4-Cl$_2$-phenyl | C(O)NH—CH(cyclohexyl)-S—CH$_3$ | (Z)-CH-4-F-phenyl |
| 86 | 2,4-Cl$_2$-phenyl | C(O)NH—CH(phenyl)-S—CH$_3$ | (Z)-CH-4-F-phenyl |
| 87 | 2,4-Cl$_2$-phenyl | C(O)NH-hexahydro-cyclopenta[c]pyrrol-2-yl | (Z)-CH-4-F-phenyl |

Compounds of the invention are also represented as follows:

Cpd 1

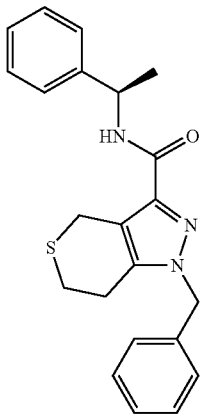

Cpd 2

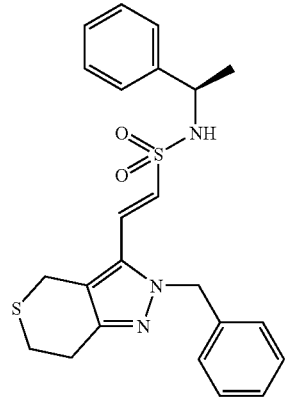

Cpd 3

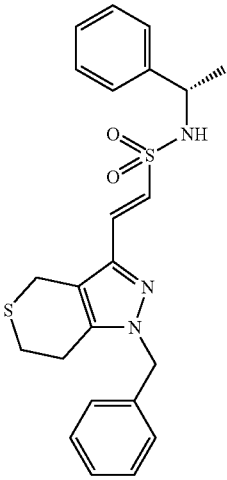

Cpd 4

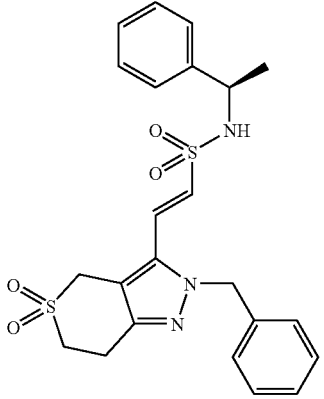

-continued
Cpd 5
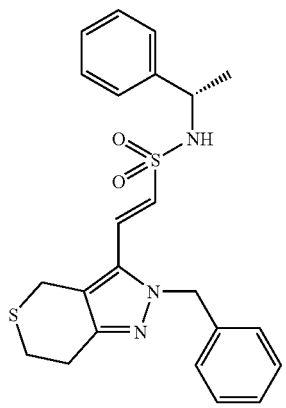
Cpd 6
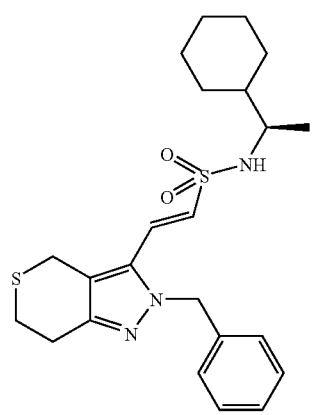
Cpd 7
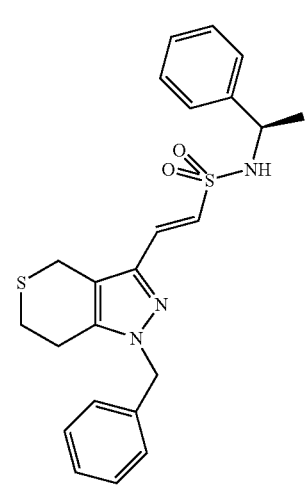
Cpd 8
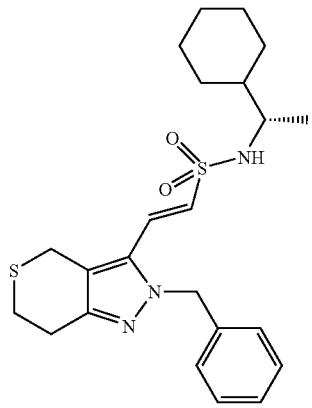
Cpd 9
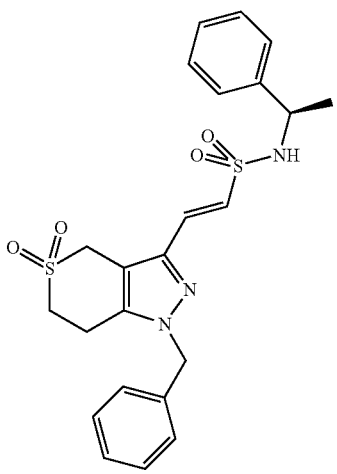
Cpd 10
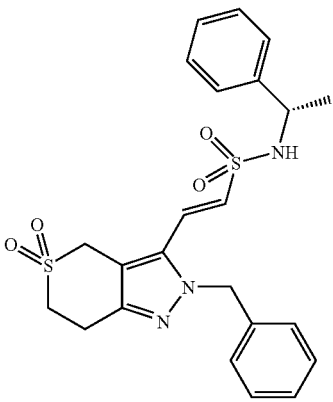

-continued
Cpd 11
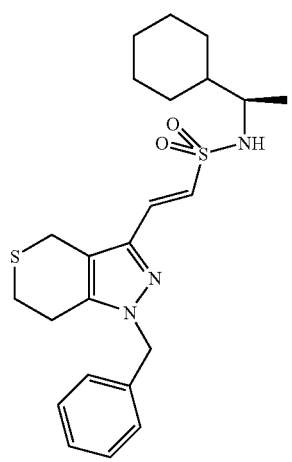
Cpd 12
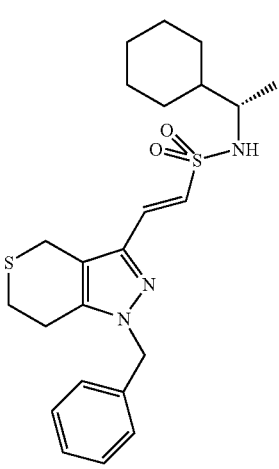
Cpd 13
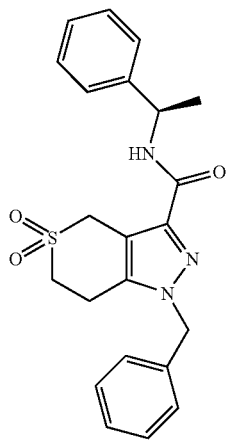
-continued
Cpd 14
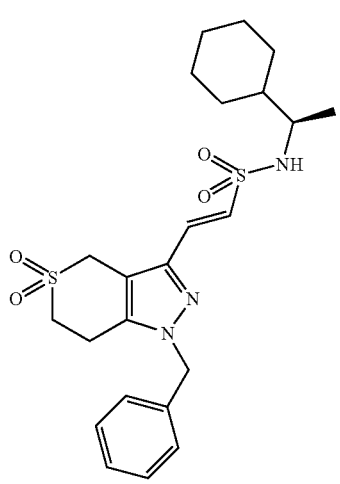
Cpd 15
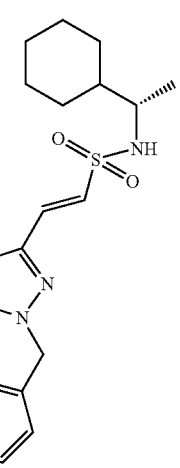
Cpd 16
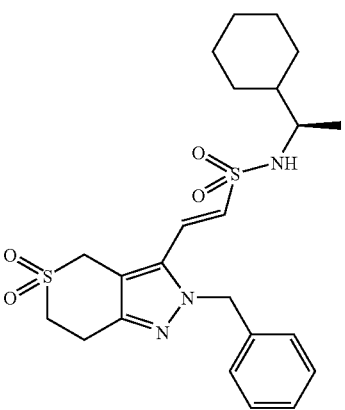

-continued
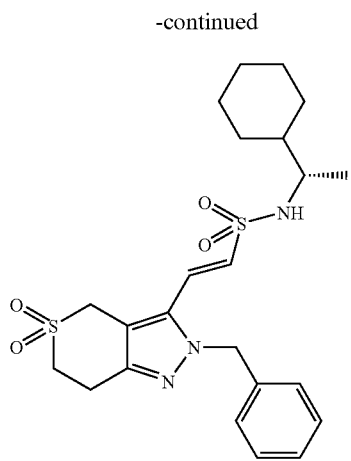
Cpd 17
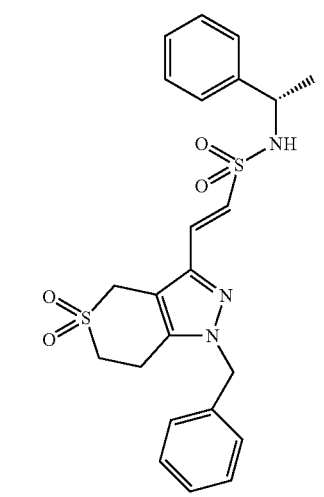
Cpd 18
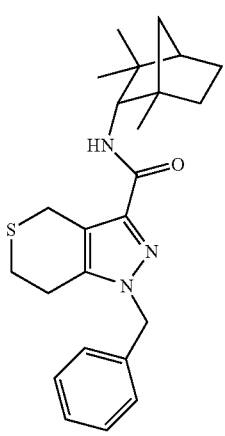
Cpd 19
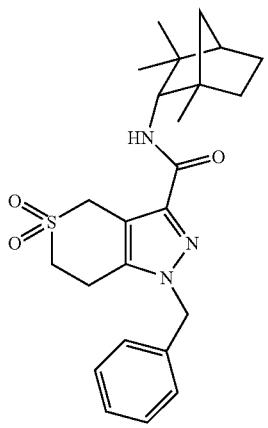
Cpd 20
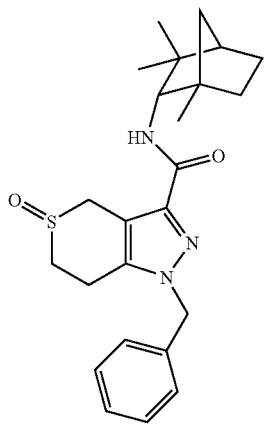
Cpd 21
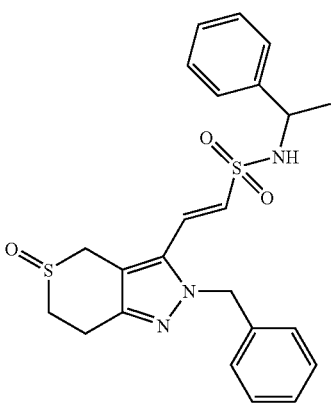
Cpd 22

-continued
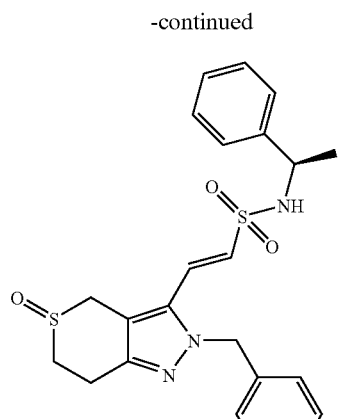
Cpd 23
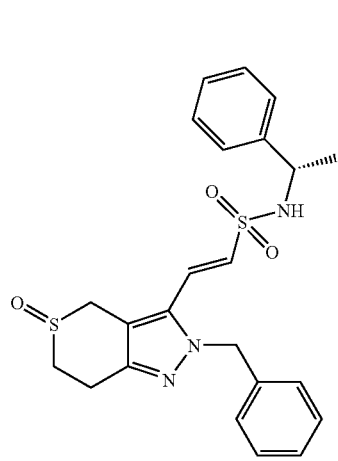
Cpd 24
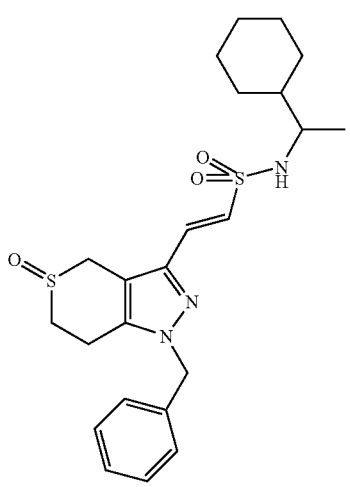
Cpd 25
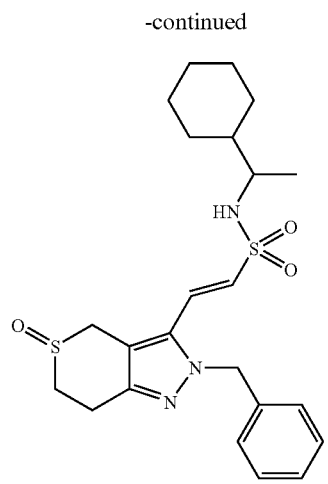
Cpd 26
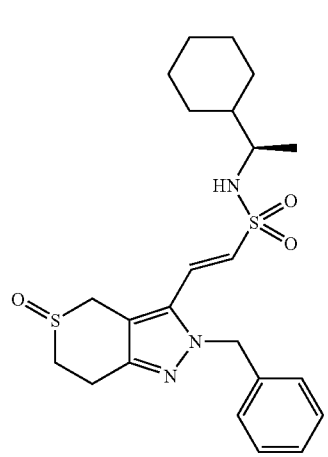
Cpd 27
Cpd 28

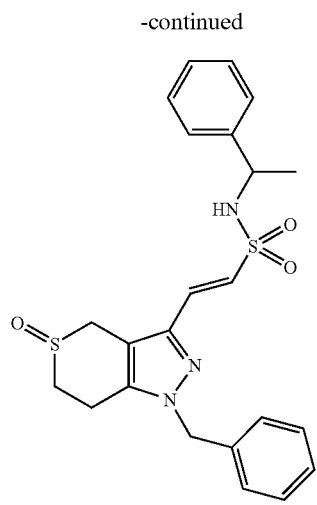
Cpd 29
Cpd 30
Cpd 31
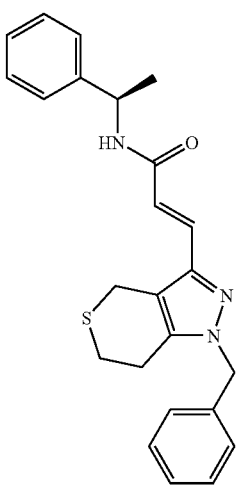
Cpd 32
Cpd 33
Cpd 34
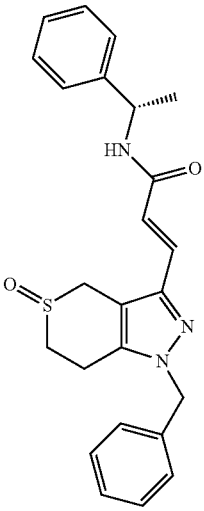

Cpd 35
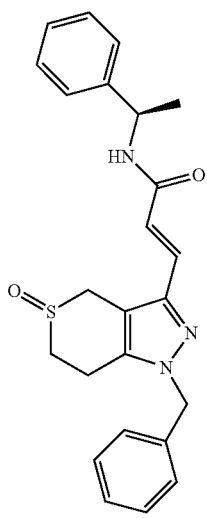
Cpd 38
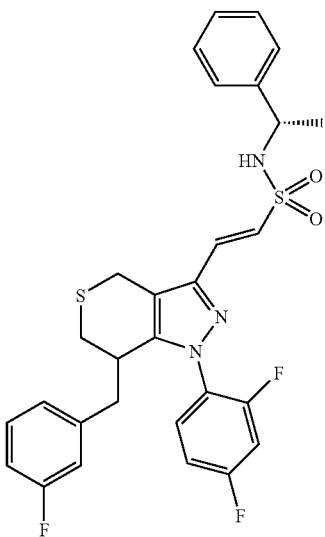
Cpd 36
Cpd 39
Cpd 37
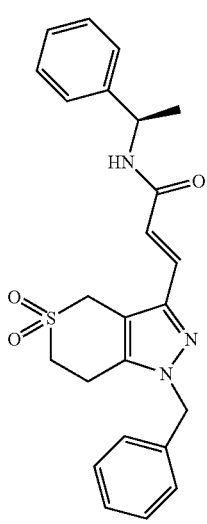
Cpd 40
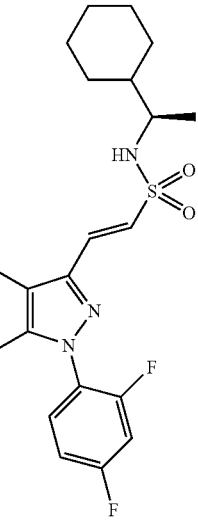

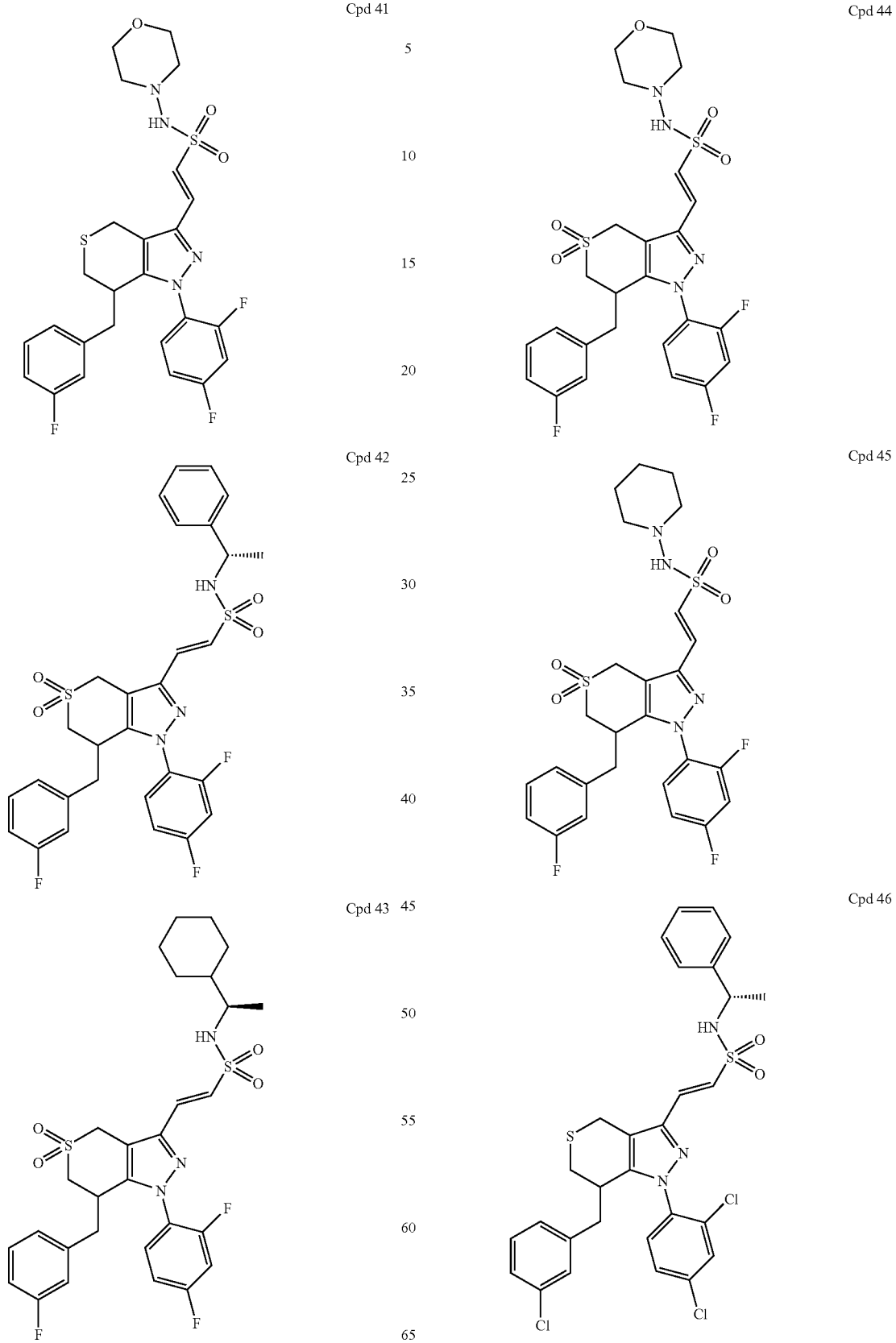

-continued
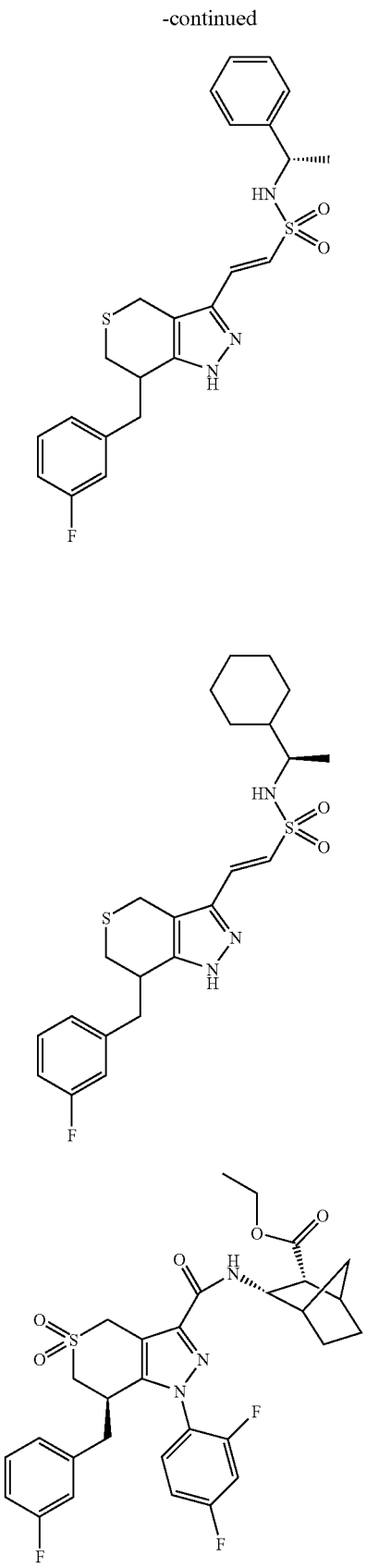
Cpd 47
Cpd 48
Cpd 49
-continued
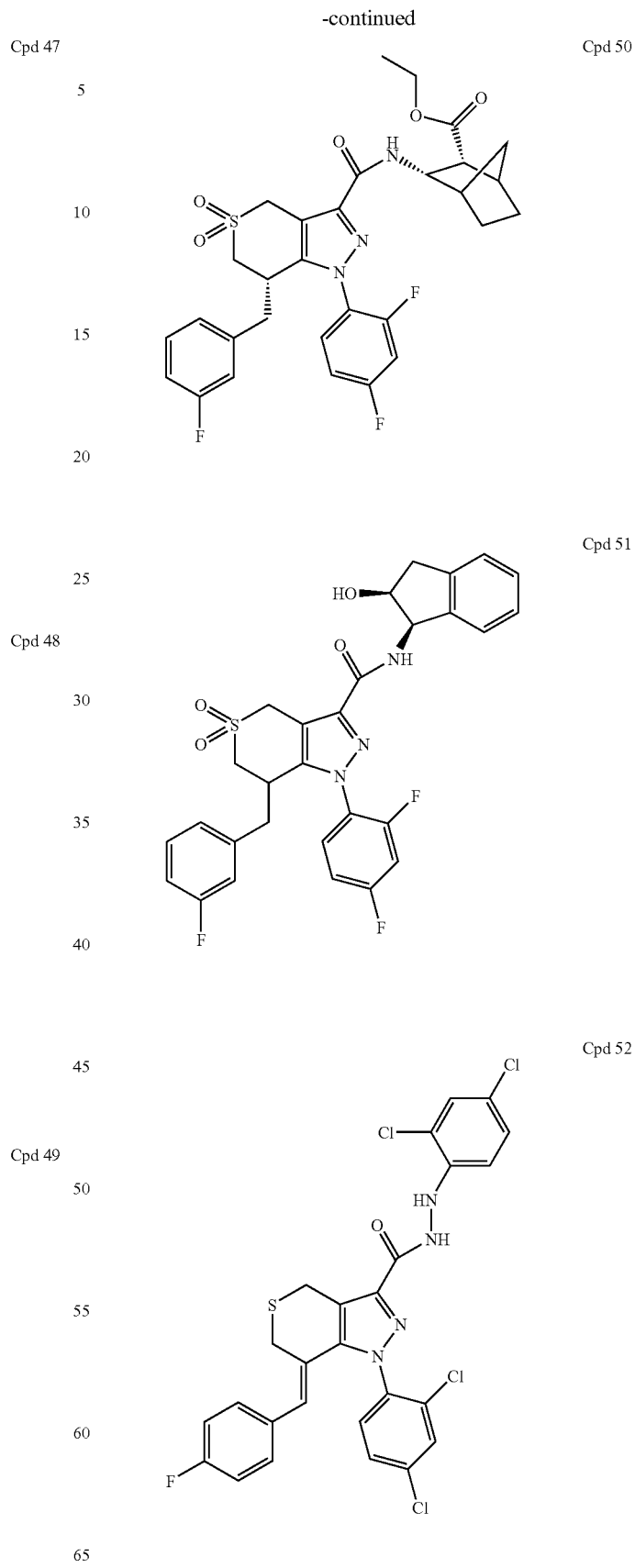
Cpd 50
Cpd 51
Cpd 52

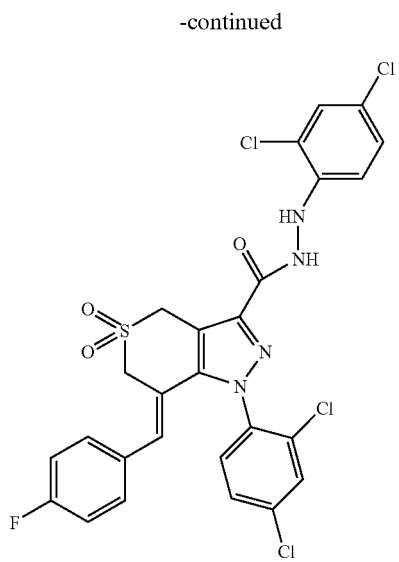
Cpd 53
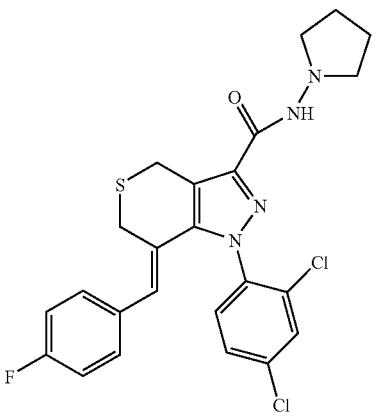
Cpd 56
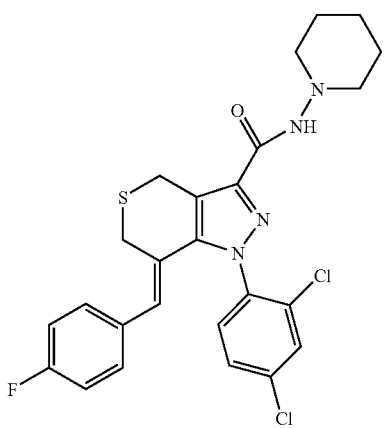
Cpd 54
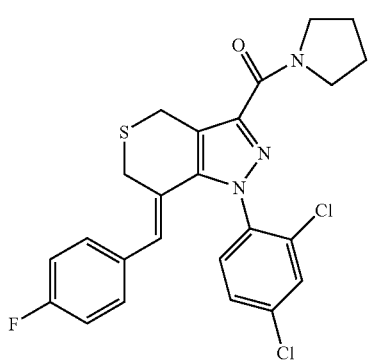
Cpd 57
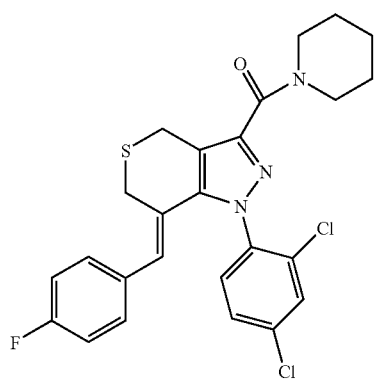
Cpd 55
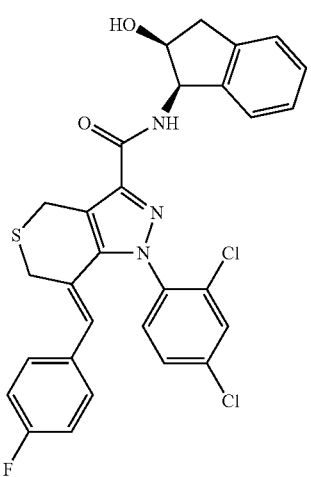
Cpd 58

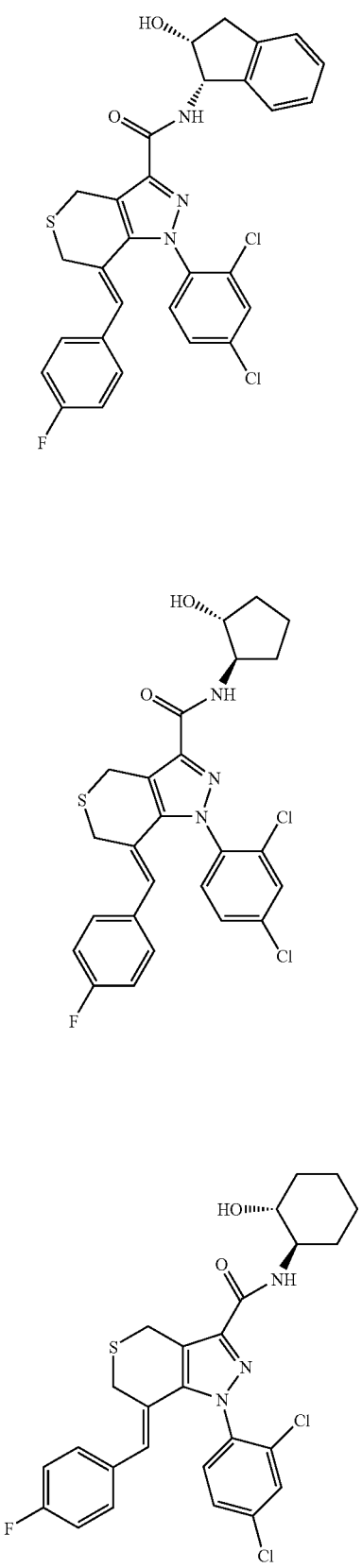
Cpd 59
Cpd 60
Cpd 61
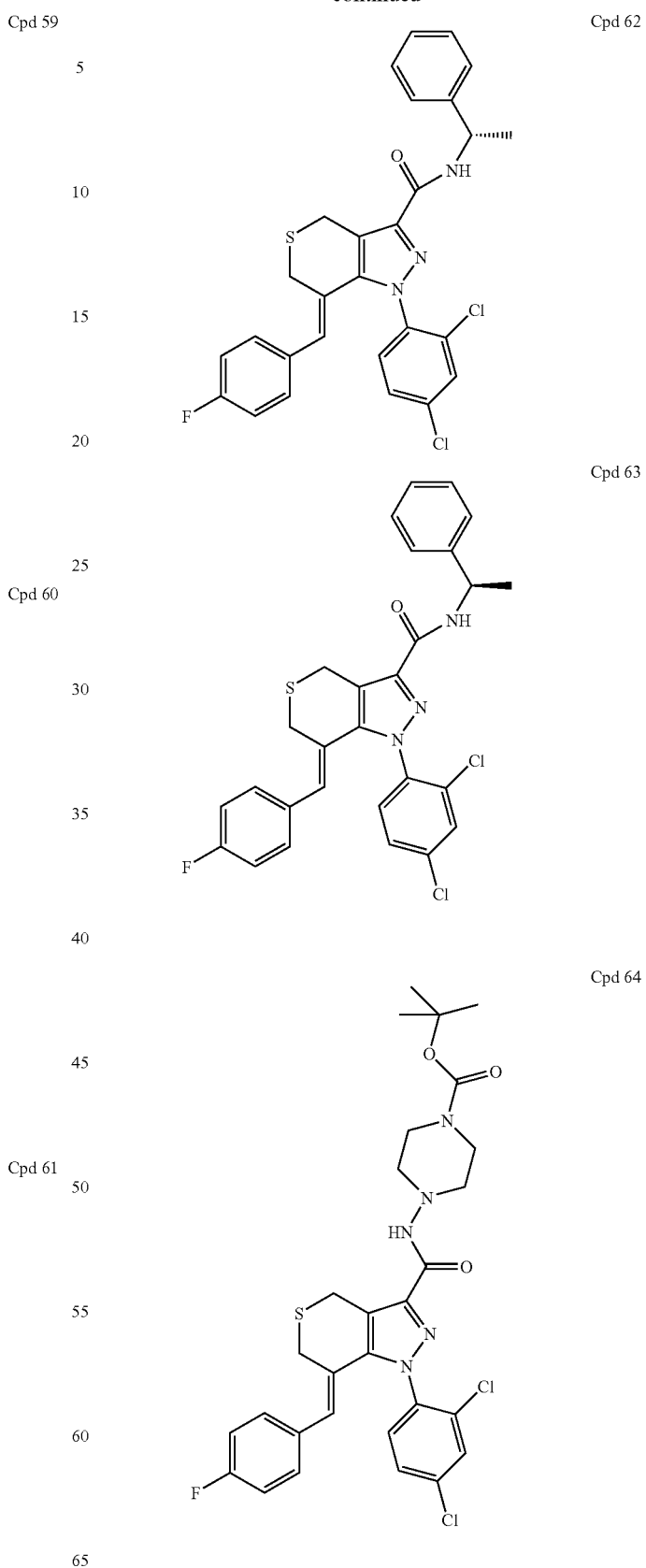
Cpd 62
Cpd 63
Cpd 64

-continued
Cpd 65
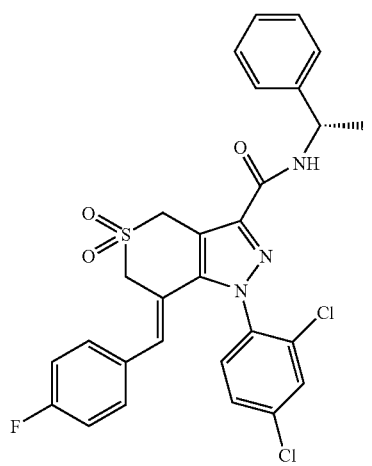
Cpd 66
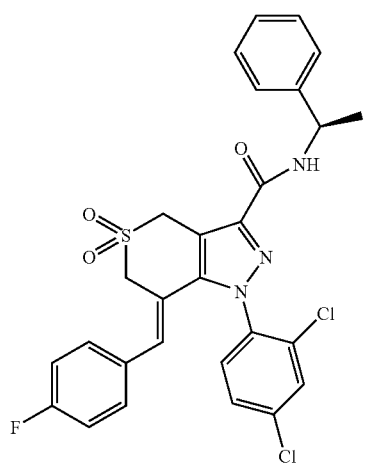
Cpd 67
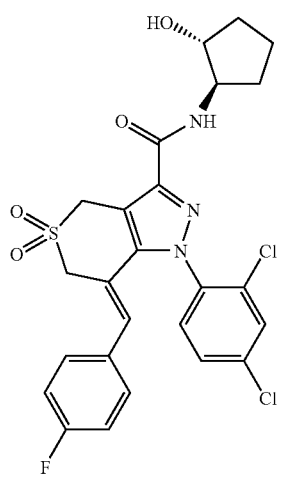
-continued
Cpd 68
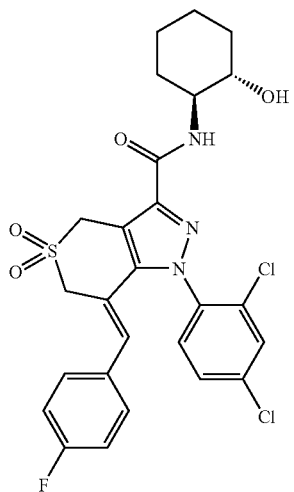
Cpd 69
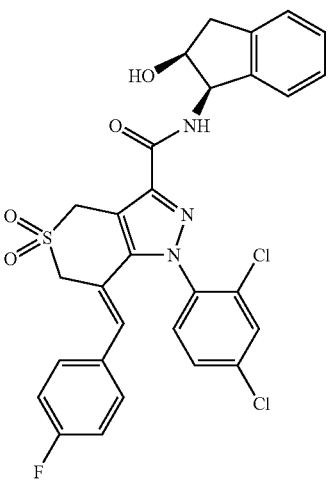
Cpd 70
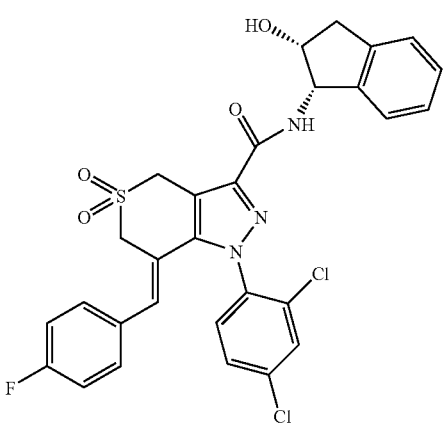

Cpd 71
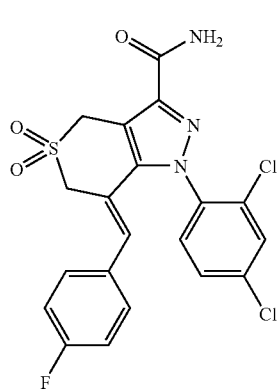
Cpd 72
Cpd 73
Cpd 74
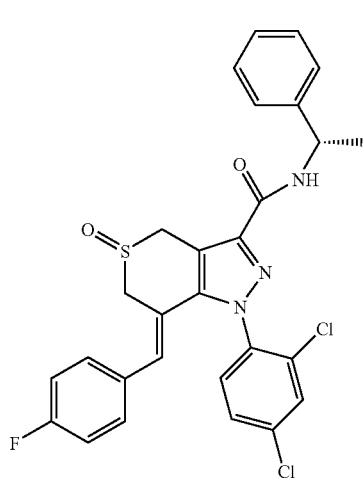
Cpd 75
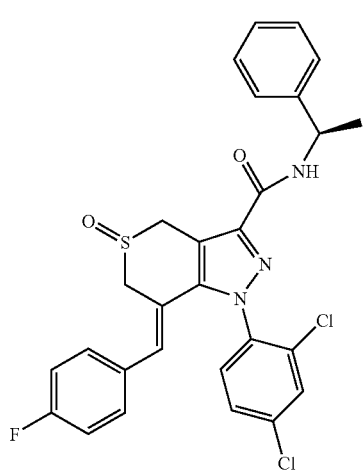
Cpd 76
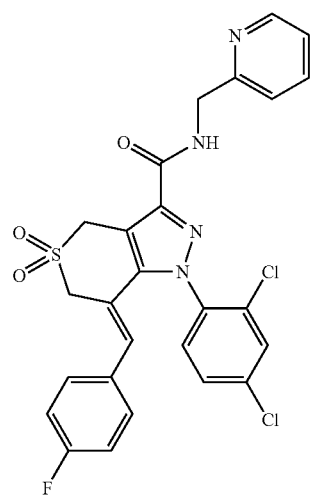

Cpd 77
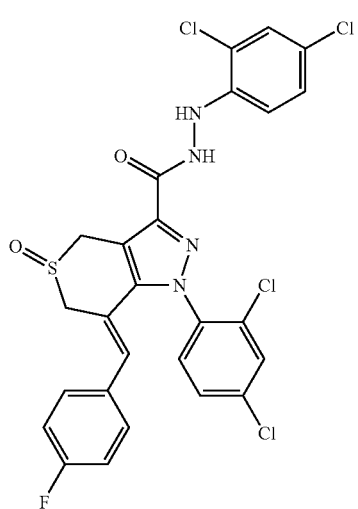
Cpd 78
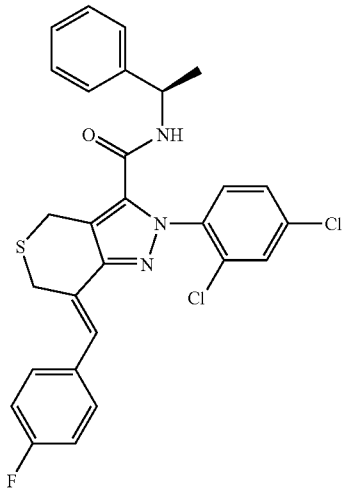
Cpd 79
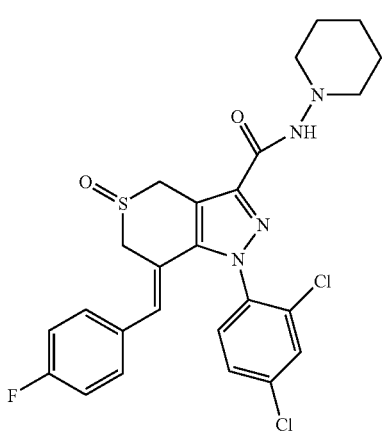
Cpd 80
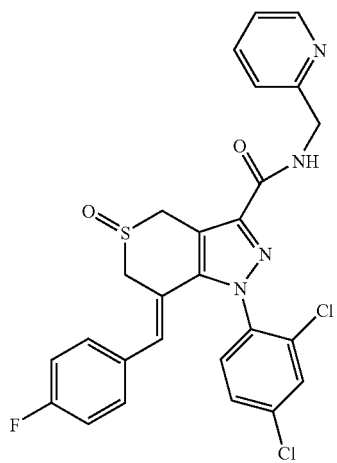
Cpd 81
Cpd 82
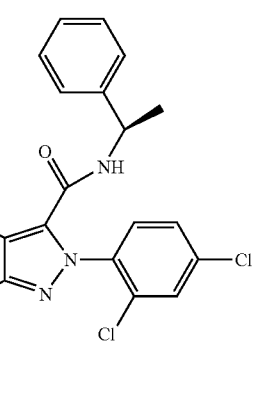

-continued
Cpd 83
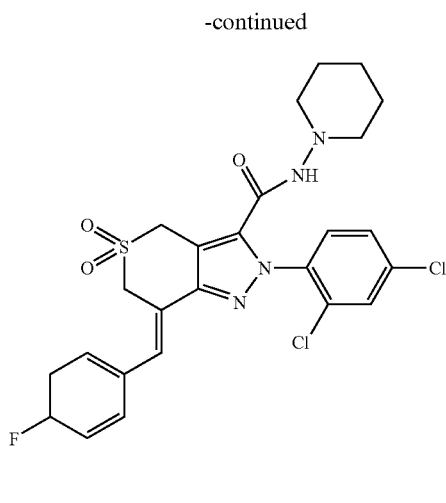
Cpd 84
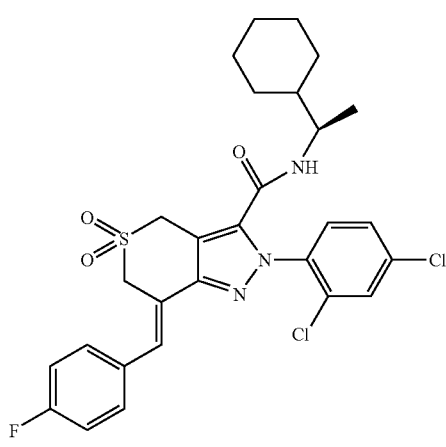
Cpd 85
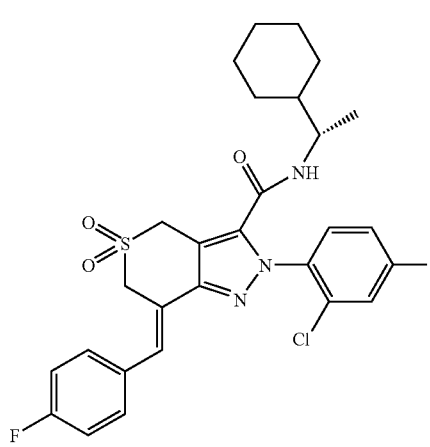
-continued
Cpd 86
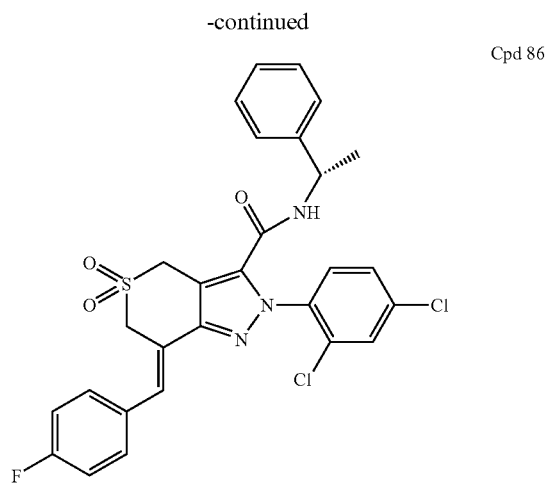
Cpd 87
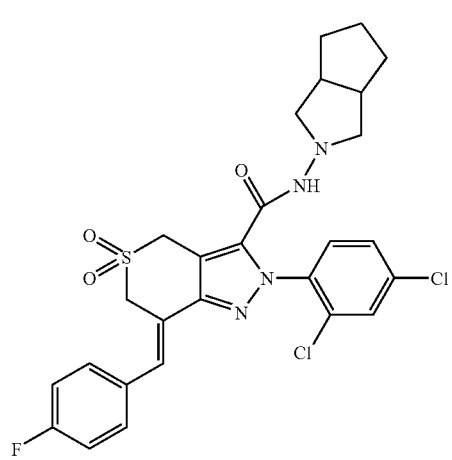
Cpd 88
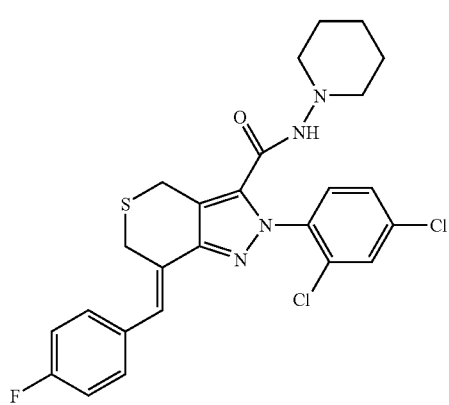

-continued
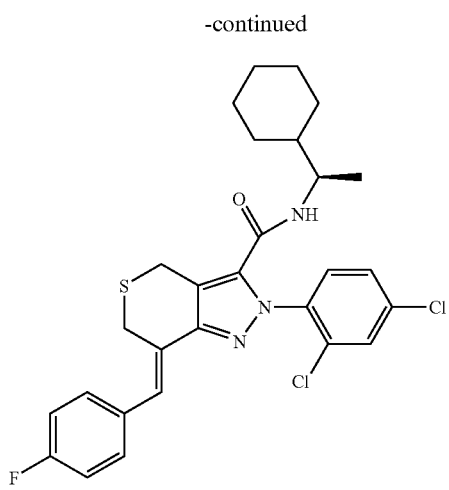
Cpd 89
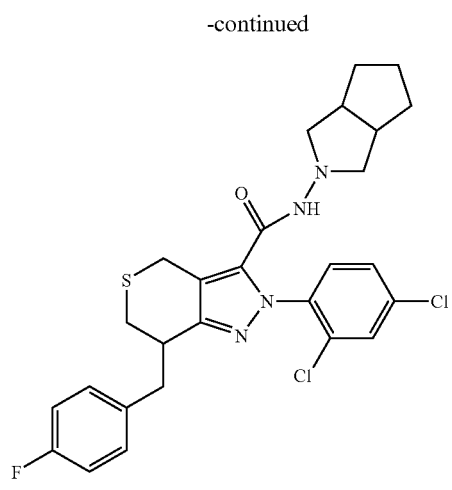
Cpd 92
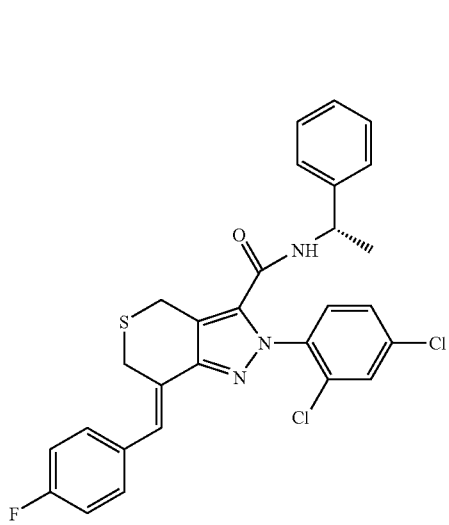
Cpd 90
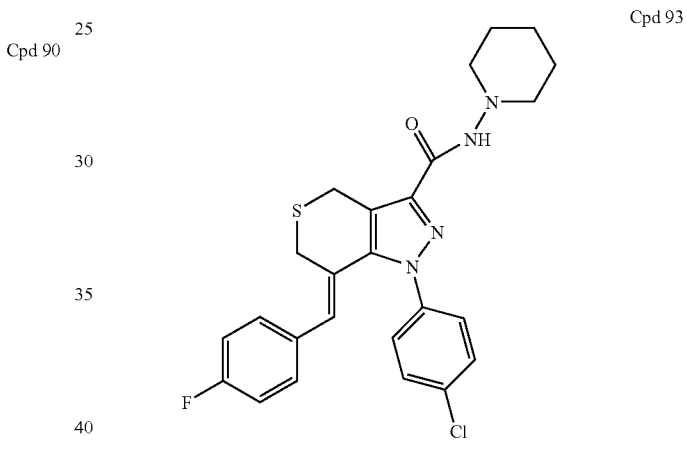
Cpd 93
Cpd 91
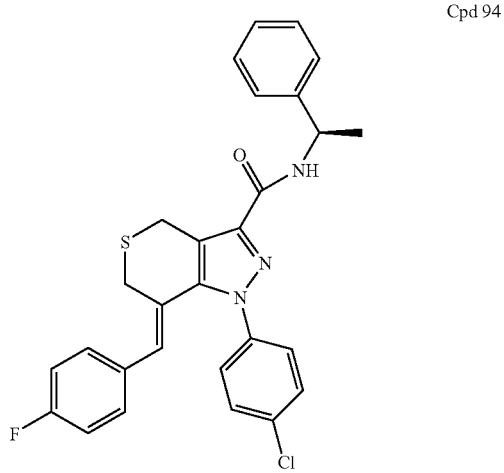
Cpd 94

Cpd 95
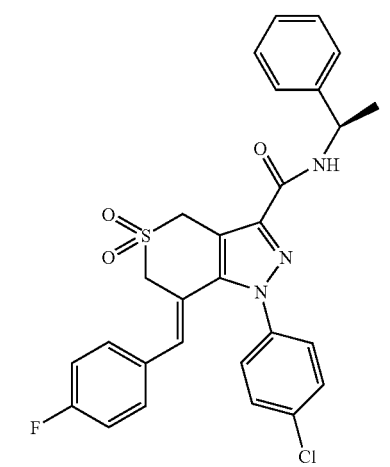
Cpd 96
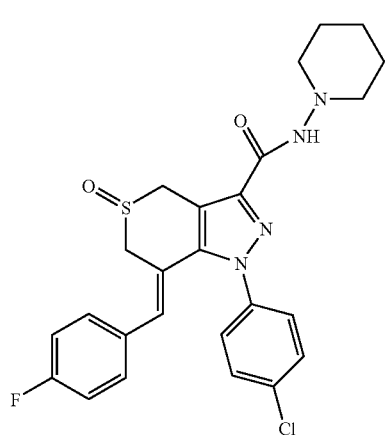
Cpd 97
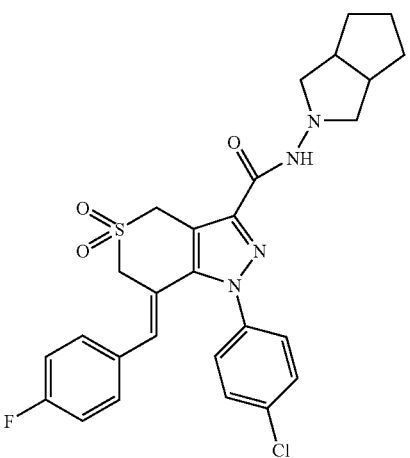
Cpd 98
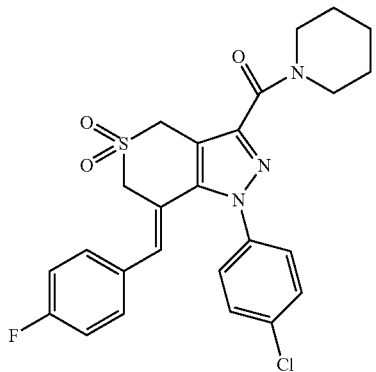
Cpd 99
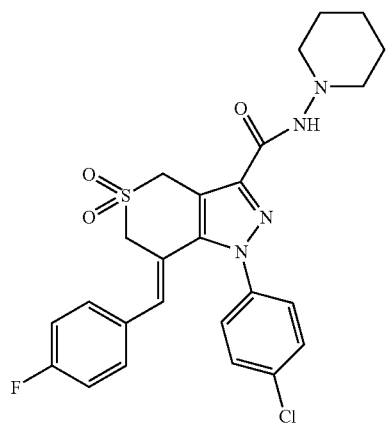
Cpd 100
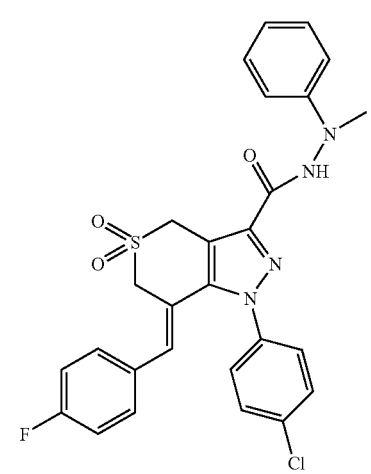
Cpd 101
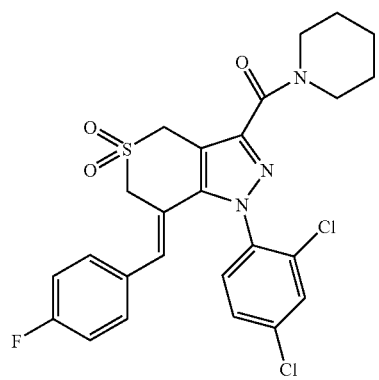

-continued
Cpd 102
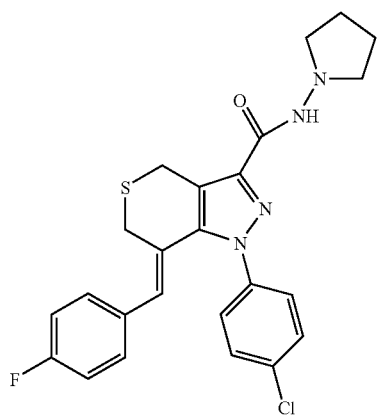
Cpd 103
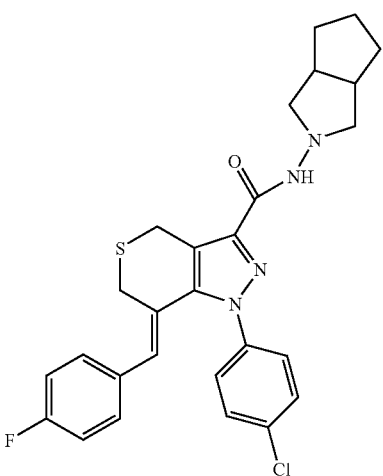
Cpd 104
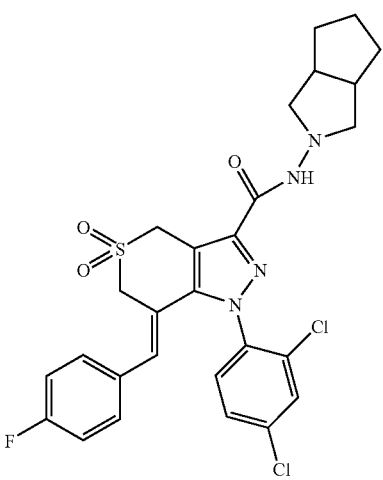
-continued
Cpd 105
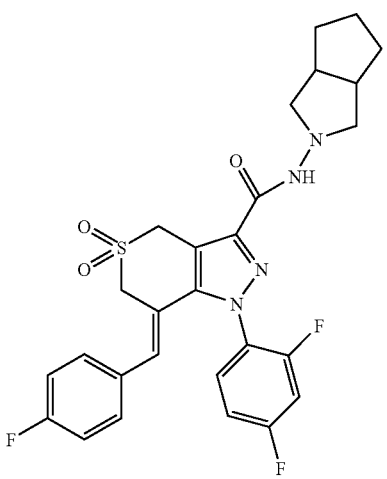
Cpd 106
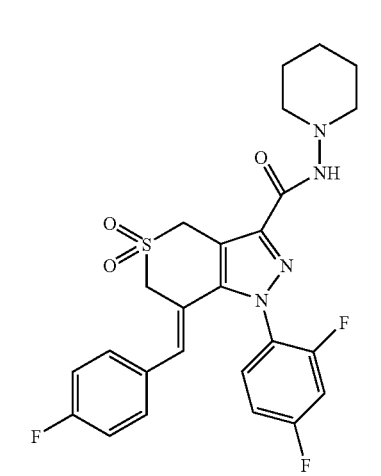
Cpd 107
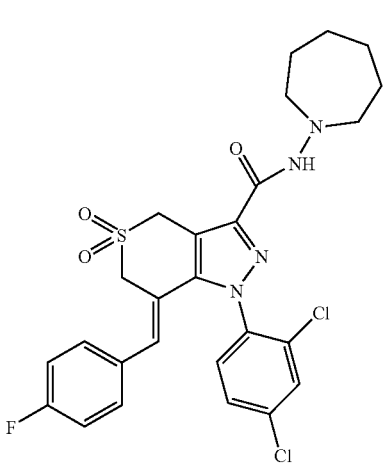

-continued
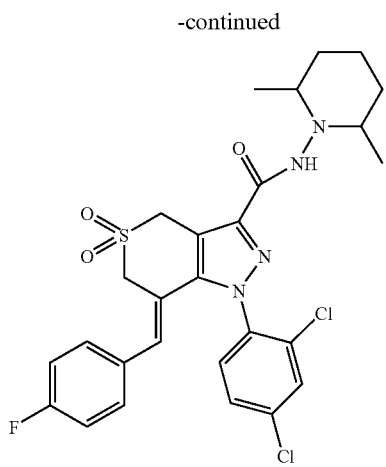
Cpd 108
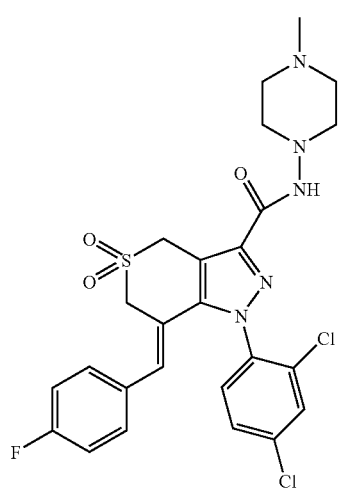
Cpd 109
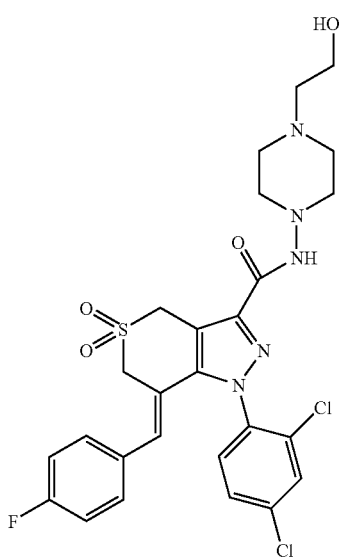
Cpd 110
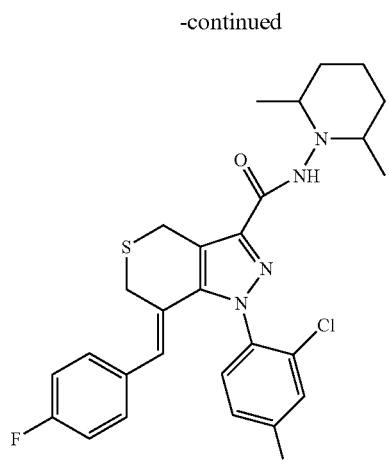
Cpd 111
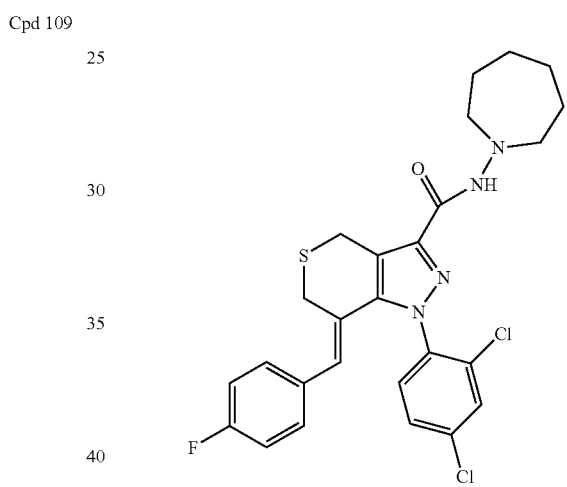
Cpd 112
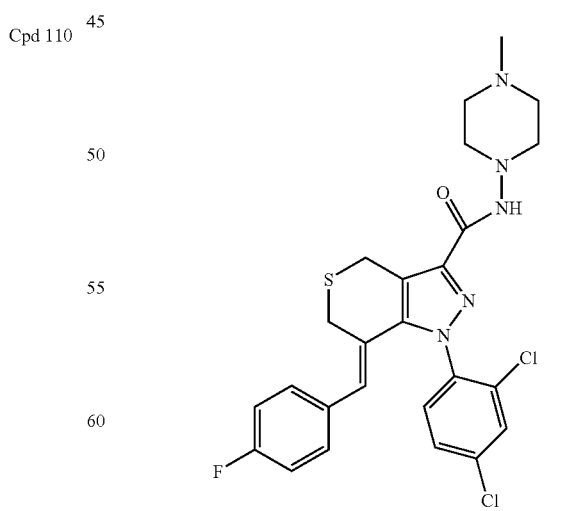
Cpd 113

Cpd 114
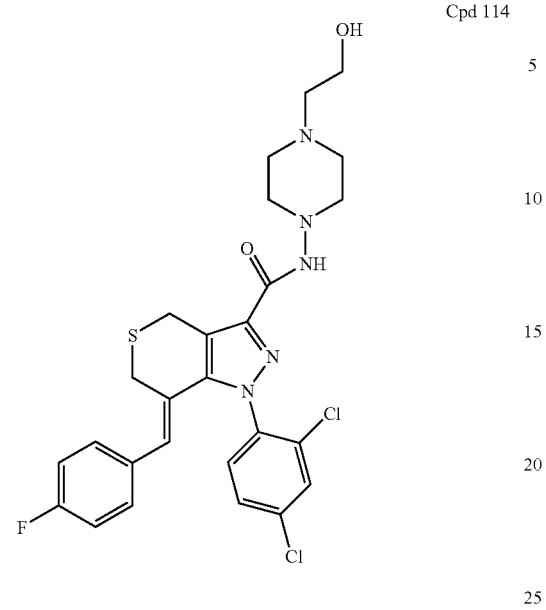
Cpd 117
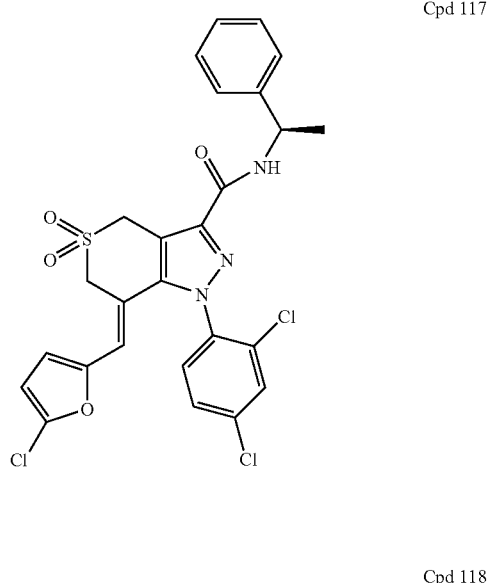
Cpd 115
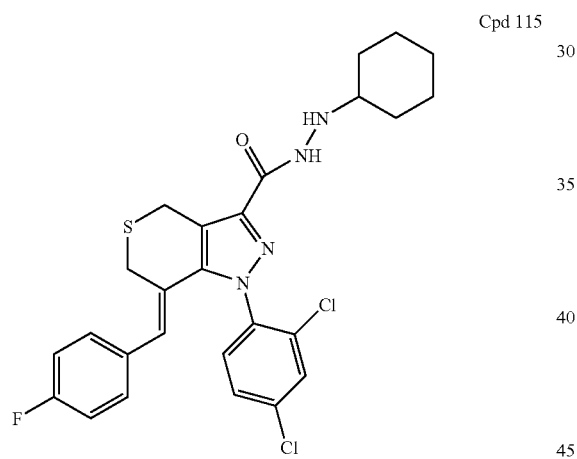
Cpd 118
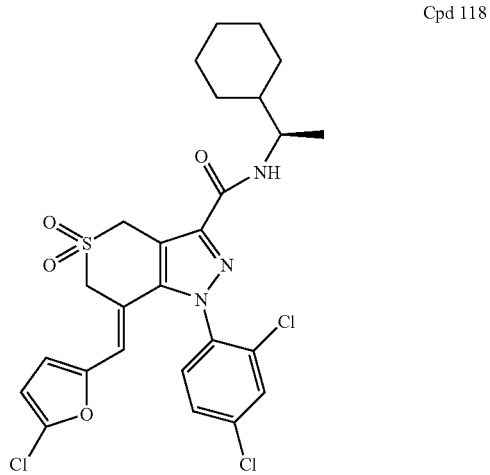
Cpd 116
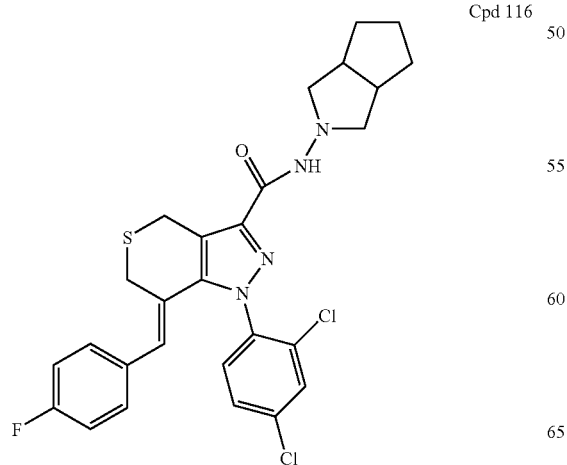
Cpd 119
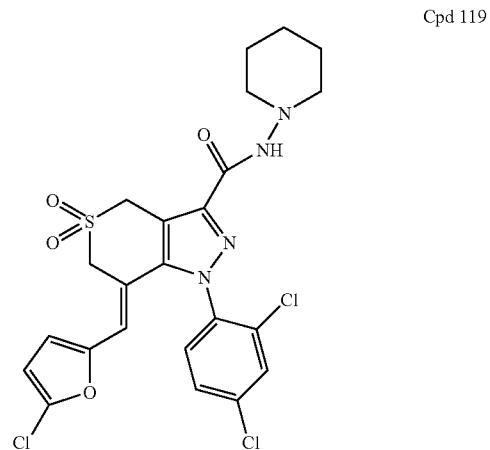

Cpd 120
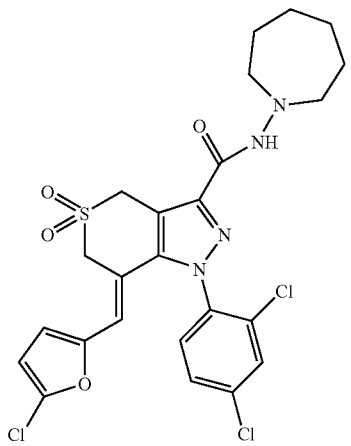
Cpd 121
Cpd 123
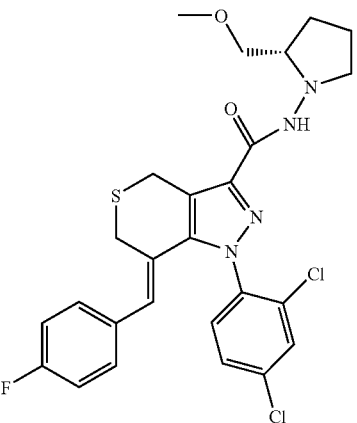
Cpd 124
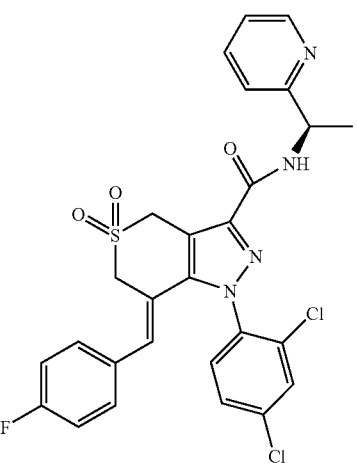
Cpd 122
Cpd 125
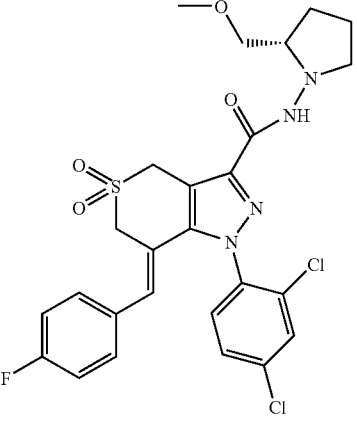

Cpd 126
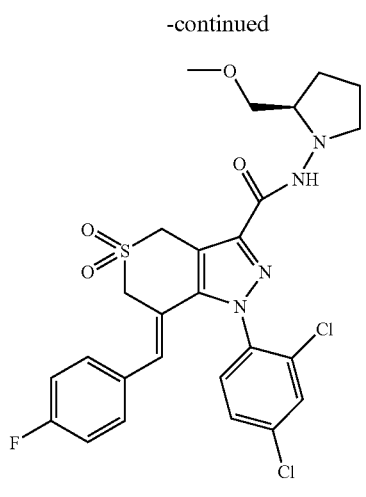
Cpd 129
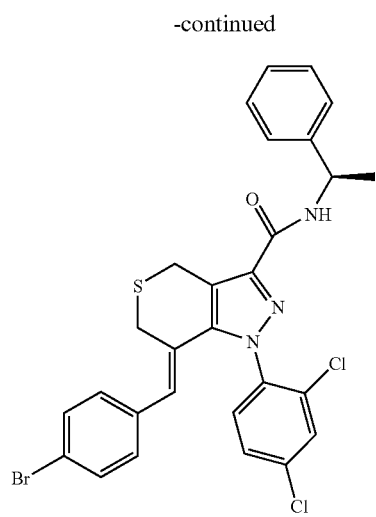
Cpd 127
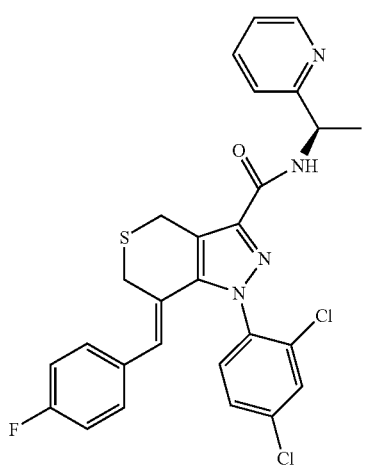
Cpd 130
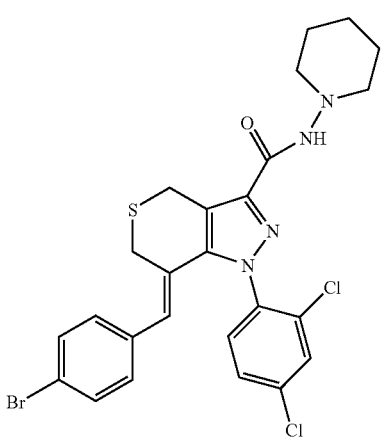
Cpd 128
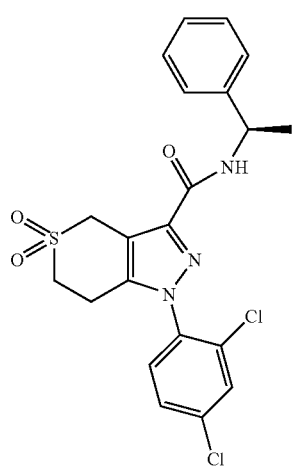
Selected compounds of the invention include:
Cpd 1
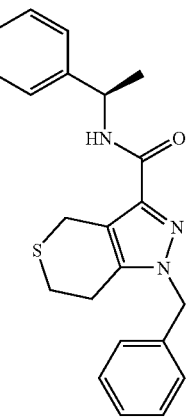

-continued
Cpd 7
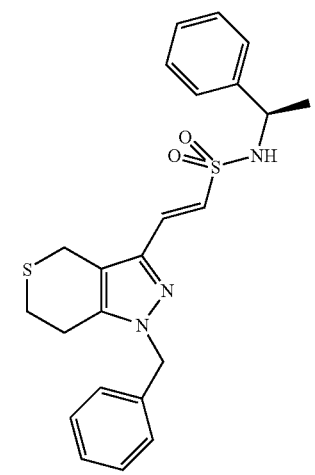
Cpd 22
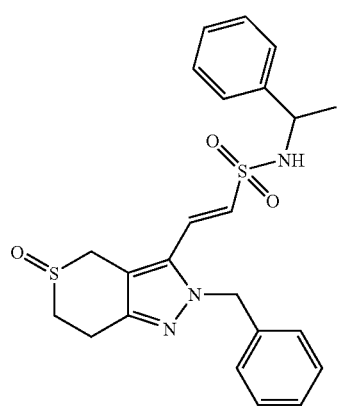
Cpd 40
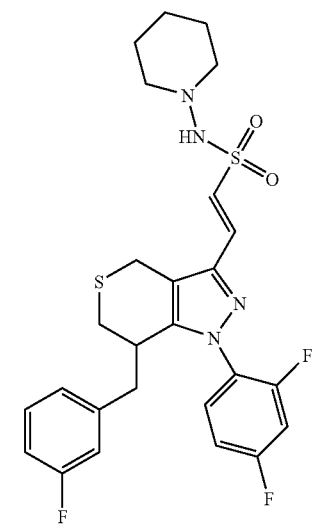
-continued
Cpd 42
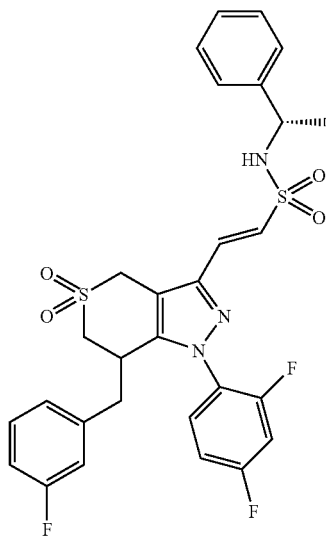
Cpd 44
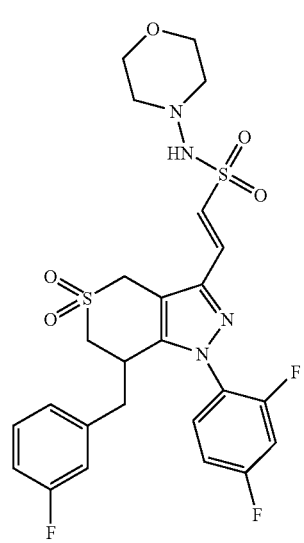
Cpd 48
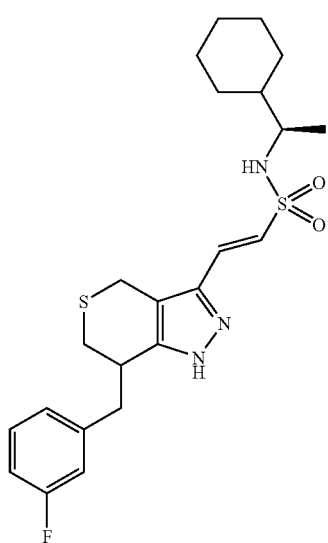

Cpd 49

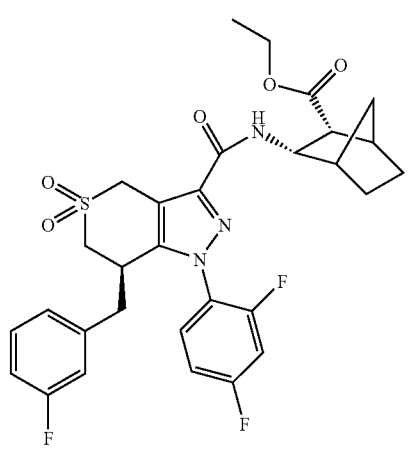

Cpd 81

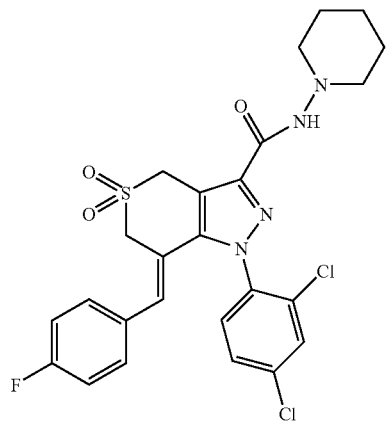

Cpd 54

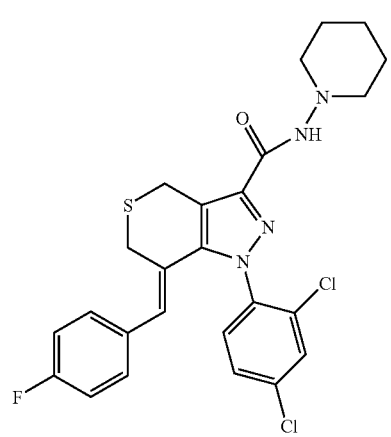

Cpd 92

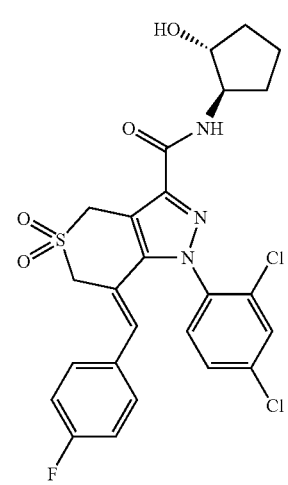 and

Cpd 124

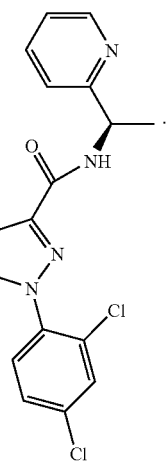

Cpd 67

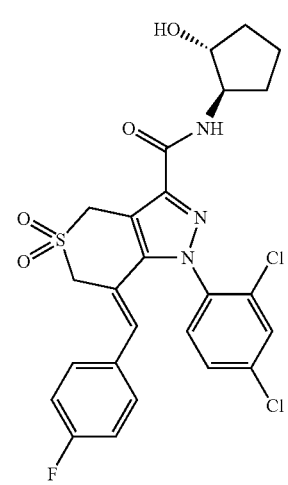

The present invention is directed to a method for treating, ameliorating or preventing a CB receptor mediated syndrome, disorder or disease in a subject in need thereof comprising the step of administering to the subject an effective amount of a compound of Formula (I) or prodrug, metabolite, or composition thereof.

The present invention is directed to a method for treating, ameliorating or preventing a CB receptor mediated syndrome, disorder or disease in a subject in need thereof comprising the step of administering to the subject an effective amount of a compound of Formulae (Ia)-(If) or prodrug, metabolite, or composition thereof.

The present invention is directed to a method for treating, ameliorating or preventing a CB receptor mediated syndrome, disorder or disease in a subject in need thereof comprising the step of administering to the subject a combination product and/or therapy comprising an effective amount of a compound of Formulae (I)-(If) and a therapeutic agent.

Therapeutic agents contemplated for use in a combination product and/or therapy of the present invention include an anticonvulsant (such as topiramate, analogs of topiramate, carbamazepine, valproic acid, lamotrigine, gabapentin, phenyloin and the like and mixtures or pharmaceutically acceptable salts thereof) or a contraceptive agent (such as progestin-only contraceptives and contraceptives that include both a progestin component and an estrogen component).

The invention further includes a pharmaceutical composition wherein the contraceptive is an oral contraceptive, and wherein the contraceptive optionally includes a folic acid component.

The invention also includes a method of contraception in a subject comprising administering to the subject a composition, wherein the composition comprises a contraceptive and a CB1 receptor inverse-agonist or antagonist compound of Formulae (I)-(If), and wherein the composition reduces the urge to smoke in the subject and/or assists the subject in losing weight.

The present invention is also directed to a method for treating, ameliorating or preventing a CB receptor mediated syndrome, disorder or disease in a subject in need thereof wherein the syndrome, disorder or disease is related to appetite, metabolism, diabetes, glaucoma-associated intraocular pressure, social and mood disorders, seizures, substance abuse, learning, cognition or memory, organ contraction or muscle spasm, bowel disorders, respiratory disorders, locomotor activity or movement disorders, immune and inflammation disorders, unregulated cell growth, pain management, neuroprotection and the like.

Chemistry Definitions and Pharmaceutical Forms

When any variable (e.g., aryl, heterocyclyl, $R_1$, $R_2$, etc.) occurs more than once in a substituent list, its definition on each occurrence is independent of any other occurrence.

Bond lines drawn into a ring system from a substituent variable (such as $R_6$, $R_{16}$, etc.) indicate that the substituent may be attached to any of the substitutable ring atoms. If the ring system is polycyclic, the substituent may be attached to any of the suitable atoms on the ring into which the bond line is drawn.

As used herein, the following terms are intended to have the following definitions.

"Alkyl" means a saturated aliphatic branched or straight-chain monovalent hydrocarbon radical substituent or alkyldiyl linking group having a specified number of carbon atoms, wherein the alkyl radical substituent is derived by the removal of one hydrogen atom from a carbon atom and the alkyldiyl linking group is derived by the removal of one hydrogen atom from each of two carbon atoms in the chain. The term "$C_{1-8}$ alkyl" means a radical having from 1-8 carbon atoms in a linear or branched arrangement. "$C_{1-6}$ alkyl" includes methyl, ethyl, propyl, butyl, pentyl, and hexyl. Alkyl and alkyldiyl radicals may be attached to a core molecule via a terminal carbon atom or via a carbon atom within the chain. Similarly, substituent variables may be attached to an alkyl or alkyldiyl radical when allowed by available valences.

"Alkoxy" means an alkyl radical attached through an oxygen linking atom. "$C_{1-4}$ alkoxy" includes the radicals methoxy, ethoxy, propoxy, and butoxy. An alkoxy radical may be attached to a core molecule and further substituted where indicated.

"Cycloalkyl" means a monovalent saturated or partially unsaturated cyclic ring system radical. Cycloalkyl ring systems include cyclopropyl, cyclobutyl, cyclopentyl, cyclohexyl, cycloheptyl, cyclooctyl, adamantanyl and the like.

"Aryl" means an monovalent aromatic cyclic ring system radical. Aryl ring systems include phenyl, naphthalenyl, fluorenyl, indenyl, azulenyl, anthracenyl and the like.

"Hetero," when used as a prefix for a ring system, refers to the replacement of at least one carbon atom member in the ring system with a heteroatom selected from N, S, O, or P. A hetero ring may have 1, 2, 3, or 4 carbon atom members replaced by a nitrogen atom. Alternatively, a ring may have 0, 1, 2, or 3 nitrogen atom members and 1 oxygen or sulfur atom member. Alternatively, up to two adjacent ring members may be heteroatoms; wherein 1 heteroatom is nitrogen and the other heteroatom is selected from N, S, or O.

"Heterocyclyl" means a "hetero" ring system radical having a cycloalkyl ring as the core molecule. Heterocyclyl ring systems include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydropyranyl, tetrahydro-pyridazinyl, 1,3-benzodioxolyl, 2,3-dihydro-1,4-benzodioxinyl and the like.

"Heteroaryl" means a monovalent heteroaromatic ring system radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, azaindolyl, isoindolyl, benzo[b]furyl, benzo[b]thienyl, indazolyl, azaindazolyl, benzimidazolyl, benzthiazolyl, benzoxazolyl, benzisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like.

The term "benzo-fused" refers to a bicyclic fused ring system radical formed by a monocyclic radical fused with a benzene ring; the benzo-fused radical may be attached to a core molecule via either ring of the bicyclic system.

The term "benzo-fused cycloalkyl" refers to a bicyclic fused ring system radical wherein a cycloalkyl ring is fused with a benzene ring. Benzo-fused cycloalkyl ring systems include indanyl, 1,2,3,4-tetrahydro-naphthalenyl, 5,6,7,8-tetrahydro-naphthalenyl, 6,7,8,9-tetrahydro-5H-benzocycloheptenyl, 5,6,7,8,9,10-hexahydro-benzocyclooctenyl and the like.

"Substituted" refers to a molecule in which one or more hydrogen atoms have been replaced with one or more substituent variables up to that amount allowed by the available valences.

"Dependently selected" refers to one or more substituent variables that are specified in an indicated combination for substitution in a core molecule (e.g., variables that refer to groups of substituents appearing in a tabular list of compounds).

In general, IUPAC nomenclature rules are used herein.

Certain compounds of Formula (I) may exist in various stereoisomeric or tautomeric forms. The invention encompasses all such CB receptor modulating compounds, including active compounds in the form of essentially pure enantiomers, racemic mixtures, and tautomers.

The compounds of the invention may be present in the form of pharmaceutically acceptable salts. For use in medicines, the salts of the compounds of this invention refer to non-toxic "pharmaceutically acceptable salts." FDA-approved pharmaceutically acceptable salt forms include pharmaceutically acceptable acidic/anionic or basic/cationic salts.

Pharmaceutically acceptable acidic/anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

The anionic salt form of a compound of the invention includes an anionic salt selected from the acetate, bromide, camsylate, chloride, edisylate, fumarate, hydrobromide, hydrochloride, iodide, isethionate, lactate, mesylate, napsylate, salicylate, sulfate, and tosylate salts.

During any of the processes for preparation of the compounds of the invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "stereoisomer" means isomers of identical constitution that differ in the spatial arrangement of their atoms. Enantiomers and diastereomers are stereoisomers wherein an asymmetrically substituted carbon atom acts as a chiral center. The term "chiral" means a molecule that is not superimposable on its mirror image, implying the absence of an axis and a plane or center of symmetry. The term "enantiomer" means one of a pair of molecular species that are mirror images of each other and are not superimposable. The term "diastereomer" means stereoisomers that are not related as mirror images. The symbol "*" in a structural formula represents the presence of a chiral carbon center. The symbols "R" and "S" represent the configuration of substituents around a chiral carbon atom(s). The symbols "R*" and "S*" denote the relative configurations of substituents around a chiral carbon atom(s).

The term "racemate" or "racemic mixture" means a compound of equimolar quantities of two enantiomeric species, wherein the compound is devoid of optical activity. The term "optical activity" means the degree to which a chiral molecule or non-racemic mixture of chiral molecules rotates the plane of polarized light.

"Geometric isomer" means isomers that differ in the orientation of substituent atoms in relationship to a carbon-carbon double bond, to a cycloalkyl ring, or to a bridged bicyclic system. Substituent atoms (other than H) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

The isomeric descriptors ("R," "S," "S*," "R*," "E," and "Z") indicate atom configurations relative to a core molecule and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the invention may have one or more polymorph or amorphous crystalline forms. Said forms are included in the scope of the invention. In addition, some of the compounds may form solvates with water (i.e., hydrates) or common organic solvents. Said solvates are encompassed within the scope of this invention.

Therapeutic Use

The compounds of the present invention are useful in a method for treating, ameliorating or preventing a CB mediated syndrome, disorder or disease in a subject in need thereof comprising the step of administering to the subject an effective amount of a compound of Formula (I).

CB receptors belong to the G-protein-coupled receptor (GCPR) family, a receptor super-family with a distinctive pattern of seven transmembrane domains, which inhibits N-type calcium channels and/or adenylate cyclase to inhibit Q-type calcium channels.

CB1 receptors are present in the CNS, predominately expressed in brain regions associated with memory and movement such as the hippocampus (memory storage), cerebellum (coordination of motor function, posture and balance), basal ganglia (movement control), hypothalamus (thermal regulation, neuroendocrine release, appetite), spinal cord (nociception), cerebral cortex (emesis) and periphery regions such as lymphoid organs (cell mediated and innate immunity), vascular smooth muscle cells (blood pressure), gastrointestinal tract (duodenum, ileum and myenteric plexus for emesis control), lung smooth muscle cells (bronchodilation), eye ciliary body (intraocular pressure).

CB2 receptors appear to be primarily expressed peripherally in lymphoid tissue (cell mediated and innate immunity), peripheral nerve terminals (peripheral nervous system), spleen immune cells (immune system modulation) and retina (intraocular pressure) and in the CNS in cerebellar granule cell mRNA (coordination of motor function). Pharmacological and physiological evidence also suggests that there may be other CB receptor subtypes that have yet to be cloned and characterized.

There are potential areas of clinical application where activation or inhibition of a CB receptor appears to mediate various syndromes, disorders or diseases. Thus, CB receptor modulators, including the compounds of Formula (I), are useful for treating, ameliorating or preventing a CB receptor mediated syndrome, disorder or disease including, but not limited to, controlling or regulating appetite, metabolism, obesity, diabetes, glaucoma-associated intraocular pressure, social and mood disorders, seizure-related disorders, substance abuse disorders, learning, cognition and/or memory disorders, bowel disorders, respiratory disorders, locomotor activity disorders, movement disorders, immune disorders, inflammation disorders, gastrointestinal disorders, organ contraction, muscle spasm, cell growth, pain or management thereof or for use as a neuroprotective agent and the like.

The present invention includes CB receptor modulators useful for treating, ameliorating or preventing a CB receptor mediated syndrome, disorder or disease. The usefulness of a compound of Formula (I) as a CB receptor modulator can be determined according to the methods disclosed herein. The scope of such use includes treating, ameliorating or preventing a plurality of CB receptor mediated syndromes, disorders or diseases.

A compound of Formulae (I)-(If) for use as a CB receptor modulator includes a compound having a mean inhibition constant ($IC_{50}$) for CB binding of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of Formulae (I)-(If) for use as a CB receptor modulator of the invention includes a compound having a CB1 agonist $IC_{50}$ for CB1 agonist activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of Formulae (I)-(If) for use as a CB receptor modulator of the invention includes a compound having a CB1 antagonist $IC_{50}$ for CB1 antagonist activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of Formulae (I)-(If) for use as a CB receptor modulator of the invention includes a compound having a CB1 inverse-agonist $IC_{50}$ for CB1 inverse-agonist activity of between about 5 µM to about 0.01 nM; between about 1 µM to about 0.01 nM; between about 800 nM to about 0.01 nM; between about 200 nM to about 0.01 nM to about 0.01 nM; between about 80 nM to about 0.01 nM; between about 20 nM to about 0.01 nM; between about 10 nM to about 0.1 nM; or about 1 nM.

A compound of Formulae (I)-(If) for use as a CB receptor modulator of the invention includes a compound having a CB2 agonist $IC_{50}$ for CB2 agonist activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of Formulae (I)-(If) for use as a CB receptor modulator of the invention includes a compound having a CB2 antagonist $IC_{50}$ for CB2 antagonist activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

A compound of Formulae (I)-(If) for use as a CB receptor modulator of the invention includes a compound having a CB2 inverse-agonist $IC_{50}$ for CB2 inverse-agonist activity of between about 5 µM to about 0.01 nM; between about 1 µM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 1 nM.

The present invention is further directed to a method for treating, ameliorating or preventing a CB receptor mediated syndrome, disorder or disease in a subject in need thereof comprising the step of administering to the subject an effective amount of a compound of Formula (I).

The present invention is also directed to a method for treating, ameliorating or preventing a CB receptor mediated syndrome, disorder or disease in a subject in need thereof wherein the syndrome, disorder or disease is related to an appetite, metabolism, obesity, diabetes, glaucoma-associated intraocular pressure, social, mood, seizure, substance abuse, learning, cognition, memory, gastrointestinal, organ contraction, muscle spasm, respiratory, locomotor activity, movement, immune, inflammation or an unregulated cell growth or syndrome, disorder or disease or for use in pain management or as a neuroprotection agent for treating, ameliorating or preventing a CB receptor mediated syndrome, disorder or disease.

The present invention is further directed to a method for treating, ameliorating or preventing a CB receptor mediated syndrome, disorder or disease in a subject in need thereof comprising the step of administering to the subject an effective amount of a compound of Formula (I).

"CB receptor" means any one of the known or heretofore unknown subtypes of the class of CB receptors that may be bound by a compound of the present invention, such as the CB1 or CB2 receptor. The term "modulator" further refers to the use of a compound of the invention as a CB receptor agonist, antagonist or inverse-agonist.

"Subject" means a patient, which may be an animal, preferably a mammal, most preferably a human, who has a disease or disorder or is at risk of (or susceptible to) developing a CB receptor mediated syndrome, disorder or disease.

"Administering," with respect to the methods of the invention, means a method for treating, ameliorating or preventing a syndrome, disorder or disease as described herein with a compound of the invention or prodrug, metabolite or composition thereof. Such methods include administering an effective amount thereof at different times during the course of a therapy or concurrently in a combination form. Prophylactic administration can occur prior to the manifestation of symptoms characteristic of a CB receptor mediated syndrome, disorder or disease such that the syndrome, disorder or disease is prevented or otherwise delayed in its development. Therapeutic administration occurs once symptoms characteristic of a CB receptor mediated syndrome, disorder or disease have manifested such that the syndrome, disorder or disease is treated, ameliorated or otherwise delayed in its progression. The methods of the invention are to be understood as embracing all known therapeutic treatment regimens.

"Prodrug" means a pharmaceutically acceptable form of a functional derivative of a compound of the invention (or a salt thereof), wherein the prodrug may be: 1) a relatively active precursor which converts in vivo to an active prodrug component; 2) a relatively inactive precursor which converts in vivo to an active prodrug component; or 3) a relatively less active component of the compound that contributes to therapeutic biological activity after becoming available in vivo (i.e., as a metabolite). Conventional procedures for the selection and preparation of suitable prodrug derivatives are described, for example, in "Design of Prodrugs", ed. H. Bundgaard, Elsevier, 1985.

"Metabolite" means a pharmaceutically acceptable form of a metabolic derivative of a compound of the invention (or a salt thereof), wherein the derivative is a relatively less active component of the compound that contributes to therapeutic biological activity after becoming available in vivo.

"Effective amount" means that amount of a compound of Formula (I) that is effective in an animal or human to treat, ameliorate or prevent the symptoms of the CB receptor mediated syndrome, disorder or disease being treated. The effective amount of a compound of the invention is from about 0.001 mg/kg/day to about 300 mg/kg/day.

"CB receptor mediated syndrome, disorder or disease" refers to syndromes, disorders or diseases associated with a biological response mediated by a CB receptor such that there is discomfort or decreased life expectancy to the organism.

CB receptor mediated syndromes, disorders or diseases can occur in both animals and humans and include a syndrome, disorder or disease related to an appetite, metabolism, obesity, diabetes, glaucoma-associated intraocular pressure, social, mood, seizure, substance abuse, learning, cognition, memory, gastrointestinal, organ contraction, muscle spasm, respiratory, locomotor activity, movement, immune, inflammation, cell growth, pain or neurodegenerative syndrome, disorder or disease.

Appetite related syndromes, disorders or diseases include obesity, overweight condition, anorexia, bulimia, cachexia, dysregulated appetite and the like.

Metabolism related syndromes, disorders or diseases include metabolic syndrome, dyslipidemia, elevated blood pressure, diabetes, insulin sensitivity or resistance, hyperinsulinemia, hypercholesterolemia, hyperlipidemias, hypertriglyceridemias, atherosclerosis, hepatomegaly, steatosis, abnormal alanine aminotransferase levels, inflammation, atherosclerosis and the like.

Obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution and the like.

Diabetes related syndromes, disorders or diseases include glucose dysregulation, insulin resistance, glucose intolerance, hyperinsulinemia, dyslipidemia, hypertension, obesity and the like.

Type II diabetes mellitus (non-insulin-dependent diabetes mellitus) is a metabolic disorder (i.e., a metabolism related syndrome, disorder or disease) in which glucose dysregulation and insulin resistance results in chronic, long-term medical complications for both adolescents and adults affecting the eyes, kidneys, nerves and blood vessels and can lead to blindness, end-stage renal disease, myocardial infarction or limb amputation and the like. Glucose dysregulation includes the inability to make sufficient insulin (abnormal insulin secretion) and the inability to effectively use insulin (resistance to insulin action in target organs and tissues). Individuals suffering from Type II diabetes mellitus have a relative insulin deficiency. That is, in such individuals, plasma insulin levels are normal to high in absolute terms, although they are lower than predicted for the level of plasma glucose that is present.

Type II diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension. These micro- and macro-vascular complications can lead to blindness, end-stage renal disease, limb amputation and myocardial infarction.

Insulin Resistance Syndrome (IRS) (also referred to as Syndrome X, Metabolic Syndrome or Metabolic Syndrome X) is a disorder that presents risk factors for the development of Type II diabetes and cardiovascular disease including glucose intolerance, hyperinsulinemia, insulin resistance, dyslipidemia (e.g. high triglycerides, low HDL-cholesterol and the like), hypertension and obesity.

Social or mood related syndromes, disorders or diseases include depression, anxiety, psychosis, social affective disorders or cognitive disorders and the like.

Substance abuse related syndromes, disorders or diseases include drug abuse, drug withdrawal, alcohol abuse, alcohol withdrawal, nicotine withdrawal, cocaine abuse, cocaine withdrawal, heroin abuse, heroin withdrawal and the like.

Learning, cognition or memory related syndromes, disorders or diseases include memory loss or impairment as a result of age, disease, side effects of medications (adverse events) and the like.

Muscle spasm syndromes, disorders or diseases include multiple sclerosis, cerebral palsy and the like.

Locomotor activity and movement syndromes, disorders or diseases include stroke, Parkinson's disease, multiple sclerosis, epilepsy and the like.

Bowel related syndromes, disorders or diseases include bowel dysmotility associated disorders (either accompanied by pain, diarrhea or constipation or without), irritable bowel syndrome (and other forms of bowel dysmotility and the like), inflammatory bowel diseases (such as ulcerative colitis, Crohn's disease and the like) and celiac disease.

Respiratory related syndromes, disorders or diseases include chronic pulmonary obstructive disorder, emphysema, asthma, bronchitis and the like.

Immune or inflammation related syndromes, disorders or diseases include allergy, rheumatoid arthritis, dermatitis, autoimmune disease, immunodeficiency, chronic neuropathic pain and the like.

Cell growth related syndromes, disorders or diseases include dysregulated mammalian cell proliferation, breast cancer cell proliferation, prostate cancer cell proliferation and the like.

Pain related syndromes, disorders or diseases include central and peripheral pathway mediated pain, bone and joint pain, migraine headache associated pain, cancer pain, menstrual cramps, labor pain and the like.

Neurodegenerative related syndromes, disorders or diseases include Parkinson's Disease, multiple sclerosis, epilepsy, ischemia or secondary biochemical injury collateral to traumatic head or brain injury, brain inflammation, eye injury or stroke and the like.

An example of the invention includes a method for treating, ameliorating or preventing a CB receptor mediated metabolism related syndrome, disorder or disease, an appetite related syndrome, disorder or disease, a diabetes related syndrome, disorder or disease, an obesity related syndrome, disorder or disease or a learning, cognition or memory related syndrome, disorder or disease in a subject in need thereof comprising administering to the subject an effective amount of a compound of the present invention or composition thereof.

An example of the invention includes a method for treating, ameliorating or preventing a CB receptor agonist mediated syndrome, disorder or disease in a subject in need thereof comprising administering to the subject an effective amount of a compound of Formula (I).

An example of the invention includes a method for treating, ameliorating or preventing a CB receptor inverse-agonist mediated syndrome, disorder or disease in a subject in need thereof comprising administering to the subject an effective amount of a compound of Formula (I).

An example of the invention includes a method for treating, ameliorating or preventing a CB receptor antagonist mediated syndrome, disorder or disease in a subject in need thereof comprising administering to the subject an effective amount of a compound of Formula (I).

An example of the invention includes a method for treating, ameliorating or preventing a CB1 receptor agonist mediated syndrome, disorder or disease in a subject in need thereof comprising administering to the subject an effective amount of a compound of Formula (I).

An example of the invention includes a method for treating, ameliorating or preventing a CB1 receptor antagonist mediated syndrome, disorder or disease in a subject in need thereof comprising administering to the subject an effective amount of a compound of Formula (I).

An example of the invention includes a method for treating, ameliorating or preventing a CB1 receptor inverse-agonist mediated syndrome, disorder or disease in a subject in need thereof comprising administering to the subject an effective amount of a compound of Formula (I).

An example of the invention includes a method for treating, ameliorating or preventing a CB1 receptor inverse-agonist mediated appetite related syndrome, disorder or disease in a subject in need thereof, comprising administering to the subject an effective amount of a compound of Formula (I), wherein appetite related syndromes, disorders or diseases include obesity, overweight condition, anorexia, bulimia, cachexia, dysregulated appetite and the like.

An example of the invention includes a method for treating, ameliorating or preventing a CB1 receptor inverse-agonist mediated obesity related syndrome, disorder or disease in a subject in need thereof, comprising administering to the subject an effective amount of a compound of Formula (I), wherein obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution and the like.

An example of the invention includes a method for treating, ameliorating or preventing a CB1 receptor inverse-agonist mediated metabolism related syndrome, disorder or disease in a subject in need thereof, comprising administering to the subject an effective amount of a compound of Formula (I), wherein metabolism related syndromes, disorders or diseases include metabolic syndrome, dyslipidemia, elevated blood pressure, diabetes, insulin sensitivity or resistance, hyperinsulinemia, hypercholesterolemia, hyperlipidemias, hypertriglyceridemias, atherosclerosis, hepatomegaly, steatosis, abnormal alanine aminotransferase levels, inflammation, atherosclerosis and the like.

An example of the invention includes a method for treating, ameliorating or preventing a CB2 receptor agonist mediated syndrome, disorder or disease in a subject in need thereof comprising administering to the subject an effective amount of a compound of Formula (I).

An example of the invention includes a method for treating, ameliorating or preventing a CB2 receptor antagonist mediated syndrome, disorder or disease in a subject in need thereof comprising administering to the subject an effective amount of a compound of Formula (I).

An example of the invention includes a method for treating, ameliorating or preventing a CB2 receptor inverse-agonist mediated syndrome, disorder or disease in a subject in need thereof comprising administering to the subject an effective amount of a compound of Formula (I).

The present invention further includes a method for use of an instant compound in a combination product and/or therapy for treating, ameliorating or preventing a CB receptor mediated syndrome, disorder or disease related to an appetite, metabolism, obesity, diabetes, glaucoma-associated intraocular pressure, social, mood, seizure, substance abuse, learning, cognition, memory, gastrointestinal, organ contraction, muscle spasm, respiratory, locomotor activity, movement, immune, inflammation, cell growth, pain or neurodegenerative syndrome, disorder or disease in a subject in need thereof comprising administering to the subject an effective amount of the combination product, wherein the product is one or more of a compound of Formulae (I)-(If) combined with one or more therapeutic agents.

Unless specified otherwise, "combination product and/or therapy" means a pharmaceutical composition comprising a compound of Formulae (I)-(If) in combination with one or more therapeutic agents. As those skilled in the art will appreciate, the dosages of the compound and the one or more therapeutic agents are adjusted when combined to achieve an effective amount. The effective amounts of the compound and agent may be independently optimized and combined to achieve a synergistic result whereby the pathology is reduced more than it would be if either the compound or agent were used alone.

With respect to the method for use of a combination product and/or therapy for treating, ameliorating or preventing a CB receptor mediated syndrome, disorder or disease, the term "effective amount" means that amount of the compound and agent taken together so that the combined effect treats, ameliorates or prevents the symptoms of the syndrome, disorder or disease.

With respect to the method for use of a combination product and/or therapy, the term "administering," is also intended to include co-administering an effective amount of the compound and the agent, sequential administration of the compound and the agent, administration of a single composition containing of the compound and the agent or simultaneous administration of separate, divided compositions containing the compound and the agent. The methods of the invention are therefore further to be understood as embracing all such regimes of simultaneous or alternating treatment regimens.

Therapeutic agents contemplated for use in a combination product and/or therapies of the present invention include anticonvulsants or contraceptive agents or composition(s) thereof. It should be understood that contraceptive agents suitable for use in a combination product and/or therapy are not limited to oral contraceptives, but also include other commonly available contraceptives such as those that are administered transdermally, by injection or via implant.

For example, the effective amount of a combination product and/or therapy comprising administration of a compound of Formula (I) and an anticonvulsant would be the amount of the compound of Formula (I) and the amount of the anticonvulsant that when taken together or sequentially have a combined effect that is therapeutically or prophylactically effective.

Further, it will be recognized by one skilled in the art that in the case of combination product and/or therapy with a therapeutically or prophylactically effective amount, as in the example above, the amount of the compound of Formula (I) and/or the amount of the anticonvulsant individually may or may not be effective.

Wherein the present invention is directed to the administration of a combination product and/or therapy, the instant compound and the anticonvulsant or contraceptive agent may be co-administered by any suitable means, simultaneously, sequentially or in a single pharmaceutical composition.

Where the instant compound(s) and the anticonvulsant or contraceptive agent components are administered separately, the number of dosages of each compound(s) given per day, may not necessarily be the same, e.g. where one compound may have a greater duration of activity, and will therefore, be administered less frequently.

The compound(s) and the anticonvulsant(s) or contraceptive agent(s) of the combination product and/or therapy may be administered via the same or different routes of administration.

An example of the invention includes a method for treating, ameliorating or preventing a CB receptor mediated syndrome, disorder or disease in a subject in need thereof comprising administering to the subject an effective amount of a combination product and/or therapy, wherein the product and/or therapy is one or more of a compound of Formula (I) combined with one or more anticonvulsants.

An example of the invention includes a method for treating, ameliorating or preventing a CB receptor agonist mediated syndrome, disorder or disease in a subject in need thereof comprising administering to the subject an effective amount of a combination product and/or therapy, wherein the product and/or therapy is one or more of a compound of Formula (I) combined with one or more anticonvulsants.

An example of the invention includes a method for treating, ameliorating or preventing a CB receptor antagonist mediated syndrome, disorder or disease in a subject in need thereof comprising administering to the subject an effective amount of a combination product and/or therapy, wherein the product and/or therapy is one or more of a compound of Formula (I) combined with one or more anticonvulsants.

An example of the invention includes a method for treating, ameliorating or preventing a CB receptor inverse-agonist mediated syndrome, disorder or disease in a subject in need thereof comprising administering to the subject an effective amount of a combination product and/or therapy, wherein the product and/or therapy is one or more of a compound of Formula (I) combined with one or more anticonvulsants.

An example of the invention includes a method for treating, ameliorating or preventing a CB receptor mediated syndrome, disorder or disease in a subject in need thereof comprising administering to the subject an effective amount of a combination product and/or therapy, wherein the product and/or therapy is one or more of a compound of Formula (I) combined with one or more contraceptives.

An example of the invention includes a method for treating, ameliorating or preventing a CB receptor agonist mediated syndrome, disorder or disease in a subject in need thereof comprising administering to the subject an effective amount of a combination product and/or therapy, wherein the product and/or therapy is one or more of a compound of Formula (I) combined with one or more contraceptives.

An example of the invention includes a method for treating, ameliorating or preventing a CB receptor antagonist mediated syndrome, disorder or disease in a subject in need thereof comprising administering to the subject an effective amount of a combination product and/or therapy, wherein the product and/or therapy is one or more of a compound of Formula (I) combined with one or more contraceptives.

An example of the invention includes a method for treating, ameliorating or preventing a CB receptor inverse-agonist mediated syndrome, disorder or disease in a subject in need thereof comprising administering to the subject an effective amount of a combination product and/or therapy, wherein the product and/or therapy is one or more of a compound of Formula (I) combined with one or more contraceptives.

An example of the invention includes a method for treating, ameliorating or preventing a CB1 receptor agonist mediated syndrome, disorder or disease in a subject in need thereof comprising administering to the subject an effective amount of a combination product and/or therapy, wherein the product and/or therapy is one or more of a compound of Formula (I) combined with one or more anticonvulsants.

An example of the invention includes a method for treating, ameliorating or preventing a CB1 receptor antagonist mediated syndrome, disorder or disease in a subject in need thereof comprising administering to the subject an effective amount of a combination product and/or therapy, wherein the product and/or therapy is one or more of a compound of Formula (I) combined with one or more anticonvulsants.

An example of the invention includes a method for treating, ameliorating or preventing a CB1 receptor inverse-agonist mediated syndrome, disorder or disease in a subject in need thereof comprising administering to the subject an effective amount of a combination product and/or therapy, wherein the product and/or therapy is one or more of a compound of Formula (I) combined with one or more anticonvulsants.

An example of the invention includes a method for treating, ameliorating or preventing a CB1 receptor agonist mediated syndrome, disorder or disease in a subject in need thereof comprising administering to the subject an effective amount of a combination product and/or therapy, wherein the product and/or therapy is one or more of a compound of Formula (I) combined with one or more contraceptives.

An example of the invention includes a method for treating, ameliorating or preventing a CB1 receptor antagonist mediated syndrome, disorder or disease in a subject in need thereof comprising administering to the subject an effective amount of a combination product and/or therapy, wherein the product and/or therapy is one or more of a compound of Formula (I) combined with one or more contraceptives.

An example of the invention includes a method for treating, ameliorating or preventing a CB1 receptor inverse-agonist mediated syndrome, disorder or disease in a subject in need thereof comprising administering to the subject an effective amount of a combination product and/or therapy, wherein the product and/or therapy is one or more of a compound of Formula (I) combined with one or more contraceptives.

An example of the invention includes a method for treating, ameliorating or preventing a CB1 receptor inverse-agonist mediated appetite related syndrome, disorder or disease in a subject in need thereof comprising administering to the subject an effective amount of a combination product and/or therapy, wherein the product and/or therapy is one or more of a compound of Formula (I) combined with one or more anticonvulsants.

An example of the invention includes a method for treating, ameliorating or preventing a CB1 receptor inverse-agonist mediated obesity related syndrome, disorder or disease in a subject in need thereof comprising administering to the subject an effective amount of a combination product and/or therapy, wherein the product and/or therapy is one or more of a compound of Formula (I) combined with one or more anticonvulsants.

Appetite related syndromes, disorders or diseases include obesity, overweight condition, anorexia, bulimia, cachexia, dysregulated appetite and the like.

Obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution and the like.

An example of the invention includes a method for treating, ameliorating or preventing a CB1 receptor inverse-agonist mediated metabolism related syndrome, disorder or disease in a subject in need thereof comprising administering to the subject a therapeutically or prophylactically effective amount of a compound of the present invention in a combination product and/or therapy with an anticonvulsant or composition thereof.

Metabolism related syndromes, disorders or diseases include metabolic syndrome, dyslipidemia, elevated blood pressure, diabetes, insulin sensitivity or resistance, hyperinsulinemia, hypercholesterolemia, hyperlipidemias, hypertriglyceridemias, atherosclerosis, hepatomegaly, steatosis, abnormal alanine aminotransferase levels, inflammation, atherosclerosis and the like.

An example of the invention includes a method for treating, ameliorating or preventing a CB2 receptor agonist mediated syndrome, disorder or disease in a subject in need thereof comprising administering to the subject a therapeutically or prophylactically effective amount of a compound of the present invention in a combination product and/or therapy with an anticonvulsant or composition thereof.

An example of the invention includes a method for treating, ameliorating or preventing a CB2 receptor antagonist mediated syndrome, disorder or disease in a subject in need thereof comprising administering to the subject a therapeutically or prophylactically effective amount of a compound of the present invention in a combination product and/or therapy with an anticonvulsant or composition thereof.

An example of the invention includes a method for treating, ameliorating or preventing a CB2 receptor inverse-agonist mediated syndrome, disorder or disease in a subject in need thereof comprising administering to the subject a therapeutically or prophylactically effective amount of a compound of the present invention in a combination product and/or therapy with an anticonvulsant or composition thereof.

An example of the invention includes a method for treating, ameliorating or preventing a CB receptor mediated syndrome, disorder or disease in a subject in need thereof comprising administering to the subject an effective amount of a combination product and/or therapy, wherein the product and/or therapy is one or more of a compound of Formula (I) combined with one or more anticonvulsants selected from topiramate, analogs of topiramate, carbamazepine, valproic acid, lamotrigine, gabapentin or phenyloin or pharmaceutically acceptable forms and mixtures thereof.

An example of the invention includes a method for treating, ameliorating or preventing a CB1 receptor mediated syndrome, disorder or disease in a subject in need thereof comprising administering to the subject an effective amount of a combination product and/or therapy, wherein the product and/or therapy is one or more of a compound of Formula (I) combined with one or more anticonvulsants selected from topiramate, analogs of topiramate, carbamazepine, valproic acid, lamotrigine, gabapentin or phenyloin or pharmaceutically acceptable forms and mixtures thereof.

An example of the invention includes a method for treating, ameliorating or preventing a CB2 receptor mediated syndrome, disorder or disease in a subject in need thereof comprising administering to the subject an effective amount of a combination product and/or therapy, wherein the product and/or therapy is one or more of a compound of Formula (I) combined with one or more anticonvulsants selected from topiramate, analogs of topiramate, carbamazepine, valproic acid, lamotrigine, gabapentin or phenyloin or pharmaceutically acceptable forms and mixtures thereof.

"Topiramate" means 2,3:4,5-bis-O-(1-methylethylidene)-β-D-fructopyranose sulfamate, an anticonvulsant globally marketed for the treatment of seizures in patients with simple and complex partial epilepsy, for the treatment of seizures in patients with primary or secondary generalized seizures and for the treatment of a variety of central and peripheral nervous system syndromes, disorders or diseases.

Topiramate is currently available for oral administration in round tablets containing 25 mg, 100 mg or 200 mg of active agent, and as 15 mg and 25 mg sprinkle capsules for oral administration as whole capsules or opened and sprinkled onto soft food. U.S. Pat. No. 4,513,006, incorporated herein by reference, discloses topiramate and analogs of topiramate, their manufacture and use for treating epilepsy. Additionally, topiramate may also be made by the process disclosed in U.S. Pat. Nos. 5,242,942 and 5,384,327, which are incorporated by reference herein.

"Analogs of topiramate", means sulfamate compounds of topiramate which are disclosed in U.S. Pat. No. 4,513,006 (see, e.g., column 1, lines 36-65), incorporated herein by reference.

An effective amount of topiramate (or analog of topiramate) for use in a combination product in a method of the present invention is in a range selected from about 10 to about 1000 mg once or twice daily, from about 10 to about 650 mg once or twice daily, or from about 15 to about 325 mg once or twice daily.

"Carbamazepine" means 5H-dibenz[b,f]azepine-5-carboxamide, an anticonvulsant and specific analgesic for trigeminal neuralgia, available for oral administration as chewable tablets of 100 mg, tablets of 200 mg, XR (extended release) tablets of 100, 200, and 400 mg, and as a suspension of 100 mg/5 mL (teaspoon); U.S. Pat. No. 2,948,718, herein incorporated by reference in its entirety, discloses carbamazepine and its methods of use.

An effective amount of carbamazepine for use in a combination product in a method of the present invention is in a range selected from about 200 to about 1200 mg daily, or about 400 mg daily.

"Valproic acid" means 2-propylpentanoic acid or dipropylacetic acid, an antiepileptic agent commercially available as soft elastic capsules containing 250 mg valproic acid, and as syrup containing the equivalent of 250 mg valproic acid per 5 mL as the sodium salt. Valproic acid and various pharmaceutically acceptable salts are disclosed in U.S. Pat. No. 4,699,927, which is incorporated by reference herein in its entirety.

An effective amount of valproic acid for use in a combination product in a method of the present invention is in a range selected from about 250 to about 2500 mg once daily, or about 1000 mg once daily.

"Lamotrigine" means 3,5-diamino-6-(2,3-dichlorophenyl)-1,2,4-triazine, an antiepileptic drug commercially available for oral administration as tablets containing 25 mg, 100 mg, 150 mg, and 200 mg of lamotrigine, and as chewable dispersible tablets containing 2 mg, 5 mg, or 25 mg of lamotrigine. Lamotrigine and its uses are disclosed in U.S. Pat. No. 4,486,354, incorporated by reference herein in its entirety.

An effective amount of lamotrigine for use in a combination product in a method of the present invention is in a range selected from about 50 to about 600 mg once or twice daily, from about 200 to about 400 mg once daily, or about 320 mg once daily.

"Gabapentin" means 1-(aminomethyl)cyclohexaneacetic acid, a commercially available adjunct drug for treatment of epilepsy and postherpetic neuralgia in adults containing 100 mg, 300 mg, and 400 mg of gabapentin, film-coated tablets containing 600 mg and 800 mg of gabapentin, and an oral solution containing 250 mg/5 mL of gabapentin. Gabapentin and its methods of use are described in U.S. Pat. Nos. 4,024,175 and 4,087,544, herein incorporated by reference in their entirety.

An effective amount of gabapentin for use in a combination product in a method of the present invention is in a range selected from about 300 to about 3600 mg once daily in two to three divided doses, from about 300 to about 1800 mg once daily, or about 900 mg once daily.

"Phenyloin sodium" means 5,5-diphenylhydantoin sodium salt, an anticonvulsant commercially available for oral administration as capsules containing 100 mg, 200 mg or 300 mg of phenyloin sodium.

An effective amount of phenyloin sodium for use in a combination product in a method of the present invention is in a range selected from about 100 to about 500 mg once daily, from about 300 to about 400 mg once daily, or about 300 mg once daily.

An example of the invention includes a method for treating, ameliorating or preventing a CB receptor mediated syndrome, disorder or disease in a subject in need thereof comprising administering to the subject an effective amount of a combination product and/or therapy, wherein the product and/or therapy is one or more of a compound of Formula (I) combined with one or more contraceptives or pharmaceutically acceptable forms and mixtures thereof.

An example of the invention includes a method for treating, ameliorating or preventing a CB1 receptor mediated syndrome, disorder or disease in a subject in need thereof comprising administering to the subject an effective amount of a combination product and/or therapy, wherein the product and/or therapy is one or more of a compound of Formula (I) combined with one or more contraceptives or pharmaceutically acceptable forms and mixtures thereof.

An example of the invention includes a method for treating, ameliorating or preventing a CB2 receptor mediated syndrome, disorder or disease in a subject in need thereof comprising administering to the subject an effective amount of a combination product and/or therapy, wherein the product and/or therapy is one or more of a compound of Formula (I) combined with one or more contraceptives or pharmaceutically acceptable forms and mixtures thereof.

Contraceptives suitable for use in a combination product and/or therapy include, for example, ORTHO CYCLEN®, ORTHO TRI-CYCLEN®, ORTHO TRI-CYCLEN LO®, and ORTHO EVRA®, all available from Ortho-McNeil Pharmaceutical, Inc., Raritan, N.J. It should also be understood that contraceptives suitable for use in the invention encompass those contraceptives that include a folic acid component.

Smoking and/or obesity have been identified as risk factors in women taking oral contraceptives. CB receptor antagonists and inverse agonists and, more particularly, CB1 receptor antagonists and inverse agonists have been found to be useful therapeutic agents for reducing the urge to smoke and for assisting patients with eating disorders to lose weight.

Accordingly, the invention further includes a method of reducing the risk factors associated with smoking and/or obesity for women taking contraceptives by co-administering with a contraceptive at least one of a CB1 receptor antagonist and/or CB1 receptor inverse-agonist compound of Formulae (I)-(If).

The use of such compounds or a pharmaceutical composition or medicament thereof is to reduce the desire to smoke and/or to assist in weight loss for patients taking contraceptives.

Pharmaceutical Compositions

The present invention includes a pharmaceutical composition or medicament comprising an admixture of a compound of the present invention and an optional pharmaceutically acceptable carrier.

The present invention includes a pharmaceutical composition or medicament comprising an admixture of two or more compounds of the present invention and an optional pharmaceutically acceptable carrier.

The present invention also includes a pharmaceutical composition or medicament comprising an admixture of a compound of Formula (I), a therapeutic agent and an optional pharmaceutically acceptable carrier.

Such pharmaceutical compositions are particularly useful for treating a subject suffering from a metabolism related syndrome, disorder or disease, an appetite related syndrome, disorder or disease, a diabetes related syndrome, disorder or disease, an obesity related syndrome, disorder or disease, or a learning, cognition or memory related syndrome, disorder or disease.

Pharmaceutical compositions of the invention may, alternatively or in addition to a compound of Formula (I), comprise a pharmaceutically acceptable salt of a compound of Formula (I) or a prodrug or pharmaceutically active metabolite of such a compound or salt in admixture with a pharmaceutically acceptable carrier.

"Composition" means a product comprising at least a compound of the invention and a pharmaceutically acceptable carrier or any such alternatives to a compound of the invention and a pharmaceutically acceptable carrier, as well as any product that results, directly or indirectly, from such combinations. The invention further comprises mixing one or more of the compounds of the invention and a pharmaceutically acceptable carrier; and, includes those compositions resulting from such a process. Contemplated processes include both traditional and modern pharmaceutical techniques.

"Medicament" means a product for use in treating, ameliorating or preventing a CB receptor mediated syndrome, disorder or disease.

"Pharmaceutically acceptable carrier" means molecular entities and compositions that are of sufficient purity and quality for use in the formulation of a composition of the invention and that, when appropriately administered to an animal or a human, do not produce an adverse, allergic, or other untoward reaction. Since both human and veterinary uses are included within the scope of the invention, a pharmaceutically acceptable formulation includes a composition or medicament for either human or veterinary use.

The composition may take a wide variety of forms to effectuate mode of administration including ocular, oral, sublingual, nasal (inhaled or insufflated), transdermal, rectal, vaginal, topical (with or without occlusion), intravenous (both bolus and infusion), and injection (intraperitoneally, subcutaneously, intramuscularly, intratumorally, or parenterally). Compounds may also be administrated directly to the nervous system including, but not limited to the intracerebral, intraventricular, intracerebroventricular, intrathecal, intracisternal, intraspinal and/or peri-spinal routes of administration by delivery via intracranial or intravertebral needles and/or catheters with or without pump devices.

The composition may be in a dosage unit such as a tablet, pill, capsule, syrup, elixir, emulsion, powder, granule, liposome, ion exchange resin, sterile ocular solution, or ocular delivery device (such as a contact lens and the like facilitating immediate release, timed release, or sustained release), solution or suspension (for parenteral or oral use), metered aerosol or liquid spray, drop, ampoule, auto-injector device, or suppository; for administration ocularly, orally, intranasally, sublingually, parenterally, or rectally or by inhalation or insufflation.

Compositions suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions and suspensions.

Alternatively, the composition may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition thereof contains an effective amount of the compound of the invention necessary to provide a therapeutic or prophylactic effect. The composition may contain from about 0.001 mg to about 5000 mg (preferably, from about 0.001 to about 500 mg) of a compound of the invention or salt form thereof and may be constituted into any form suitable for the mode of administration selected for a subject in need.

A contemplated effective amount may range from about 0.001 mg to about 300 mg/kg of body weight per day. Preferably, the range is from about 0.003 to about 100 mg/kg of body weight per day. Most preferably, the range is from about 0.005 to about 15 mg/kg of body weight per day. The composition may be administered according to a dosage regimen of from about 1 to about 5 times per day.

For oral administration, the composition is preferably in the form of a tablet or capsule containing, e.g., 0.01, 0.05, 0.1, 0.5, 1.0, 2.5, 5.0, 10.0, 15.0, 25.0, 50.0, 100, 150, 200, 250, or 500 milligrams of the compound of the invention for the symptomatic adjustment of the dosage to the patient to be treated. Optimal dosages will vary depending on factors associated with the particular patient being treated (e.g., age, weight, diet, time of administration, the severity and advancement of the condition being treated, the compound being employed, the mode of administration, the strength of the preparation and concomitant diseases. The use of either daily administration or post-periodic dosing may be employed. An optimal dose to be administered may be readily determined by those skilled in the art.

The oral composition is preferably formulated as a homogeneous composition wherein the compound of the invention is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more pharmaceutical carriers.

Because of their ease of administration, tablets and capsules represent an advantageous oral dosage unit form wherein solid pharmaceutical carriers are employed. If desired, tablets may be sugarcoated or filmcoated using standard techniques. Tablets may also be coated or otherwise compounded to provide a prolonged, control-release therapeutic effect.

Compounds of the invention may also be administered via a slow release composition, wherein the composition includes a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent.

The compound of Formula (I) may be incorporated for administration orally or by injection in a liquid form. The compounds may alternatively be administered parenterally via injection.

Compounds of the invention may be administered intranasally using a suitable intranasal vehicle. Compounds of the invention may be administered topically using a suitable topical transdermal vehicle or a transdermal patch. Administration via a transdermal delivery system requires a continuous rather than intermittent dosage regimen.

A representative compound of Formula (I) or a form thereof for use in the therapeutic methods and pharmaceutical compositions, medicines or medicaments described herein includes a compound selected from:

1-benzyl-1,4,6,7-tetrahydro-thiopyrano[4,3-c]pyrazole-3-carboxylic acid [(1R)-1-phenyl-ethyl]-amide, (E)-2-(1-benzyl-1,4,6,7-tetrahydro-thiopyrano[4-3-c]pyrazol-3-yl)-ethenesulfonic acid [(1S)-1-phenyl-ethyl]-amide, 1-benzyl-5,5-dioxo-4,5,6,7-tetrahydro-1H-5$\lambda^6$-thiopyrano[4,3-c]pyrazole-3-carboxylic acid [(1R)-1-phenyl-ethyl]-amide, 1-benzyl-1,4,6,7-tetrahydro-thiopyrano[4,3-c]pyrazole-3-carboxylic acid (1,3,3-trimethyl-bicyclo[2.2.1]hept-2-yl)-amide, 1-benzyl-5,5-dioxo-4,5,6,7-tetrahydro-1H-5$\lambda^6$-thiopyrano[4,3-c]pyrazole-3-carboxylic acid (1,3,3-trimethyl-bicyclo[2.2.1]hept-2-yl)-amide, 1-benzyl-5-oxo-4,5,6,7-tetrahydro-1H-5λ⁴-thiopyrano[4,3-c]pyrazole-3-carboxylic acid (1,3,3-trimethyl-bicyclo[2.2.1]hept-2-yl)-amide, (E)-2-[1-(2,4-difluoro-phenyl)-7-(3-fluoro-benzyl)-1,4,6,7-tetrahydro-thiopyrano[4,3-c]pyrazol-3-yl]-ethenesulfonic acid [(1R)-1-cyclohexyl-ethyl]-amide, (2R,3S)-3-{[1-(2,4-difluoro-phenyl)-(7S)-(3-fluoro-benzyl)-5,5-dioxo-4,5,6,7-tetrahydro-1H-5λ⁶-thiopyrano[4,3-c]pyrazole-3-carbonyl]-amino}-bicyclo[2.2.1]heptane-2-carboxylic acid ethyl ester, (7Z)-1-(2,4-dichloro-phenyl)-7-(4-fluoro-benzylidene)-1,4,6,7-tetrahydro-thiopyrano[4,3-c]pyrazole-3-carboxylic acid N'-(2,4-dichloro-phenyl)-hydrazide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid N'-(2,4-dichloro-phenyl)-hydrazide, (7Z)-1-(2,4-dichloro-phenyl)-7-(4-fluoro-benzylidene)-1,4,6,7-tetrahydro-thiopyrano[4,3-c]pyrazole-3-carboxylic acid piperidin-1-ylamide, (7Z)-[1-(2,4-dichloro-phenyl)-7-(4-fluoro-benzylidene)-1,4,6,7-tetrahydro-thiopyrano[4,3-c]pyrazol-3-yl]-piperidin-1-yl-methanone, (7Z)-1-(2,4-dichloro-phenyl)-7-(4-fluoro-benzylidene)-1,4,6,7-tetrahydro-thiopyrano[4,3-c]pyrazole-3-carboxylic acid pyrrolidin-1-ylamide, (7Z)-[1-(2,4-dichloro-phenyl)-7-(4-fluoro-benzylidene)-1,4,6,7-tetrahydro-thiopyrano[4,3-c]pyrazol-3-yl]-pyrrolidin-1-yl-methanone, (7Z)-1-(2,4-dichloro-phenyl)-7-(4-fluoro-benzylidene)-1,4,6,7-tetrahydro-thiopyrano[4,3-c]pyrazole-3-carboxylic acid [(1R,2S)-2-hydroxy-indan-1-yl]-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(1S,2R)-2-hydroxy-indan-1-yl]-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(1R,2R)-2-hydroxy-cyclopentyl]-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(1R,2R)-2-hydroxy-cyclohexyl]-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(1S)-1-phenyl-ethyl]-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(1R)-1-phenyl-ethyl]-amide, 4-{[(7Z)-1-(2,4-dichloro-phenyl)-7-(4-fluoro-benzylidene)-1,4,6,7-tetrahydro-thiopyrano[4,3-c]pyrazole-3-carbonyl]-amino}-piperazine-1-carboxylic acid tert-butyl ester, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid [(1S)-1-phenyl-ethyl]-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid [(1R)-1-phenyl-ethyl]-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid [(1S,2S)-2-hydroxy-cyclohexyl]-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid [(1R,2S)-2-hydroxy-indan-1-yl]-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid [(1S,2R)-2-hydroxy-indan-1-yl]-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid (pyridin-2-ylmethyl)-amide, (7Z)-1-(2,4-dichloro-phenyl)-7-(4-fluoro-benzylidene)-5-oxo-4,5,6,7-tetrahydro-1H-5λ⁴-thiopyrano[4,3-c]pyrazole-3-carboxylic acid [(1R)-1-phenyl-ethyl]-amide, (7Z)-1-(2,4-dichloro-phenyl)-7-(4-fluoro-benzylidene)-5-oxo-4,5,6,7-tetrahydro-1H-5λ⁴-thiopyrano[4,3-c]pyrazole-3-carboxylic acid N'-(2,4-dichloro-phenyl)-hydrazide, (7Z)-2-(2,4-dichloro-phenyl)-7-(4-fluoro-benzylidene)-2,4,6,7-tetrahydro-thiopyrano[4,3-c]pyrazole-3-carboxylic acid [(1R)-1-phenyl-ethyl]-amide, (7Z)-1-(2,4-dichloro-phenyl)-7-(4-fluoro-benzylidene)-5-oxo-4,5,6,7-tetrahydro-1H-5λ⁴-thiopyrano[4,3-c]pyrazole-3-carboxylic acid piperidin-1-ylamide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid piperidin-1-ylamide, (7Z)-2-(2,4-dichloro-phenyl)-7-(4-fluoro-benzylidene)-5,5-dioxo-4,5,6,7-tetrahydro-2H-5λ⁶-thiopyrano[4,3-c]pyrazole-3-carboxylic acid [(1R)-1-phenyl-ethyl]-amide, (7Z)-2-(2,4-dichloro-phenyl)-7-(4-fluoro-benzylidene)-5,5-dioxo-4,5,6,7-tetrahydro-2H-5λ⁶-thiopyrano[4,3-c]pyrazole-3-carboxylic acid piperidin-1-ylamide, (7Z)-2-(2,4-dichloro-phenyl)-7-(4-fluoro-benzylidene)-5,5-dioxo-4,5,6,7-tetrahydro-2H-5λ⁶-thiopyrano[4,3-c]pyrazole-3-carboxylic acid [(1R)-1-cyclohexyl-ethyl]-amide, (7Z)-2-(2,4-dichloro-phenyl)-7-(4-fluoro-benzylidene)-5,5-dioxo-4,5,6,7-tetrahydro-2H-5λ⁶-thiopyrano[4,3-c]pyrazole-3-carboxylic acid [(1S)-1-cyclohexyl-ethyl]-amide, (7Z)-2-(2,4-dichloro-phenyl)-7-(4-fluoro-benzylidene)-5,5-dioxo-4,5,6,7-tetrahydro-2H-5λ⁶-thiopyrano[4,3-c]pyrazole-3-carboxylic acid [(1S)-1-phenyl-ethyl]-amide, (7Z)-2-(2,4-dichloro-phenyl)-7-(4-fluoro-benzylidene)-5,5-dioxo-4,5,6,7-tetrahydro-2H-5λ⁶-thiopyrano[4,3-c]pyrazole-3-carboxylic acid (hexahydro-cyclopenta[c]pyrrol-2-yl)-amide, (7Z)-2-(2,4-dichloro-phenyl)-7-(4-fluoro-benzylidene)-2,4,6,7-tetrahydro-thiopyrano[4,3-c]pyrazole-3-carboxylic acid [(1R)-1-cyclohexyl-ethyl]-amide, (7Z)-1-(4-chloro-phenyl)-7-(4-fluoro-benzylidene)-1,4,6,7-tetrahydro-thiopyrano[4,3-c]pyrazole-3-carboxylic acid piperidin-1-ylamide, (7Z)-1-(4-chloro-phenyl)-7-(4-fluoro-benzylidene)-1,4,6,7-tetrahydro-thiopyrano[4,3-c]pyrazole-3-carboxylic acid [(1R)-1-phenyl-ethyl]-amide, (7Z)-1-(4-chloro-phenyl)-7-(4-fluoro-benzylidene)-5,5-dioxo-4,5,6,7-tetrahydro-1H-5λ⁶-thiopyrano[4,3-c]pyrazole-3-carboxylic acid [(1R)-1-phenyl-ethyl]-amide, (7Z)-1-(4-chloro-phenyl)-7-(4-fluoro-benzylidene)-5,5-dioxo-4,5,6,7-tetrahydro-1H-5λ⁶-thiopyrano[4,3-c]pyrazole-3-carboxylic acid (hexahydro-cyclopenta[c]pyrrol-2-yl)-amide, (7Z)-[1-(4-chloro-phenyl)-7-(4-fluoro-benzylidene)-5,5-dioxo-4,5,6,7-tetrahydro-1H-5λ⁶-thiopyrano[4,3-c]pyrazol-3-yl]-piperidin-1-yl-methanone, (7Z)-1-(4-chloro-phenyl)-7-(4-fluoro-benzylidene)-5,5-dioxo-4,5,6,7-tetrahydro-1H-5λ⁶-thiopyrano[4,3-c]pyrazole-3-carboxylic acid piperidin-1-ylamide, (7Z)-1-(4-chloro-phenyl)-7-(4-fluoro-benzylidene)-5,5-dioxo-4,5,6,7-tetrahydro-1H-5λ⁶-thiopyrano[4,3-c]pyrazole-3-carboxylic acid N'-methyl-N'-phenyl-hydrazide, (7Z)-[1-(2,4-dichloro-phenyl)-7-(4-fluoro-benzylidene)-5,5-dioxo-4,5,6,7-tetrahydro-1H-5λ⁶-thiopyrano[4,3-c]pyrazol-3-yl]-piperidin-1-yl-methanone, (7Z)-1-(4-chloro-phenyl)-7-(4-fluoro-benzylidene)-1,4,6,7-tetrahydro-thiopyrano[4,3-c]pyrazole-3-carboxylic acid pyrrolidin-1-ylamide, (7Z)-1-(4-chloro-phenyl)-7-(4-fluoro-benzylidene)-1,4,6,7-tetrahydro-thiopyrano[4,3-c]pyrazole-3-carboxylic acid (hexahydro-cyclopenta[c]pyrrol-2-yl)-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid (hexahydro-cyclopenta[c]pyrrol-2-yl)-amide, (7Z)-1-(2,4-difluoro-phenyl)-7-(4-fluoro-benzylidene)-5,5-dioxo-4,5,6,7-tetrahydro-1H-5λ⁶-thiopyrano[4,3-c]pyrazole-3-carboxylic acid (hexahydro-cyclopenta[c]pyrrol-2-yl)-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid azepan-1-ylamide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid (2,6-dimethyl-piperidin-1-yl)-amide, (7Z)-1-(2,4-dichloro-phenyl)-7-(4-fluoro-benzylidene)-1,4,6,7-tetrahydro-thiopyrano[4,3-c]pyrazole-3-carboxylic acid (2,6-dimethyl-piperidin-1-yl)-amide, (7Z)-1-(2,4-dichloro-phenyl)-7-(4-fluoro-benzylidene)-1,4,6,7-tetrahydro-thiopyrano[4,3-c]pyrazole-3-carboxylic acid azepan-1-ylamide, (7Z)-1-(2,4-dichloro-phenyl)-7-(4-fluoro-benzylidene)-1,4,6,7-tetrahydro-thiopyrano[4,3-c]pyrazole-3-carboxylic acid N'-cyclohexyl-hydrazide, (7Z)-1-(2,4-dichloro-phenyl)-7-(4-fluoro-benzylidene)-1,4,6,7-tetrahydro-thiopyrano[4,3-c]pyrazole-3-carboxylic acid (hexahydro-cyclopenta[c]pyrrol-2-yl)-amide, (7Z)-7-(5-chloro-furan-2-ylmethylene)-1-(2,4-dichloro-phenyl)-5,5-dioxo-4,5,6,7-tetrahydro-1H-5λ⁶-thiopyrano[4,3-c]pyrazole-3-carboxylic acid [(1R)-1-phenyl-ethyl]-amide, (7Z)-7-(5-chloro-furan-2-ylmethylene)-1-(2,4-dichloro-phenyl)-5,5-dioxo-4,5,6,7-tetrahydro-1H-5λ⁶-thiopyrano[4,3-c]pyrazole-3-carboxylic acid [(1R)-1-cyclohexyl-ethyl]-amide, (7Z)-7-(5-chloro-furan-2-ylmethylene)-1-(2,4-dichloro-phenyl)-5,5-dioxo-4,5,6,7-tetrahydro-1H-5λ⁶-thiopyrano[4,3-c]pyrazole-3-carboxylic acid piperidin-1-ylamide, (7Z)-7-(5-chloro-furan-2-ylmethylene)-1-(2,4-dichloro-phenyl)-5,5-dioxo-4,5,6,7-tetrahydro-1H-5λ⁶-thiopyrano[4,3-c]pyrazole-3-carboxylic acid azepan-1-ylamide, (7Z)-7-(5-chloro-furan-2-ylmethylene)-1-(2,4-dichloro-phenyl)-5,5-dioxo-4,5,6,7-tetrahydro-1H-5λ⁶-thiopyrano[4,3-c]pyrazole-3-carboxylic acid (hexahydro-cyclopenta[c]pyrrol-2-yl)-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(2R)-2-(methoxymethyl)-pyrrolidin-1-yl]-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(2S)-2-(methoxymethyl)-pyrrolidin-1-yl]-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid [(1R)-1-(pyridin-2-yl)-ethyl]-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid [(2S)-2-(methoxymethyl)-pyrrolidin-1-yl]-amide, (7Z)-1-(2,4-dichloro-phenyl)-7-(4-fluoro-benzylidene)-5,5-dioxo-4,5,6,7-tetrahydro-1H-5λ⁶-thiopyrano[4,3-c]pyrazole-3-carboxylic acid [(2R)-2-(methoxymethyl)-pyrrolidin-1-yl]-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(1R)-1-(pyridin-2-yl)-ethyl]-amide, (7Z)-(4-Bromo-benzylidene)-1-(2,4-dichloro-phenyl)-1,4,6,7-tetrahydro-thiopyrano[4,3-c]pyrazole-3-carboxylic acid [(1R)-1-phenyl-ethyl]-amide, and (7Z)-(4-Bromo-benzylidene)-1-(2,4-dichloro-phenyl)-1,4,6,7-tetrahydro-thiopyrano[4,3-c]pyrazole-3-carboxylic acid piperidin-1-ylamide.

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations have the indicated meanings:

| | |
|---|---|
| Boc | tert-butoxy carbonyl or acid t-butyl ester |
| (Boc)₂O | di-tert-butyldicarbonate or di-t-butyl-dicarbonate |
| CH₂Cl₂ | methylene chloride |
| Cpd | compound |
| DMAP | |
| EtOAc | ethylacetate |
| EtOH | ethanol |
| Et₂O | diethyl ether |
| KOH | potassium hydroxide |
| KOtBu | potassium tert-butoxide |
| K₂CO₃ | potassium carbonate |
| LDA | lithium diisopropylamide |
| LiOH | lithium hydroxide |
| MeOH | methanol |
| min/hr | minute(s)/hour(s) |
| MS | Mass Spectrum shown as MS m/z M + H⁺ |
| NaHCO₃ | sodium bicarbonate |
| NaIO₄ | sodium periodate |
| Na₂SO₄ | sodium sulfate |
| NEt₃ | triethylamine |
| RT/rt/r.t. | room temperature |
| TEA | triethylamine |
| THF | tetrahydrofuran |

All commercially available chemicals were obtained from commercial suppliers and used without further purification. Particular components or equipment used in the examples, such as reaction vessels and the like, are also commercially available.

Scheme A

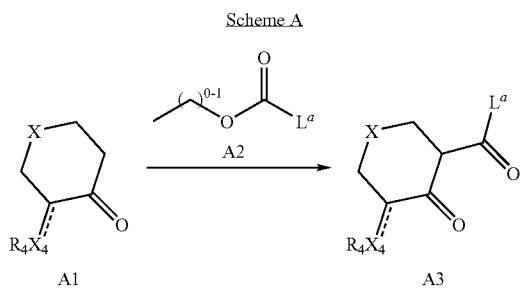

A substituted tetrahydro-thiopyran-4-one Compound A1 is added dropwise to a solution of LDA (in a solvent such as anhydrous THF and the like) at −78° C. under an inert atmosphere blanket (typically using nitrogen gas and the like) when the $L^a$ portion of Compound A2 is dialkoxy-methane and the like. The mixture is stirred at −78° C. for 1 hr, then a solution of Compound A2 (in a solvent such as anhydrous THF and the like) is added dropwise.

Alternatively, Compound A1 is added dropwise to a solution of KOtBu (in a solvent such as anhydrous THF and the like) at −78° C. under an inert atmosphere blanket when the $L^a$ portion of Compound A2 is dialkoxy-methane or alkyl-carboxy and the like). The mixture is stirred and allowed to warm to r.t. for 15 hrs and the reaction is quenched (typically using water). The organic layer is diluted (in a solvent such as EtOAc and the like), washed (with water, a dilute solution of HCl and the like or mixtures thereof or sequentially with water and brine), separated and dried (such as with anhydrous $Na_2SO_4$ and the like), then filtered, concentrated (typically, in vacuo) and purified to yield Compound A3.

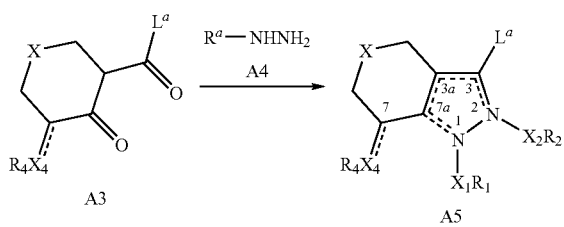

A solution of Compound A4 (in a solvent such as MeOH and the like) is added to a solution of Compound A3 (in a solvent such as MeOH and the like) at a temperature of about 0° C. under an inert atmosphere. The mixture is stirred and warmed to r.t. (i.e. ambient temperature) over a 15 hr period, then the reaction is quenched (typically using water) and diluted (in a solvent such as EtOAc and the like). The organic layer is washed (with water, a dilute solution of HCl and the like or mixtures thereof or sequentially with water and brine), separated and dried (such as with anhydrous $Na_2SO_4$ and the like), then filtered, concentrated (typically, in vacuo) and optionally purified to yield Compound A5.

In many instances, substituted hydrazine compounds (of which Compound A4 is representative) are commercially available in either the free base or salt form. When not commercially available, other hydrazines may be prepared by methods known to those skilled in the art. Preferably, the substituted hydrazine compound used is either commercially available or prepared as a free base.

When the salt form is present, typically, the salt is either a mono- or di-acid salt. For example, the hydrochloride or dihydrochloride salt of Compound A4 is converted to the free base and carried forward to prepare certain compounds of the invention. The free base form of Compound A4 is prepared using techniques known to those skilled in the art. Typically, an excess of $K_2CO_3$ is added to a solution of the hydrochloride (1.2 equivalents excess) or dihydrochloride (2.4 equivalents excess) salt form of the substituted hydrazine Compound A4 (dissolved in water), the mixture is stirred at ambient temperature for up to 2 hrs. The organic layer is extracted (using $CH_2Cl_2$ and the like) and dried (typically using $Na_2SO_4$ and the like), then the mixture is filtered and concentrated (typically in vacuo) to provide Compound A4 as a free base.

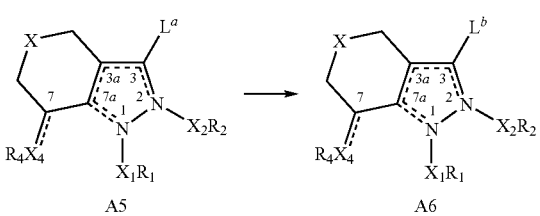

A reagent solution is added to a solution of Compound A5 (in a solvent such as acetone and the like) at 0° C. under an inert atmosphere. When $L^a$ is a dialkoxy-methane, the reagent solution may be 3N HCl and the like to provide the $L^b$ aldehyde. When $L^a$ is an alkyl-carboxy, the reagent solution may be LiOH and the like to provide $L^b$ as a carboxylic acid; the resulting $L^b$ carboxylic acid may be further reacted with a reagent solution such as $SOCl_2$ and the like to provide $L^b$ as a carboxyl chloride.

When the reagent solution is 3N HCl and the like, the mixture is stirred and warmed to r.t. (i.e. ambient temperature) over a period of 4 hrs, then the reaction is quenched (typically using water). The reaction mixture is neutralized to pH 7 (typically using $K_2CO_3$) and diluted (in a solvent such as $CH_2Cl_2$ and the like). The organic layer is washed (sequentially with water and brine), separated and dried (such as with anhydrous $Na_2SO_4$ and the like), then filtered, concentrated (typically, in vacuo) and purified to yield Compound A6 as a mixture of a major and minor isomers.

When the reagent solution is LiOH and the like, the mixture is stirred for 24 hrs, then acidified to pH 3 (typically using 1N HCl) and extracted (typically using EtOAc). The organic layer is washed with brine and dried over $Na_2SO_4$, then filtered and concentrated in vacuo to yield Compound A6 as a mixture of a major and minor isomers.

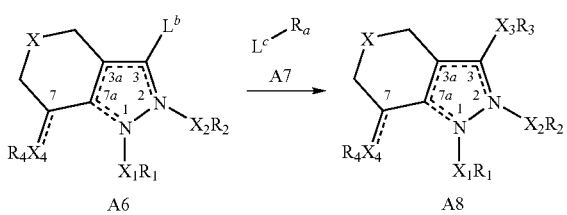

When $L^b$ for Compound A6 is an aldehyde and $L^c$ for Compound A7 is an alkyl reacting group and $R^a$ is -Z-N($R_6$)-$Z_1R_7$, a reagent solution such as 1M KOtBu (in a solvent such as THF and the like) is added dropwise to a solution of Compound A7 (in a solvent such as anhydrous THF) at −78° C. under an inert atmosphere and the mixture is stirred at −78°

C. for 45 min. Then a solution of Compound A6 (in a solvent such as THF) is added dropwise. The mixture is stirred and warmed to r.t. over a period of 15 hrs, then the reaction is quenched (typically using water). The organic layer is diluted (in a solvent such as EtOAc and the like) and washed (with water and brine), separated and dried (such as with anhydrous $Na_2SO_4$ and the like), then filtered, concentrated (typically, in vacuo) and optionally purified to yield Compound A8 of Formula (I).

When $L^b$ is a carboxyl chloride and $L^c$ is an amine reacting group and $R^a$ is heterocyclyl or —$N(R_6)$-$Z_1R_7$ (in certain embodiments, the $R^a$ heterocyclyl ring system nitrogen may be the reactive $L^c$ amine), a reagent solution such as TEA (in a solvent such as DCM and the like) is added to a solution of Compound A7 (in a solvent such as anhydrous DCM) at about r.t. under an inert atmosphere and the mixture is stirred for 15 min.

A solution of Compound A6 (in a solvent such as DCM) is added dropwise and the mixture is stirred at r.t. for 2 hrs. The reaction is diluted (typically with DCM) and washed (typically using water). The organic layer is separated and dried (such as with anhydrous $Na_2SO_4$ and the like), then filtered, concentrated (typically, in vacuo) and purified by flash chromatography to yield Compound A8 of Formula (I).

Scheme B

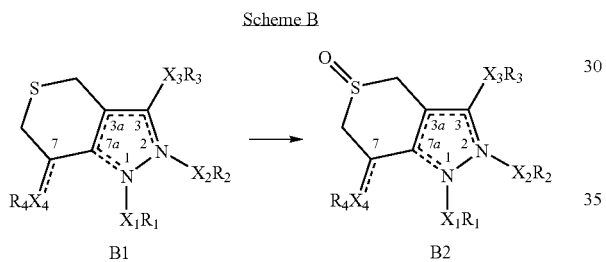

NaIO$_4$ is added to a solution of Compound B1 (in a solvent such as MeOH, THF, water and the like or mixtures thereof) at 0° C. under an inert atmosphere. The mixture is stirred and warmed to r.t. over a period of 20 hrs, then the reaction is quenched and diluted (with a solvent such as EtOAc and the like). The organic layer is washed (with water and brine), separated and dried (such as with anhydrous $Na_2SO_4$ and the like), then filtered, concentrated (typically, in vacuo) and purified to yield Compound B2.

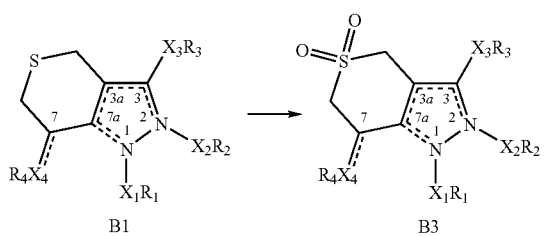

Oxone® is added to a solution of Compound B1 (in a solvent such as MeOH, water and the like or mixtures thereof) at 0° C. under an inert atmosphere. The mixture is stirred and warmed to r.t. over a period of 12 hrs, then the reaction is quenched and diluted (with a solvent such as EtOAc and the like). The organic layer is washed (with water and brine), separated and dried (such as with anhydrous $Na_2SO_4$ and the like), then filtered, concentrated (typically, in vacuo) and purified to yield Compound B3.

The specific synthetic examples that follow herein describe more completely the preparation of particular compounds, which are non-limiting illustrations of compounds intended to be included within the scope of the present invention. Using the procedures provided herein, one skilled in the art may prepare other compounds that are similarly representative of the invention by varying the starting materials, reagent (s) and conditions used.

EXAMPLE 1

(E)-2-(1-benzyl-1,4,6,7-tetrahydro-thiopyrano[4,3-c]pyrazol-3-yl)-ethenesulfonic acid [(1R)-1-phenyl-ethyl]-amide (Cpd 7)

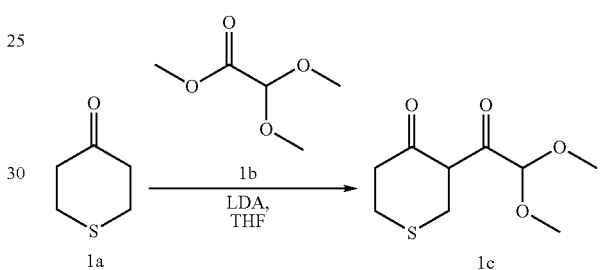

Tetrahydro-4H-thiopyran-4-one Compound 1a (5.0 g, 43 mmol) was added dropwise to a solution of LDA (28.6 mL, 51.6 mmol) in anhydrous THF (50 mL) at −78° C. under a $N_2$ atmosphere. The mixture was stirred at −78° C. for 1 hr, then dimethoxy-acetic acid methyl ester Compound 1b (5.78 g, 43.0 mmol) in anhydrous THF (5 mL) was added dropwise. The solution was stirred and warmed to r.t. over a 15 hr period, then the reaction was quenched with water (5 mL). The organic layer was diluted with EtOAc (200 mL) and washed with water and brine, separated and dried with anhydrous $Na_2SO_4$, then filtered and concentrated in vacuo to yield a crude oil, which was purified by flash chromatography (eluted with 10% EtOAc in hexane) to afford Compound 1c (6.56 g, 70%).

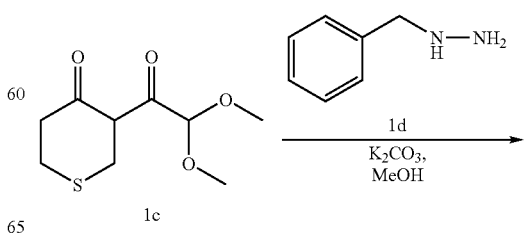

-continued

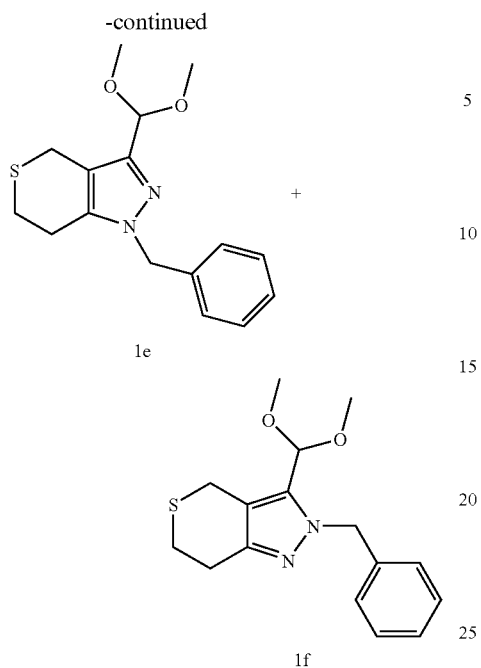

1e

1f

An excess of K₂CO₃ (7.5 g) was added to a solution of benzylhydrazine dihydrochloride (7.00 g, 35.9 mmol) in Et₂O (100 mL). The mixture was stirred at ambient temperature for 2 hrs and the reaction was quenched with water (20 mL). The organic layer was washed with water and brine and dried with anhydrous Na₂SO₄, then filtered and concentrated in vacuo to yield benzylhydrazine Compound 1d (4.17 g, 34.2 mmol).

Benzylhydrazine Compound 1d (3.63 g, 29.8 mmol) in MeOH (10 mL) was added to a solution of Compound 1c (6.5 g, 30 mmol) in MeOH (75 mL) at 0° C. under a N₂ atmosphere. The mixture was stirred and warmed to r.t. over a 15 hr period. The reaction was quenched with water (20 mL) and diluted with EtOAc (200 mL). The organic layer was washed with water and brine, separated and dried with anhydrous Na₂SO₄, then filtered and concentrated in vacuo to yield a crude oil, which was purified by flash chromatography (eluted with 10% EtOAc in hexane) to afford a mixture of a major isomer Compound 1e and a minor isomer Compound 1f (6.76 g, 75%).

-continued

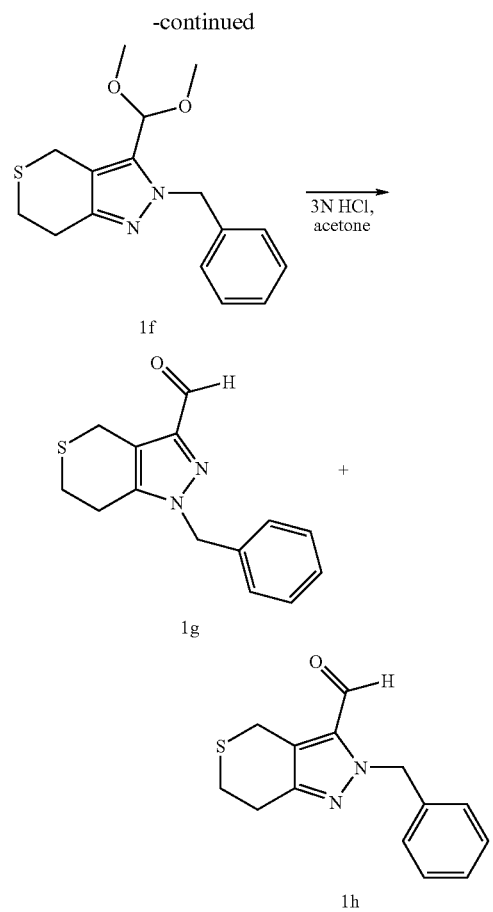

1f

1g

1h

3N HCl (8 mL) was added to a solution of the mixture of Compound 1e and Compound 1f (6.5 g, 21 mmol) in acetone (50 mL) at 0° C. under a N₂ atmosphere. The mixture was stirred and warmed to r.t. over a 4 hr period. The reaction was quenched with water (20 mL), neutralized to pH 7 with K₂CO₃ and diluted with CH₂Cl₂ (100 mL). The organic layer was washed with water and brine, separated and dried with anhydrous Na₂SO₄, then filtered and concentrated in vacuo to yield a crude oil, which was purified by flash chromatography (eluted with 10% EtOAc in hexane) to yield a major isomer carbaldehyde Compound 1g (3.49 g, 63%) and a minor isomer carbaldehyde Compound 1h (1.75 g, 31%) as a colorless oil.

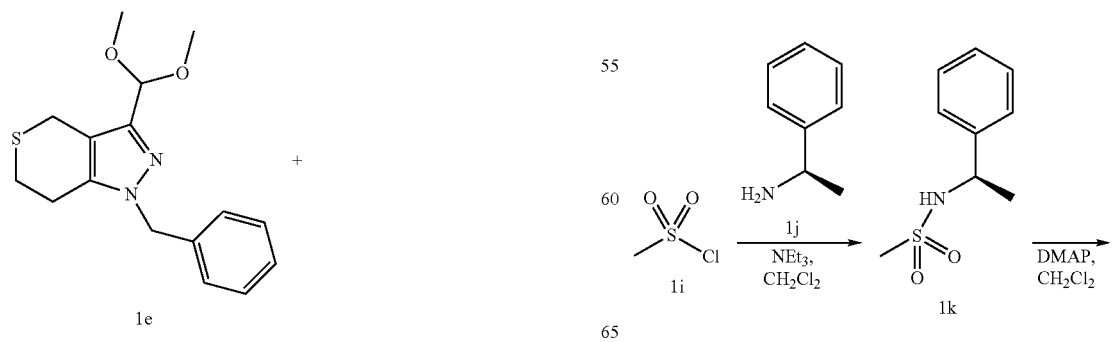

1e

1i

1j

1k

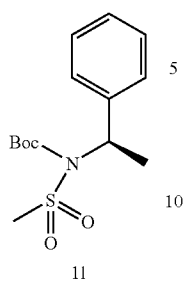

NEt₃ (2.43 mL, 17.46 mmol) and methanesulfonyl chloride Compound 1i (2.0 g, 17 mmol) were added to a solution of ($\alpha^1$R)-α-methyl-benzenemethanamine Compound 1j (1.75 g, 17.5 mmol) at 0° C. under a N₂ atmosphere. The mixture was stirred and warmed to r.t. over a 3 hr period, then the reaction was quenched with water (5 mL). The organic layer was diluted with CH₂Cl₂ (100 mL) and washed with water and brine, separated and dried with anhydrous Na₂SO₄, then filtered and concentrated in vacuo to afford the corresponding sulfonamide Compound 1k as an oil.

Di-tert-butyldicarbonate (4.57 g, 21.0 mmol) and DMAP (8 mg) were added to a solution of Compound 1k in CH₂Cl₂ (10 mL) at 0° C. under a N₂ atmosphere. The mixture was stirred and warmed to r.t. overnight, then the reaction was quenched with a saturated solution of NaHCO₃ (10 mL). The organic layer was diluted with CH₂Cl₂ (100 mL) and washed with water and brine, separated and dried with anhydrous Na₂SO₄, then filtered and concentrated in vacuo to yield a crude Boc-protected methanesulphonamide, which was purified by flash chromatography using 10% EtOAc in hexane to afford Compound 11 (3.89 g, 80%) as a colorless oil (the preceding method was an adaption of the procedure described in Tozer M J, Woolford A J A and Linney I A, *Synlett*, 1998, 2, 186-188).

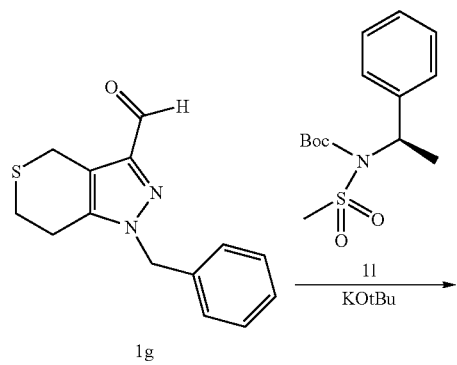

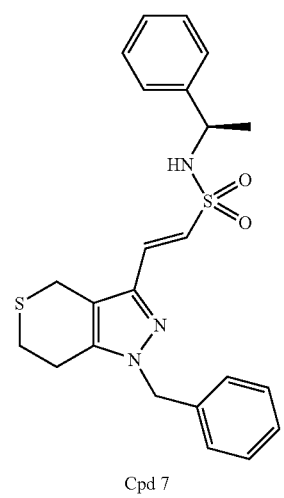

Cpd 7

A 1M solution of KOtBu in THF (0.75 mL, 0.75 mmol) was added dropwise to a solution of Compound 11 (0.050 g, 0.250 mmol) in anhydrous THF (5 mL) at −78° C. under a N₂ atmosphere. The mixture was stirred for 45 min, then 1-benzyl-1,4,6,7-tetrahydro-thiopyrano[4,3-c]pyrazole-3-carbaldehyde Compound 1g (0.116 g, 0.250 mmol) diluted in THF (3 mL) was added dropwise. The mixture was warmed to ambient temperature over a period of 15 hrs, then the reaction was quenched with water (5 mL). The organic layer was diluted with EtOAc (100 mL) and washed with water and brine, separated and dried with anhydrous Na₂SO₄, then filtered and concentrated in vacuo to yield a crude product, which was purified by flash chromatography (eluted with 20% EtOAc in hexane) to give Compound 7 (0.082 g, 75%) as a white solid. MS m/z 440.1 (MH⁺); ¹H NMR (CDCl₃, 400 MHz) δ 7.43-7.15 (m, 11H), 6.73 (d, J=8.4 Hz, 1H), 6.44 (d, J=15.7 Hz, 1H), 5.30 (s, 2H), 4.59-4.54 (m, 1H), 3.41 (s, 2H), 2.91 (s, 2H), 1.51 (d, J=7.0 Hz, 3H).

Using the procedure of Example 1, other compounds that are representative of the invention may be prepared by varying the starting materials, reagent(s) and conditions used, such as:

| Cpd | Name | MS |
|---|---|---|
| 11 | (E)-2-(1-benzyl-1,4,6,7-tetrahydro-thiopyrano[4,3-c]pyrazol-3-yl)-ethenesulfonic acid [(1R)-1-cyclohexyl-ethyl]-amide | 446.1 |

EXAMPLE 2

(E)-2-(1-benzyl-5-oxo-4,5,6,7-tetrahydro-1H-5$\lambda^4$-thiopyrano[4,3-c]pyrazol-3-yl)-ethenesulfonic acid [(1R)-1-phenyl-ethyl]-amide (Cpd 30)

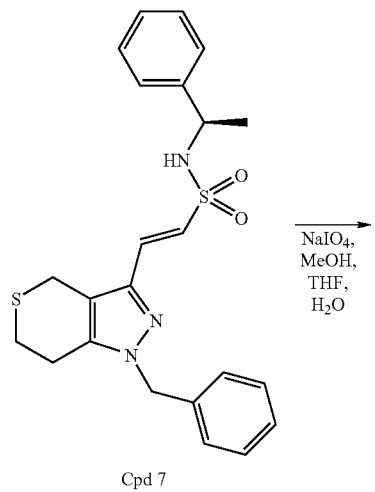

Cpd 7

NaIO$_4$, MeOH, THF, H$_2$O

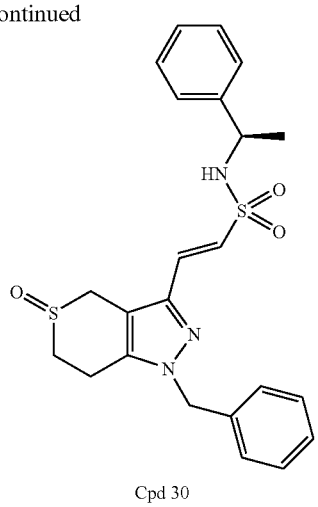

Cpd 30

NaIO$_4$ (0.038 g, 0.18 mmol) was added to a solution of amide Compound 7 (0.04 g, 0.09 mmol) in a mixture of MeOH, THF and water (4 mL) (1:1:2) at 0° C. under a N$_2$ atmosphere. The mixture was stirred and warmed to ambient temperature over a 20 hr period, then diluted with EtOAc. The organic layer was washed with water and brine, dried with anhydrous Na$_2$SO$_4$, then filtered and concentrated in vacuo to yield a crude oil, which was purified by flash chromatography to afford Compound 30 (0.032 g, 80%) as a white solid. MS m/z 456 (MH$^+$).

Using the procedure of Example 2, other compounds that are representative of the invention may be prepared by varying the starting materials, reagent(s) and conditions used, such as:

| Cpd | Name | MS |
|---|---|---|
| 21 | 1-benzyl-5-oxo-4,5,6,7-tetrahydro-1H-5$\lambda^4$-thiopyrano[4,3-c]pyrazole-3-carboxylic acid (1,3,3-trimethyl-bicyclo[2.2.1]hept-2-yl)-amide | 426 |
| 22 | (E)-2-(2-benzyl-5-oxo-4,5,6,7-tetrahydro-2H-5$\lambda^4$-thiopyrano[4,3-c]pyrazol-3-yl)-ethenesulfonic acid (1-phenyl-ethyl)-amide | 456.1 |
| 23 | (E)-2-(2-benzyl-5-oxo-4,5,6,7-tetrahydro-2H-5$\lambda^4$-thiopyrano[4,3-c]pyrazol-3-yl)-ethenesulfonic acid [(1R)-1-phenyl-ethyl]-amide | 456.1 |
| 24 | (E)-2-(2-benzyl-5-oxo-4,5,6,7-tetrahydro-2H-5$\lambda^4$-thiopyrano[4,3-c]pyrazol-3-yl)-ethenesulfonic acid [(1S)-1-phenyl-ethyl]-amide | 456.1 |
| 25 | (E)-2-(1-benzyl-5-oxo-4,5,6,7-tetrahydro-1H-5$\lambda^4$-thiopyrano[4,3-c]pyrazol-3-yl)-ethenesulfonic acid (1-cyclohexyl-ethyl)amide | 462.1 |
| 26 | (E)-2-(2-benzyl-5-oxo-4,5,6,7-tetrahydro-2H-5$\lambda^4$-thiopyrano[4,3-c]pyrazol-3-yl)-ethenesulfonic acid (1-cyclohexyl-ethyl)-amide | 462.1 |
| 27 | (E)-2-(2-benzyl-5-oxo-4,5,6,7-tetrahydro-2H-5$\lambda^4$-thiopyrano[4,3-c]pyrazol-3-yl)-ethenesulfonic acid [(1R)-1-cyclohexyl-ethyl]-amide | 462.1 |
| 28 | (E)-2-(2-benzyl-5-oxo-4,5,6,7-tetrahydro-2H-5$\lambda^4$-thiopyrano[4,3-c]pyrazol-3-yl)-ethenesulfonic acid [(1S)-1-cyclohexyl-ethyl]-amide | 462.1 |
| 29 | (E)-2-(1-benzyl-5-oxo-4,5,6,7-tetrahydro-1H-5$\lambda^4$-thiopyrano[4,3-c]pyrazol-3-yl)-ethenesulfonic acid (1-phenyl-ethyl)-amide | 456 |

-continued

| Cpd | Name | MS |
|---|---|---|
| 31 | (E)-2-(1-benzyl-5-oxo-4,5,6,7-tetrahydro-1H-5$\lambda^4$-thiopyrano[4,3-c]pyrazol-3-yl)-ethenesulfonic acid [(1S)-1-phenyl-ethyl]-amide | 456 |
| 34 | (2E)-3-(1-benzyl-5-oxo-4,5,6,7-tetrahydro-1H-5$\lambda^4$-thiopyrano[4,3-c]pyrazol-3-yl)-N-[(1S)-1-phenyl-ethyl]-acrylamide | 420.1 |
| 35 | (2E)-3-(1-benzyl-5-oxo-4,5,6,7-tetrahydro-1H-5$\lambda^4$-thiopyrano[4,3-c]pyrazol-3-yl)-N-[(1R)-1-phenyl-ethyl]-acrylamide | 420.1 |
| 74 | (7Z)-1-(2,4-dichloro-phenyl)-7-(4-fluoro-benzylidene)-5-oxo-4,5,6,7-tetrahydro-1H-5$\lambda^4$-thiopyrano[4,3-c]pyrazole-3-carboxylic acid [(1S)-1-phenyl-ethyl]-amide | 554 |
| 75 | (7Z)-1-(2,4-dichloro-phenyl)-7-(4-fluoro-benzylidene)-5-oxo-4,5,6,7-tetrahydro-1H-5$\lambda^4$-thiopyrano[4,3-c]pyrazole-3-carboxylic acid [(1R)-1-phenyl-ethyl]-amide | 554 |
| 76 | (7Z)-1-(2,4-dichloro-phenyl)-7-(4-fluoro-benzylidene)-5-oxo-4,5,6,7-tetrahydro-1H-5$\lambda^4$-thiopyrano[4,3-c]pyrazole-3-carboxylic acid [(1R,2R)-2-hydroxy-cyclopentyl]-amide | 558 (+Na) |
| 77 | (7Z)-1-(2,4-dichloro-phenyl)-7-(4-fluoro-benzylidene)-5-oxo-4,5,6,7-tetrahydro-1H-5$\lambda^4$-thiopyrano[4,3-c]pyrazole-3-carboxylic acid N'-(2,4-dichloro-phenyl)-hydrazide | 612 |
| 79 | (7Z)-1-(2,4-dichloro-phenyl)-7-(4-fluoro-benzylidene)-5-oxo-4,5,6,7-tetrahydro-1H-5$\lambda^4$-thiopyrano[4,3-c]pyrazole-3-carboxylic acid piperidin-1-ylamide | 533.1 |
| 80 | (7Z)-1-(2,4-dichloro-phenyl)-7-(4-fluoro-benzylidene)-5-oxo-4,5,6,7-tetrahydro-1H-5$\lambda^4$-thiopyrano[4,3-c]pyrazole-3-carboxylic acid (pyridin-2-ylmethyl)-amide | 541 |
| 96 | (7Z)-1-(4-chloro-phenyl)-7-(4-fluoro-benzylidene)-5-oxo-4,5,6,7-tetrahydro-1H-5$\lambda^4$-thiopyrano[4,3-c]pyrazole-3-carboxylic acid piperidin-1-ylamide | 499.2 |

EXAMPLE 3

(E)-2-(1-benzyl-5,5-dioxo-4,5,6,7-tetrahydro-1H-5$\lambda^6$-thiopyrano[4-3-c]pyrazol-3-yl)-ethenesulfonic acid [(1R)-1-phenyl-ethyl]-amide (Cpd 9)

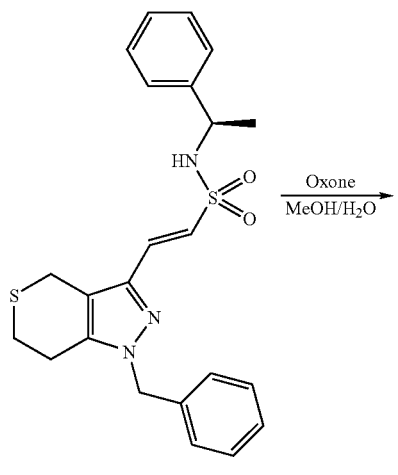

Cpd 7

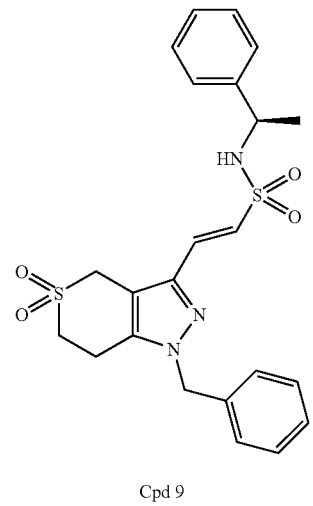

Cpd 9

Oxone® (0.202 g, 0.330 mmol) was added to a solution of Compound 7 (0.05 g, 0.11 mmol) in a mixture of MeOH and water (1:1) at 0° C. under a $N_2$ atmosphere. The solution was stirred and warmed to ambient temperature over a 12 hr period, then diluted with EtOAc. The organic layer was washed with water and brine and dried with anhydrous $Na_2SO_4$, then filtered and concentrated in vacuo to yield a crude oil, which was purified by flash chromatography to afford Compound 9 (0.049 g, 95%) as a white solid. MS m/z 472.1 (MH$^+$); $^1$H NMR (CDCl$_3$, 400 MHz) δ 7.38-7.15 (m, 11H), 6.78 (d, J=9.1 Hz, 1H), 6.21 (d, J=15.5 Hz, 1H), 5.42 (s, 2H), 4.44-4.39 (m, 1H), 3.31 (dd, J=15.6, 15.8 Hz, 1H), 2.87-2.80 (m, 6H), 1.44 (d, J=7.0 Hz, 3H).

Using the procedure of Example 3, other compounds that are representative of the invention may be prepared by varying the starting materials, reagent(s) and conditions used, such as:

| Cpd | Name | MS |
|---|---|---|
| 4 | (E)-2-(2-benzyl-5,5-dioxo-4,5,6,7-tetrahydro-2H-5$\lambda^6$-thiopyrano[4,3-c]pyrazol-3-yl)-ethenesulfonic acid [(1R)-1-phenyl-ethyl]-amide | 472.2 |
| 10 | (E)-2-(2-benzyl-5,5-dioxo-4,5,6,7-tetrahydro-2H-5$\lambda^6$-thiopyrano[4,3-c]pyrazol-3-yl)-ethenesulfonic acid [(1S)-1-phenyl-ethyl]-amide | 472 |
| 13 | 1-benzyl-5,5-dioxo-4,5,6,7-tetrahydro-1H-5$\lambda^6$-thiopyrano[4,3-c]pyrazole-3-carboxylic acid [(1R)-1-phenyl-ethyl]-amide | 410 |
| 14 | (E)-2-(1-benzyl-5,5-dioxo-4,5,6,7-tetrahydro-1H-5$\lambda^6$-thiopyrano[4,3-c]pyrazol-3-yl)-ethenesulfonic acid [(1R)-1-cyclohexyl-ethyl]-amide | 478 |
| 15 | (E)-2-(1-benzyl-5,5-dioxo-4,5,6,7-tetrahydro-1H-5$\lambda^6$-thiopyrano[4,3-c]pyrazol-3-yl)-ethenesulfonic acid [(1S)-1-cyclohexyl-ethyl]-amide | 478 |
| 16 | (E)-2-(2-benzyl-5,5-dioxo-4,5,6,7-tetrahydro-2H-5$\lambda^6$-thiopyrano[4,3-c]pyrazol-3-yl)-ethenesulfonic acid [(1R)-1-cyclohexyl-ethyl]-amide | 478.2 |
| 17 | (E)-2-(2-benzyl-5,5-dioxo-4,5,6,7-tetrahydro-2H-5$\lambda^6$-thiopyrano[4,3-c]pyrazol-3-yl)-ethenesulfonic acid [(1S)-1-cyclohexyl-ethyl]-amide | 478.2 |
| 18 | (E)-2-(1-benzyl-5,5-dioxo-4,5,6,7-tetrahydro-1H-5$\lambda^6$-thiopyrano[4,3-c]pyrazol-3-yl)-ethenesulfonic acid [(1S)-1-phenyl-ethyl]-amide | 472.1 |
| 20 | 1-benzyl-5,5-dioxo-4,5,6,7-tetrahydro-1H-5$\lambda^6$-thiopyrano[4,3-c]pyrazole-3-carboxylic acid (1,3,3-trimethyl-bicyclo[2.2.1]hept-2-yl)-amide | 442 |
| 36 | (2E)-3-(1-benzyl-5,5-dioxo-4,5,6,7-tetrahydro-1H-5$\lambda^6$-thiopyrano[4,3-c]pyrazol-3-yl)-N-[(1S)-1-phenyl-ethyl]-acrylamide | 436 |
| 37 | (2E)-3-(1-benzyl-5,5-dioxo-4,5,6,7-tetrahydro-1H-5$\lambda^6$-thiopyrano[4,3-c]pyrazol-3-yl)-N-[(1R)-1-phenyl-ethyl]-acrylamide | 436 |
| 42 | (E)-2-[1-(2,4-difluoro-phenyl)-7-(3-fluoro-benzyl)-5,5-dioxo-4,5,6,7-tetrahydro-1H-5$\lambda^6$-thiopyrano[4,3-c]pyrazol-3-yl]-ethenesulfonic acid [(1S)-1-phenyl-ethyl]-amide | 602.1 |
| 43 | (E)-2-[1-(2,4-difluoro-phenyl)-7-(3-fluoro-benzyl)-5,5-dioxo-4,5,6,7-tetrahydro-1H-5$\lambda^6$-thiopyrano[4,3-c]pyrazol-3-yl]-ethenesulfonic acid [(1R)-1-cyclohexyl-ethyl]-amide | 608.1 |
| 44 | (E)-2-[1-(2,4-difluoro-phenyl)-7-(3-fluoro-benzyl)-5,5-dioxo-4,5,6,7-tetrahydro-1H-5$\lambda^6$-thiopyrano[4,3-c]pyrazol-3-yl]-ethenesulfonic acid morpholin-4-ylamide | 583 |
| 45 | (E)-2-[1-(2,4-difluoro-phenyl)-7-(3-fluoro-benzyl)-5,5-dioxo-4,5,6,7-tetrahydro-1H-5$\lambda^6$-thiopyrano[4,3-c]pyrazol-3-yl]-ethenesulfonic acid piperidin-1-ylamide | 579.2 |
| 49 | (2R,3S)-3-{[1-(2,4-difluoro-phenyl)-(7R)-(3-fluoro-benzyl)-5,5-dioxo-4,5,6,7-tetrahydro-1H-5$\lambda^6$-thiopyrano[4,3-c]pyrazole-3-carbonyl]-amino}-bicyclo[2.2.1]heptane-2-carboxylic acid ethyl ester | 602.1 |
| 50 | (2R,3S)-3-{[1-(2,4-difluoro-phenyl)-(7S)-(3-fluoro-benzyl)-5,5-dioxo-4,5,6,7-tetrahydro-1H-5$\lambda^6$-thiopyrano[4,3-c]pyrazole-3-carbonyl]-amino}-bicyclo[2.2.1]heptane-2-carboxylic acid ethyl ester | 602.1 |
| 51 | 1-(2,4-difluoro-phenyl)-7-(3-fluoro-benzyl)-5,5-dioxo-4,5,6,7-tetrahydro-1H-5$\lambda^6$-thiopyrano[4,3-c]pyrazole-3-carboxylic acid [(1R,2S)-2-hydroxy-indan-1-yl]-amide | 568 |
| 53 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid N'-(2,4-dichloro-phenyl)-hydrazide | 627 |
| 65 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1S)-1-phenyl-ethyl]-amide | 570 |
| 66 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1R)-1-phenyl-ethyl]-amide | 570 |
| 67 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1R,2R)-2-hydroxy-cyclopentyl]-amide | 550 |
| 68 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1S,2S)-2-hydroxy-cyclohexyl]-amide | 564 |
| 69 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1R,2S)-2-hydroxy-indan-1-yl]-amide | 598 |
| 70 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1S,2R)-2-hydroxy-indan-1-yl]-amide | 598 |
| 71 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid amide | 465 |
| 73 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (pyridin-2-ylmethyl)-amide | 557.1 |

-continued

| Cpd | Name | MS |
|---|---|---|
| 81 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid piperidin-1-ylamide | 549.1 |
| 82 | (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid [(1R)-1-phenyl-ethyl]-amide | 571.1 |
| 83 | (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid piperidin-1-ylamide | 549 |
| 84 | (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid [(1R)-1-cyclohexyl-ethyl]-amide | 576.2 |
| 85 | (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid [(1S)-1-cyclohexyl-ethyl]-amide | 571.2 |
| 86 | (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid [(1S)-1-phenyl-ethyl]-amide | 571 |
| 87 | (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid (hexahydro-cyclopenta[c]pyrrol-2-yl)-amide | 575.1 |
| 95 | (7Z)-1-(4-chloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1R)-1-phenyl-ethyl]-amide | 536 |
| 97 | (7Z)-1-(4-chloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (hexahydro-cyclopenta[c]pyrrol-2-yl)-amide | 541 |
| 98 | (7Z)-[1-(4-chloro-phenyl)-7-(4-fluoro-benzylidene)-5,5-dioxo-4,5,6,7-tetrahydro-1H-5$\lambda^6$-thiopyrano[4,3-c]pyrazol-3-yl]-piperidin-1-yl-methanone | 499 |
| 99 | (7Z)-1-(4-chloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid piperidin-1-ylamide | 515 |
| 100 | (7Z)-1-(4-chloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid N'-methyl-N'-phenyl-hydrazide | 536.9 |
| 101 | (7Z)-[1-(2,4-dichloro-phenyl)-7-(4-fluoro-benzylidene)-5,5-dioxo-4,5,6,7-tetrahydro-1H-5$\lambda^6$-thiopyrano[4,3-c]pyrazol-3-yl]-piperidin-1-yl-methanone | 534 |
| 104 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (hexahydro-cyclopenta[c]pyrrol-2-yl)-amide | 576 |
| 105 | (7Z)-1-(2,4-difluoro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (hexahydro-cyclopenta[c]pyrrol-2-yl)-amide | 543.2 |
| 106 | (7Z)-1-(2,4-difluoro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid piperidin-1-ylamide | 517.2 |
| 107 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid azepan-1-ylamide | 563.1 |
| 108 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (2,6-dimethyl-piperidin-1-yl)-amide | 577 |
| 109 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (4-methyl-piperazin-1-yl)-amide | 566.1 |
| 110 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [4-(2-hydroxy-ethyl)-piperazin-1-yl]-amide | 595 |
| 117 | (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid [(1R)-1-phenyl-ethyl]-amide | 575.8 |
| 118 | (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid [(1R)-1-cyclohexyl-ethyl]-amide | 583.9 |
| 119 | (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid piperidin-1-ylamide | 554.8 |
| 120 | (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid azepan-1-ylamide | 569.1 |
| 121 | (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid (hexahydro-cyclopenta[c]pyrrol-2-yl)-amide | 581 |

-continued

| Cpd | Name | MS |
|---|---|---|
| 124 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1R)-1-(pyridin-2-yl)-ethyl]-amide | 571 |
| 125 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(2S)-2-(methoxymethyl)-pyrrolidin-1-yl]-amide | 579 |
| 126 | (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(2R)-2-(methoxymethyl)-pyrrolidin-1-yl]-amide | 579 |
| 128 | 1-(2,4-dichloro-phenyl)-5,5-dioxo-4,5,6,7-tetrahydro-1H-5$\lambda^6$-thiopyrano[4,3-c]pyrazole-3-carboxylic acid [(1R)-1-phenyl-ethyl]-amide | 464 |

EXAMPLE 4

(E)-2-(1-benzyl-1,4,6,7-tetrahydro-thiopyrano[4-3-c]pyrazol-3-yl)-ethenesulfonic acid [(1S)-1-phenyl-ethyl]-amide (Cpd 3)

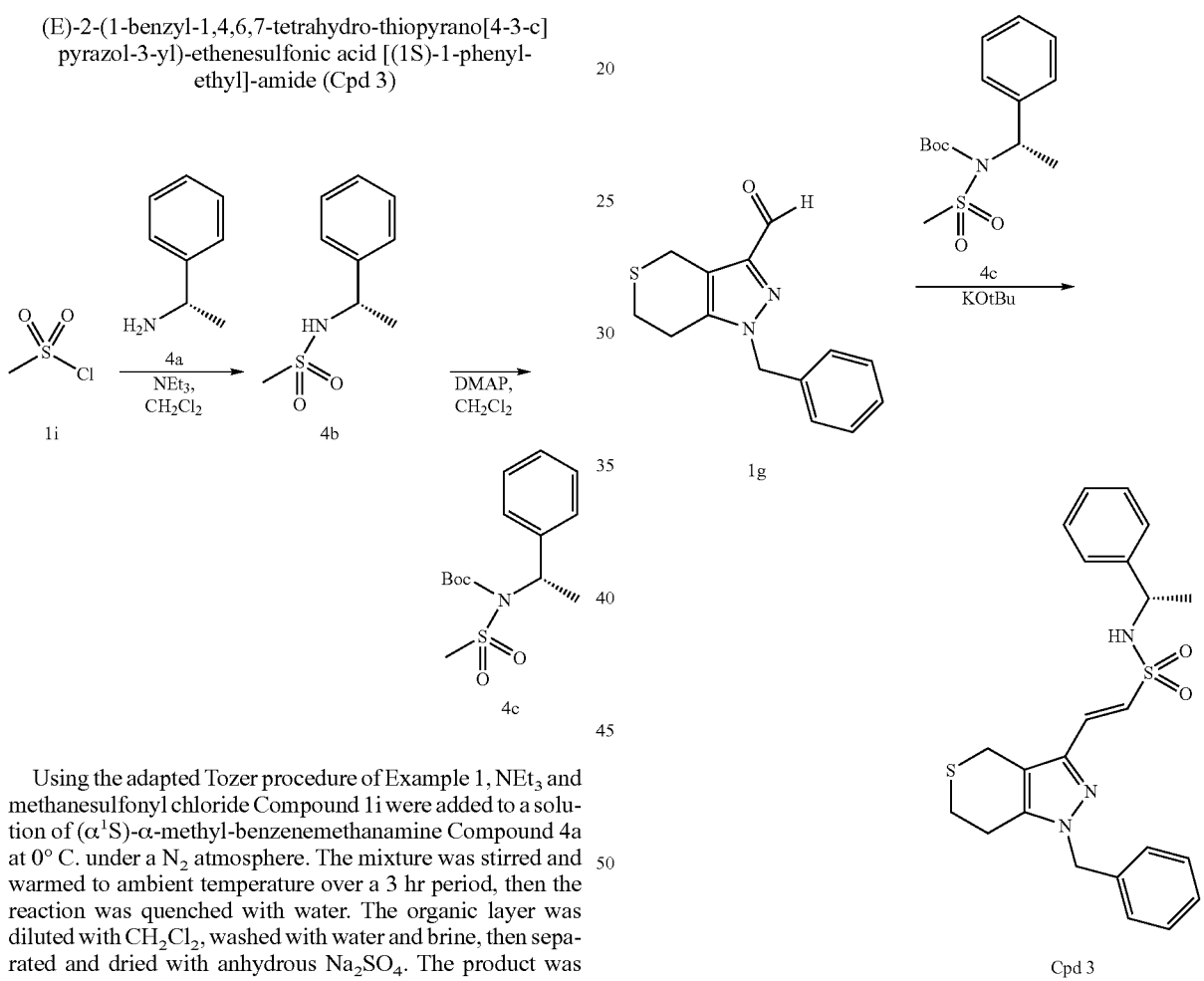

Using the adapted Tozer procedure of Example 1, NEt$_3$ and methanesulfonyl chloride Compound 1i were added to a solution of ($\alpha^1$S)-$\alpha$-methyl-benzenemethanamine Compound 4a at 0° C. under a N$_2$ atmosphere. The mixture was stirred and warmed to ambient temperature over a 3 hr period, then the reaction was quenched with water. The organic layer was diluted with CH$_2$Cl$_2$, washed with water and brine, then separated and dried with anhydrous Na$_2$SO$_4$. The product was filtered and concentrated in vacuo to afford a N-[(1S)-1-phenyl-ethyl)methanesulfonamide Compound 4b as an oil.

Di-t-butyl-dicarbonate and DMAP were added to a solution of Compound 4b in CH$_2$Cl$_2$ at 0° C. under a N$_2$ atmosphere. The mixture was stirred and warmed to ambient temperature overnight, then the reaction was quenched with a saturated solution of NaHCO$_3$. The organic layer was diluted with CH$_2$Cl$_2$ and washed with water and brine, separated and dried with anhydrous Na$_2$SO$_4$, then filtered and concentrated in vacuo to yield a crude product, which was purified by flash chromatography (eluted with 10% EtOAc in hexane) to afford N-(t-butoxy carbonyl)-N-[(1S)1-phenyl-ethyl]-methanesulfonamide Compound 4c as a colorless oil.

A 1M solution of KOtBu in THF (0.80 mL, 0.80 mmol) was added dropwise to a solution of methanesulfonamide Compound 4c (0.120 mg, 0.40 mmol) in anhydrous THF (10 mL) at -78° C. under a N$_2$ atmosphere. The mixture was stirred for about 45 min, then carbaldehyde Compound 1g (0.100 g, 0.4 mmol) diluted in THF (3 mL) was added dropwise. The mixture was warmed to ambient temperature over a 15 hr period, then the reaction was quenched with water (5 mL). The organic layer was diluted with EtOAc (100 mL), washed with water and brine, separated and dried with anhydrous Na$_2$SO$_4$, then filtered and concentrated in vacuo to yield a crude product, which was purified by flash chromatography (eluted with 20% EtOAc in hexane) to give Compound 3 (0.134 g, 76%) as a white solid. MS m/z 440.1 (MH⁺).

Using the procedure of Example 4, other compounds that are representative of the invention may be prepared by varying the starting materials, reagent(s) and conditions used, such as:

| Cpd | Name | MS |
|---|---|---|
| 12 | (E)-2-(1-benzyl-1,4,6,7-tetrahydro-thiopyrano[4,3-c]pyrazol-3-yl)-ethenesulfonic acid [(1S)-1-cyclohexyl-ethyl]-amide | 446.1 |

EXAMPLE 5

(E)-2-(2-benzyl-2,4,6,7-tetrahydro-thiopyrano[4,3-c]pyrazol-3-yl)-ethenesulfonic acid [(1R)-1-phenyl-ethyl]-amide (Cpd 2)

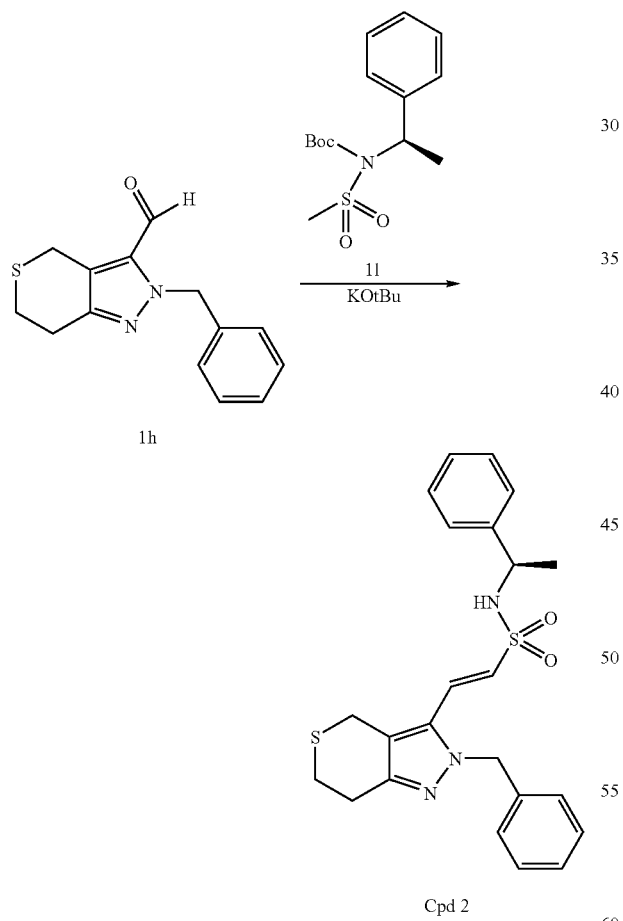

A 1M solution of KOtBu in THF (0.75 mL, 0.75 mmol) was added dropwise to a solution of Compound 11 (0.050 g, 0.250 mmol) in anhydrous THF (5 mL) at −78° C. under a N₂ atmosphere. After 45 min, 2-benzyl-2,4,6,7-tetrahydro-thiopyrano[4,3-c]pyrazole-3-carbaldehyde Compound 1h (0.116 g, 0.250 mmol) diluted in THF (3 mL) was added dropwise. The solution was warmed to ambient temperature over a 15 hr period, then the reaction was quenched with water (5 mL). The organic layer was diluted with EtOAc (100 mL) and washed with water and brine, separated and dried with anhydrous Na₂SO₄, then filtered and concentrated in vacuo to yield a crude product, which was purified by flash chromatography (eluted with 20% EtOAc in hexane) to give Compound 2 (0.082 g, 75%) as a white solid. MS m/z 440.1 (MH⁺).

Using the procedure of Example 5, other compounds that are representative of the invention may be prepared by varying the starting materials, reagent(s) and conditions used, such as:

| Cpd | Name | MS |
|---|---|---|
| 6 | (E)-2-(2-benzyl-2,4,6,7-tetrahydro-thiopyrano[4,3-c]pyrazol-3-yl)-ethenesulfonic acid [(1R)-1-cyclohexyl-ethyl]-amide | 446.3 |

EXAMPLE 6

(E)-2-(2-benzyl-2,4,6,7-tetrahydro-thiopyrano[4,3-c]pyrazol-3-yl)-ethenesulfonic acid [(1S)-1-phenyl-ethyl]-amide (Cpd 5)

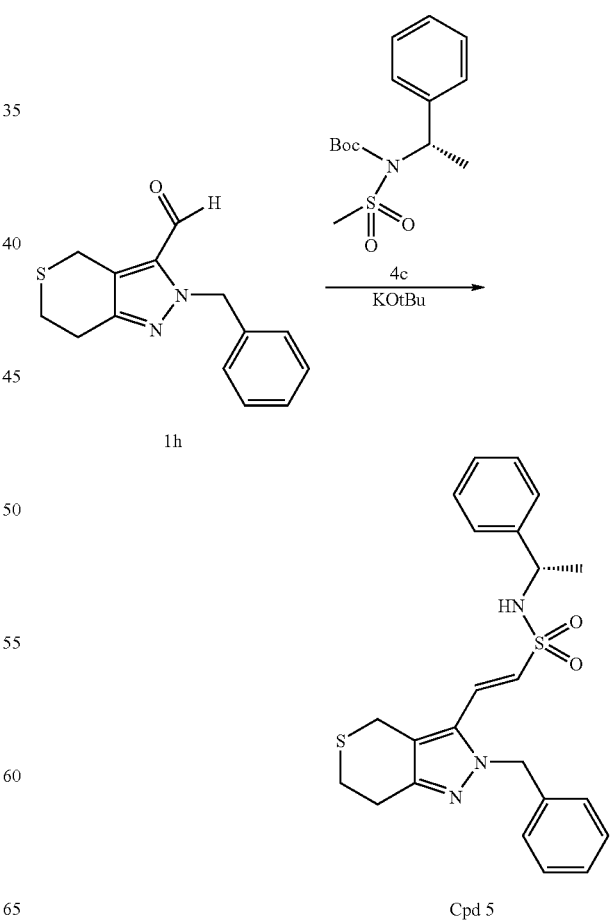

A 1M solution of KOtBu in THF (1.6 mL, 1.6 mmol) was added dropwise to a solution of methanesulfonamide Compound 4c (0.220 g, 0.74 mmol) in anhydrous THF (10 mL) at −78° C. under a $N_2$ atmosphere. After 45 mins, carbaldehyde Compound 1h (0.190 g, 0.74 mmol) diluted in THF (3 mL) was added dropwise. The solution was warmed to ambient temperature and the reaction was quenched with water (5 mL). The organic layer was diluted with EtOAc (100 mL) and washed with water and brine, separated and dried with anhydrous $Na_2SO_4$, then filtered and concentrated in vacuo to yield a crude product, which was purified by flash chromatography (eluted with 20% EtOAc in hexane) to give Compound 5 (0.230 g, 71%). MS m/z 440.1 ($MH^+$).

Using the procedure of Example 6, other compounds that are representative of the invention may be prepared by varying the starting materials, reagent(s) and conditions used, such as:

| Cpd | Name | MS |
|---|---|---|
| 8 | (E)-2-(2-benzyl-2,4,6,7-tetrahydro-thiopyrano[4,3-c]pyrazol-3-yl)-ethenesulfonic acid [(1S)-1-phenyl-ethyl]-amide | 446.1 |

EXAMPLE 7

(2E)-3-(1-benzyl-1,4,6,7-tetrahydro-thiopyrano[4,3-c]pyrazol-3-yl)-N-[(1S)-1-phenyl-ethyl]-acrylamide (Cpd 32)

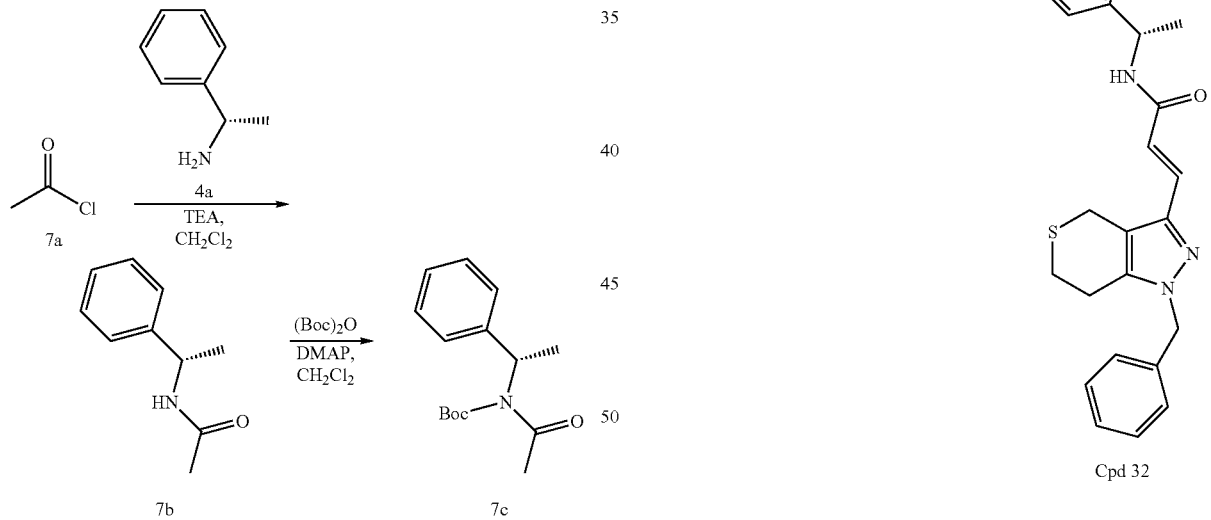

Acetyl chloride Compound 7a (0.70 g, 8.90 mmol) and TEA (0.90 g) were added to a solution of ($\alpha^1$S)-α-methyl-benzenemethanamine Compound 4a (1.0 g, 8.2 mmol) in $CH_2Cl_2$ (12 mL) at 0° C. under a $N_2$ atmosphere. The mixture was stirred and warmed to r.t. over a 2 hr period, then the reaction was quenched with water (50 mL). The organic layer was diluted with $CH_2Cl_2$ (50 mL) and washed with water and brine, separated and dried with anhydrous $Na_2SO_4$, then filtered and concentrated in vacuo to afford the corresponding N-(1S)-1-phenyl-ethylacetamide Compound 7b as an oil.

$(Boc)_2O$ (1.48 g, 6.45 mmol) and DMAP (100 mg) were added to a solution of the acetamide Compound 7b in $CH_2Cl_2$ (16 mL) at 0° C. under a $N_2$ atmosphere. The mixture was stirred and warmed to r.t. overnight, then the reaction was quenched with a saturated solution of $NaHCO_3$ (10 mL). The organic layer was diluted with $CH_2Cl_2$ (50 mL) and washed with water and brine, separated and dried with anhydrous $Na_2SO_4$, then filtered and concentrated in vacuo to yield a crude product, which was purified by flash chromatography (eluted with 20% EtOAc in hexane) to afford acetyl-(1S)-1-phenyl-ethyl-carbamic acid tert-butyl ester Compound 7c (0.4 g, 24%) as an oil.

Using the adapted Tozer procedure of Example 1, a 1M solution of KOtBu in THF (1.2 mL, 1.2 mmol) was added dropwise to a solution of Compound 7c (0.08 g, 0.30 mmol) in anhydrous THF (6 mL) at −78° C. under a $N_2$ atmosphere. After about 30 min, Compound 1g (0.07 g, 0.30 mmol) diluted in THF (2 mL) was added dropwise. The mixture was stirred and warmed to r.t. over an 18 hr period, then the reaction was quenched with water (2 mL). The organic layer was diluted with EtOAc (10 mL) and washed with water and brine, separated and dried with anhydrous $Na_2SO_4$, then filtered and concentrated in vacuo to yield a crude product, which was purified by flash chromatography (eluted with 25% EtOAc in hexane) to give Compound 32 (0.093 g, 77%) as a solid. MS m/z 403.1 (MH⁺).

EXAMPLE 8

(2E)-3-(1-benzyl-1,4,6,7-tetrahydro-thiopyrano[4,3-c]pyrazol-3-yl)-N-[(1R)-1-phenyl-ethyl]-acrylamide (Cpd 33)

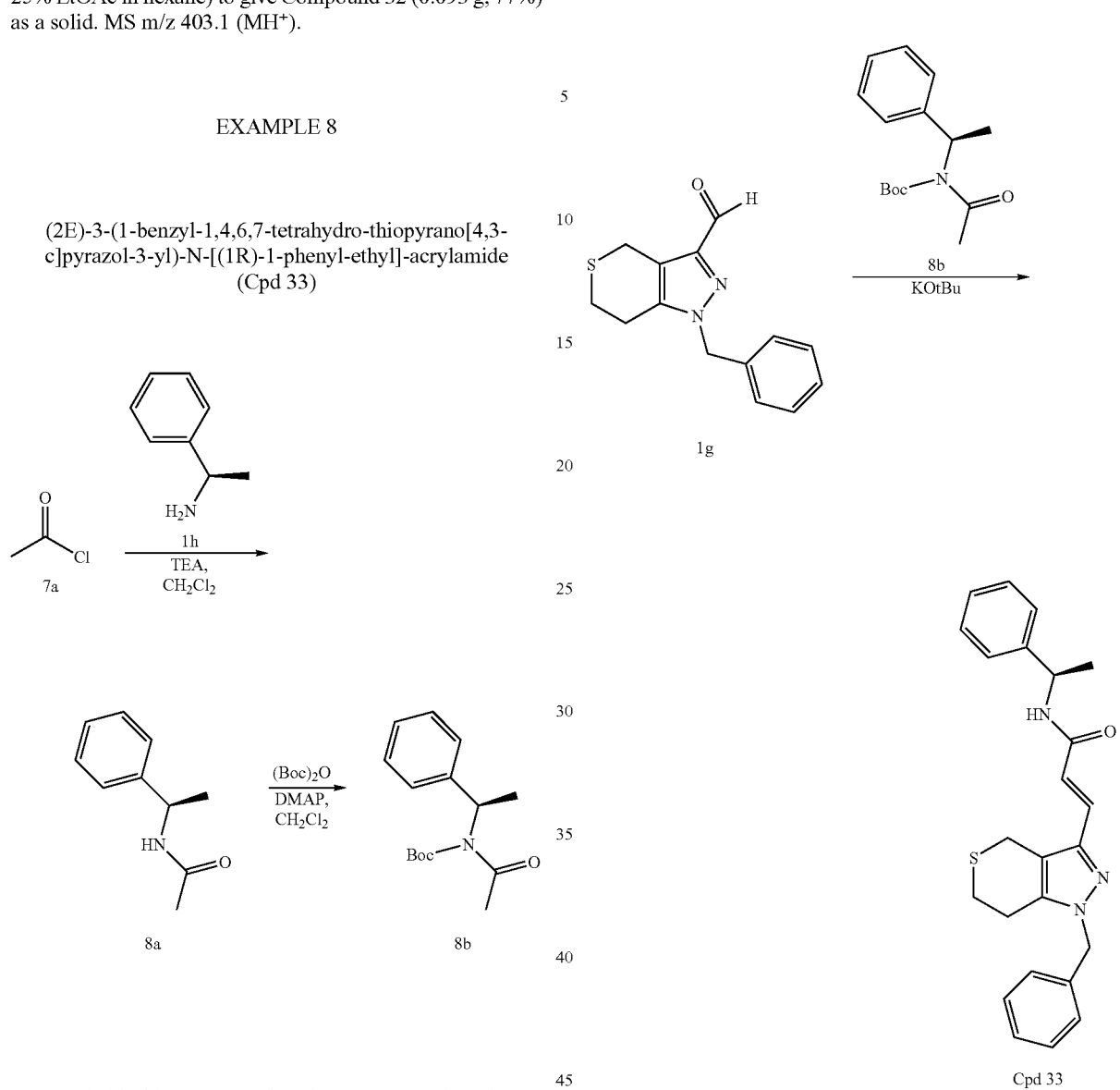

Acetyl chloride Compound 7a (0.8 g, 10 mmol) and TEA were added to a solution of (α¹R)-α-methyl-benzenemethanamine Compound 1h (1.2 g, 10 mmol) in CH₂Cl₂ (12 mL) at 0° C. under a N₂ atmosphere. The mixture was stirred and warmed to r.t., then the reaction was quenched with water (30 mL). The organic layer was diluted with CH₂Cl₂ (50 mL) and washed with water and brine, separated and dried with anhydrous Na₂SO₄, then filtered and concentrated in vacuo to afford the corresponding N-(1S)-1-phenyl-ethyl-acetamide Compound 8a as oil.

(Boc)₂O (2.18 g) and DMAP (100 mg) were added to a solution of the acetamide Compound 8a in CH₂Cl₂ (16 mL) at 0° C. under a N₂ atmosphere. The mixture was stirred overnight while warming to r.t., then the reaction was quenched with a saturated solution of NaHCO₃ (10 mL). The organic layer was diluted with CH₂Cl₂ (50 mL) and washed with water and brine, separated and dried with anhydrous Na₂SO₄, then filtered and concentrated in vacuo to yield a crude product, which was purified by flash chromatography (eluted with 20% EtOAc in hexane) to afford acetyl-(1S)-1-phenyl-ethyl-carbamic acid tert-butyl ester Compound 8b (0.6 g, 23%) as an oil.

Using the adapted Tozer procedure of Example 1, a solution of KOtBu in THF (2.5 mL, 2.5 mmol) was added dropwise to a solution of the tert-butyl ester Compound 8b (0.26 g, 1.0 mmol) in anhydrous THF (10 mL) at −78° C. under a N₂ atmosphere. After 45 min, Compound 1g (0.25 g, 1.0 mmol) diluted in THF (3 mL) was added dropwise. The mixture was stirred and warmed to r.t. over an 18 hr period, then the reaction was quenched with water (10 mL). The organic layer was diluted with EtOAc (100 mL) and washed with water and brine, separated and dried with anhydrous Na₂SO₄, then filtered and concentrated in vacuo to yield a crude product, which was purified by flash chromatography (eluted with 25% EtOAc in hexane) to give Compound 33 (0.25 g, 62%) as a solid. MS m/z 404.1 (MH⁺).

EXAMPLE 9

(E)-2-[7-(3-fluoro-benzyl)-1,4,6,7-tetrahydro-thiopyrano[4,3-c]pyrazol-3-yl]-ethenesulfonic acid [(1S)-1-phenyl-ethyl]-amide (Cpd 47)

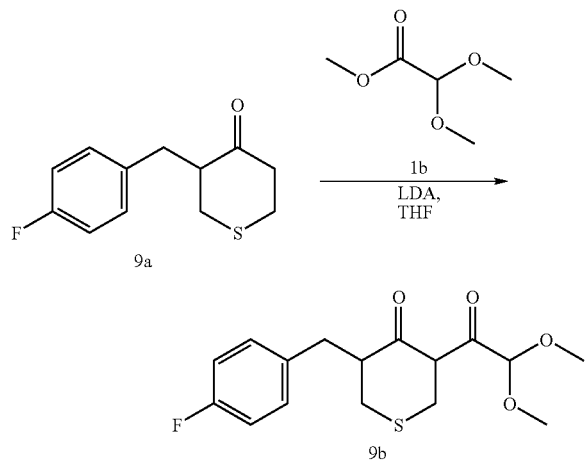

3-(3-Fluoro-phenyl)-tetrahydro-4H-thiopyran-4-one Compound 9a (2.24 g, 10 mmol) was added dropwise to a solution of LDA in anhydrous THF (60 mL) at −78° C. under a $N_2$ atmosphere. The mixture was stirred at −78° C. for 30 mins, and dimethoxy-acetic acid methyl ester Compound 1b (1.3 g, 10 mmol) in anhydrous THF (5 mL) was added dropwise. The solution was stirred and warmed to r.t. over a 12 hr period, then the reaction was quenched with water (10 mL). The organic layer was diluted with EtOAc (100 mL) and washed with water and brine, separated and dried with anhydrous $Na_2SO_4$, then filtered and concentrated in vacuo to yield a crude oil, which was purified by flash chromatography (eluted with 5% EtOAc in hexane) to afford 3-(2,2-dimethoxy-acetyl)-5-(3-fluoro-phenyl)-tetrahydro-4H-thiopyran-4-one Compound 9b (2.1 g, 64%) as an oil.

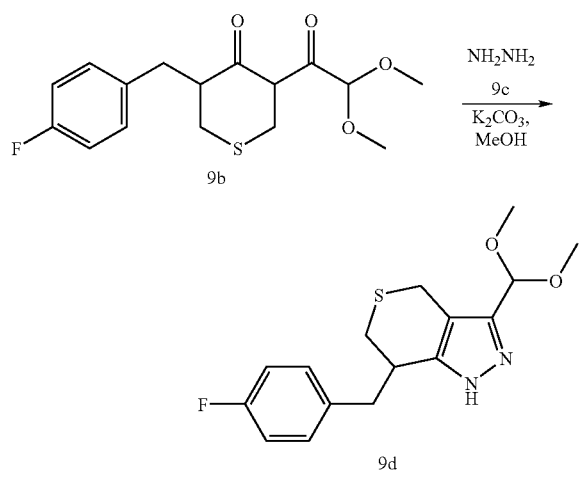

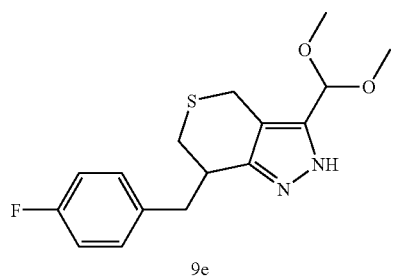

Hydrazine Compound 9c (0.2 g, 6.5 mmol) was added to a solution of Compound 9b (2.1 g, 6.4 mmol) in MeOH (60 mL) at 0° C. under a $N_2$ atmosphere. The solution was stirred and warmed to r.t. over a 16 hr period. The reaction was quenched with water (50 mL) and diluted with EtOAc (100 mL). The organic layer was washed with water and brine, separated and dried with anhydrous $Na_2SO_4$, then filtered and concentrated in vacuo to yield a crude oil, which was purified by flash chromatography (eluted with 30% EtOAc in hexane) to afford a white solid mixture of 3-dimethoxymethyl-7-(4-fluoro-benzyl)-1,4,6,7-tetrahydro-thiopyrano[4,3-c]pyrazole Compound 9d (1.2 g, 57%) as the major isomer and 3-dimethoxymethyl-7-(4-fluoro-benzyl)-2,4,6,7-tetrahydro-thiopyrano[4,3-c]pyrazole Compound 9e as the minor isomer.

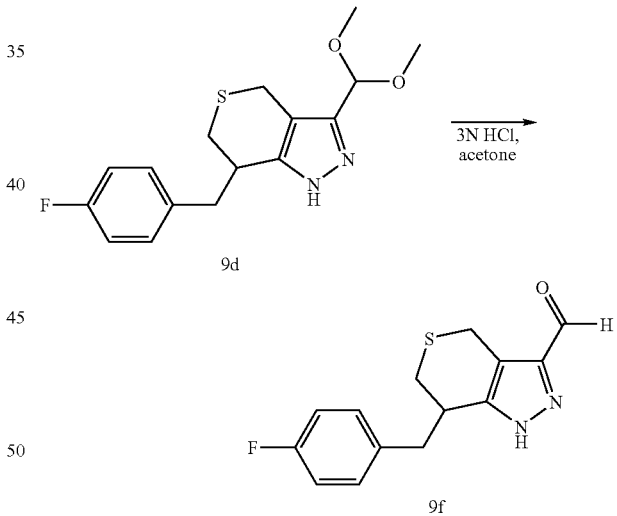

3N HCl (1.0 mL) was added to a solution of the mixture of Compound 9d (1.2 g, 3.7 mmol) in acetone (40 mL) at 0° C. under a $N_2$ atmosphere. The solution was stirred and warmed to r.t. over a 2 hr period. The reaction was neutralized to pH 7 with $K_2CO_3$ and diluted with $CH_2Cl_2$ (60 mL). The organic layer was washed with water and brine, separated and dried with anhydrous $Na_2SO_4$, then filtered and concentrated in vacuo to yield a crude oil, which was purified by flash chromatography (eluted with 10% EtOAc in hexane) to yield 7-(3-fluorophenyl)-1,4,6,7-tetrahydro-thiopyrano[4,3-c]pyrazole-3-carbaldehyde Compound 9f (0.95 g, 93%) as a solid.

EXAMPLE 10

(E)-2-[1-(2,4-difluoro-phenyl)-7-(3-fluoro-benzyl)-1,4,6,7-tetrahydro-thiopyrano[4,3-c]pyrazol-3-yl]-ethenesulfonic acid [(1S)-1-phenyl-ethyl]-amide (Cpd 38)

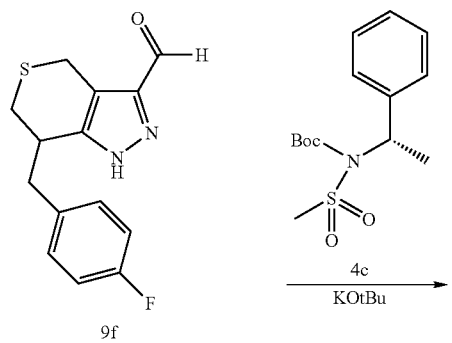

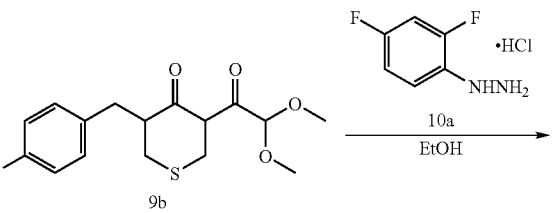

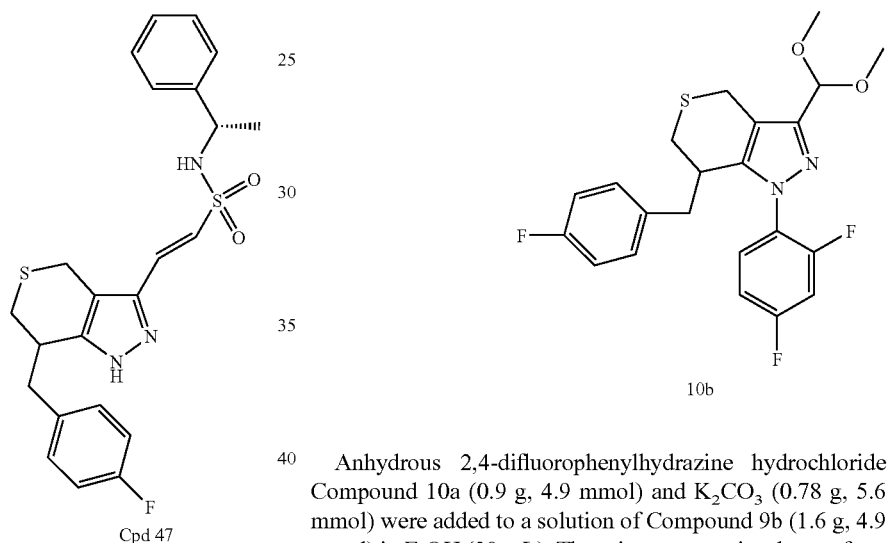

Anhydrous 2,4-difluorophenylhydrazine hydrochloride Compound 10a (0.9 g, 4.9 mmol) and K$_2$CO$_3$ (0.78 g, 5.6 mmol) were added to a solution of Compound 9b (1.6 g, 4.9 mmol) in EtOH (20 mL). The mixture was stirred at r.t. for a 16 hr period, filtered and washed with EtOH, then concentrated and purified on a silica gel column (eluted with 20% EtOAc in hexane) to afford Compound 10b (1.34 g, 62%) as a white solid.

A 1.0M solution of KOtBu in THF (1.7 mL, 1.7 mmol) was added dropwise to a solution of methanesulfonamide Compound 4c (0.21 g, 0.70 mmol) in anhydrous THF (15 mL) at −78° C. under a N$_2$ atmosphere. The mixture was stirred for about 30 min, then carbaldehyde Compound 9f (0.19 g, 0.70 mmol) diluted in THF (3 mL) was added dropwise. The mixture was warmed to ambient temperature over an 18 hr period, then the reaction was quenched with water (10 mL). The organic layer was diluted with EtOAc (100 mL) and washed with water and brine, separated and dried with anhydrous Na$_2$SO$_4$, then filtered and concentrated in vacuo to yield a crude product, which was purified by flash chromatography (eluted with 25% EtOAc in hexane) to provide Compound 47 (0.20 g, 65%) as a white solid. MS m/z 458 (MH$^+$).

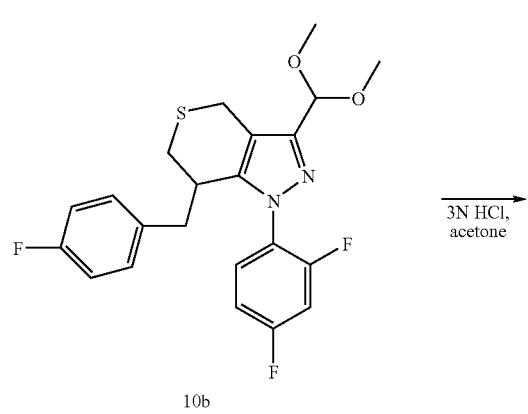

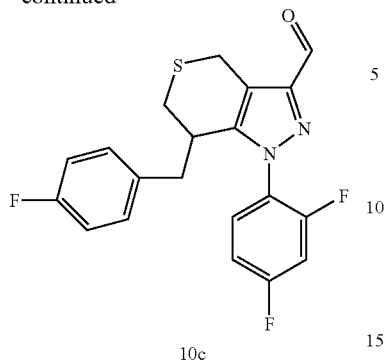

10c

3N HCl (2 mL) was added to a solution of Compound 10b (1.34 g, 3.1 mmol) in acetone (20 mL) at 0° C. under a $N_2$ atmosphere. The solution was stirred and warmed to r.t. over a 3 hr period. The reaction was quenched with water (10 mL), neutralized to pH 7 with $K_2CO_3$ and diluted with $CH_2Cl_2$ (60 mL). The organic layer was washed with water and brine, separated and dried with anhydrous $Na_2SO_4$, then filtered and concentrated in vacuo to yield a crude oil, which was purified by flash chromatography (eluted with 10% EtOAc in hexane) to yield 1-(2,4-difluoro-phenyl)-7-(3-fluoro-phenyl)-1,4,6,7-tetrahydro-thiopyrano[4,3-c]pyrazole-3-carbaldehyde Compound 10c (1.1 g, 91%) as a white solid.

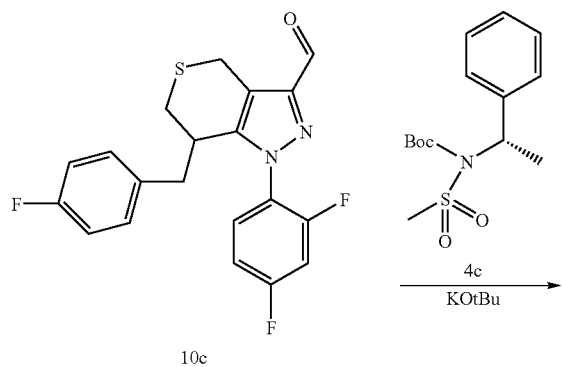

A 1.0M solution of KOtBu in THF (0.4 mL, 0.4 mmol) was added dropwise to a solution of methanesulfonamide Compound 4c (0.045 g, 0.15 mmol) in anhydrous THF (5 mL) at −78° C. under a $N_2$ atmosphere. The mixture was stirred for 45 min, then carbaldehyde Compound 10c (0.06 g, 0.15 mmol) diluted in THF (2.5 mL) was added dropwise. The mixture was warmed to ambient temperature over an 18 hr period, then the reaction was quenched with water (5 mL). The organic layer was diluted with EtOAc (25 mL) and washed with water and brine, separated and dried with anhydrous $Na_2SO_4$, then filtered and concentrated in vacuo to yield a crude product, which was purified by flash chromatography (eluted with 25% EtOAc in hexane) to provide Compound 38 (0.058 g, 68%) as a white solid. MS m/z 570.2 ($MH^+$).

Using the procedure of Example 10, other compounds that are representative of the invention may be prepared by varying the starting materials, reagent(s) and conditions used, such as:

| Cpd | Name | MS |
|---|---|---|
| 39 | (E)-2-[1-(2,4-difluoro-phenyl)-7-(3-fluoro-benzyl)-1,4,6,7-tetrahydro-thiopyrano[4,3-c]pyrazol-3-yl]-ethenesulfonic acid [(1R)-1-cyclohexyl-ethyl]-amide | 576 |
| 40 | (E)-2-[1-(2,4-difluoro-phenyl)-7-(3-fluoro-benzyl)-1,4,6,7-tetrahydro-thiopyrano[4,3-c]pyrazol-3-yl]-ethenesulfonic acid piperidin-1-ylamide | 549.2 |
| 46 | (E)-2-[7-(3-chloro-benzyl)-1-(2,4-dichloro-phenyl)-1,4,6,7-tetrahydro-thiopyrano[4,3-c]pyrazol-3-yl]-ethenesulfonic acid [(1S)-1-phenyl-ethyl]-amide | 619 |
| 48 | (E)-2-[7-(3-fluoro-benzyl)-1,4,6,7-tetrahydro-thiopyrano[4,3-c]pyrazol-3-yl]-ethenesulfonic acid [(1R)-1-cyclohexyl-ethyl]-amide | 464.1 |

EXAMPLE 11

(E)-2-[1-(2,4-difluoro-phenyl)-7-(3-fluoro-benzyl)-1,4,6,7-tetrahydro-thiopyrano[4,3-c]pyrazol-3-yl]-ethenesulfonic acid morpholin-4-ylamide (Cpd 41)

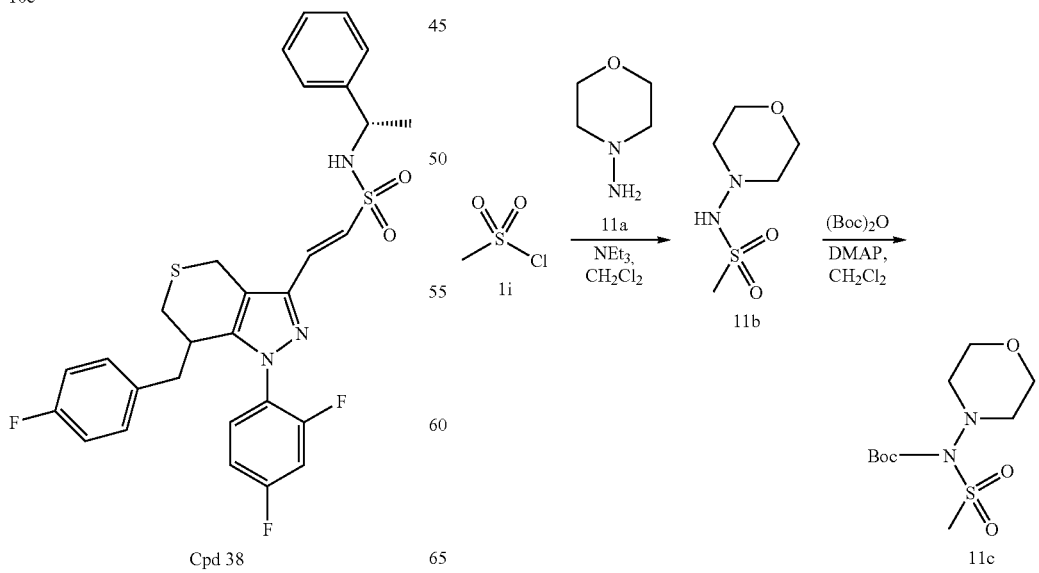

Using the adapted Tozer procedure of Example 1, NEt$_3$ (2.8 mL) and methanesulfonyl chloride Compound 1i (2.3 g, 20.0 mmol) were added to a solution of morpholin-4-ylamine Compound 11a (2.1 g, 20.0 mmol) in 20 mL of CH$_2$Cl$_2$ at 0° C. under a N$_2$ atmosphere. The mixture was stirred and warmed to ambient temperature over a 2 hr period, then the reaction was quenched with water (10 mL). The organic layer was diluted with CH$_2$Cl$_2$ (60 mL) and washed with water and brine, separated and dried with anhydrous Na$_2$SO$_4$, then filtered and concentrated in vacuo to afford N-morpholin-4-yl-methanesulfonamide Compound 11b as an oil.

(Boc)$_2$O (4.70 g) and DMAP (0.10 g) were added to a solution of Compound 11b in CH$_2$Cl$_2$ (30 mL) at 0° C. under a N$_2$ atmosphere. The mixture was stirred and warmed to ambient temperature overnight, then the reaction was quenched with a saturated solution of NaHCO$_3$ (20 mL). The organic layer was diluted with CH$_2$Cl$_2$ (60 mL) and washed with water and brine, separated and dried with anhydrous Na$_2$SO$_4$, then filtered and concentrated in vacuo to yield a crude product, which was purified by flash chromatography (eluted with 10% EtOAc in hexane) to afford N-(t-butoxy carbonyl)-N-morpholin-4-yl-methanesulfonamide Compound 11c (4.5 g, 81%) as a white solid.

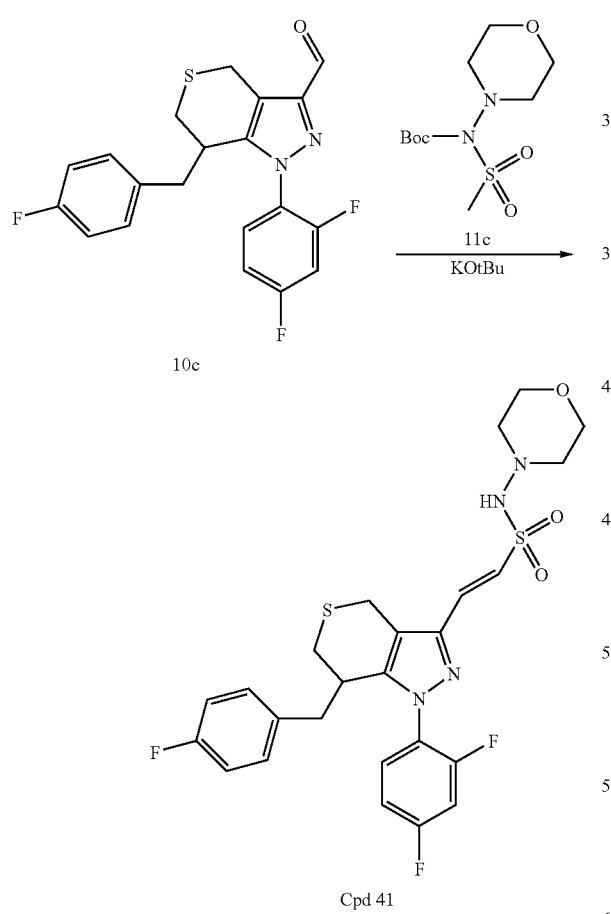

A 1.0M solution of KOtBu in THF (0.4 mL, 0.4 mmol) was added dropwise to a solution of methanesulfonamide Compound 11c (0.042 g, 0.15 mmol) in anhydrous THF (5 mL) at −78° C. under a N$_2$ atmosphere. The mixture was stirred for about 45 min, then carbaldehyde Compound 10c (0.06 g, 0.15 mmol) diluted in THF was added dropwise. The mixture was warmed to ambient temperature and the reaction was quenched with water. The organic layer was diluted with EtOAc and washed with water and brine, separated and dried with anhydrous Na$_2$SO$_4$, then filtered and concentrated in vacuo to yield a crude product, which was purified by flash chromatography to provide Compound 41. MS m/z 551.1 (MH$^+$).

EXAMPLE 12

(7Z)-[1-(2,4-dichloro-phenyl)-7-(4-fluoro-benzylidene)-1,4,6,7-tetrahydro-thiopyrano[4,3-c]pyrazol-3-yl]-piperidin-1-yl-methanone (Cpd 55)

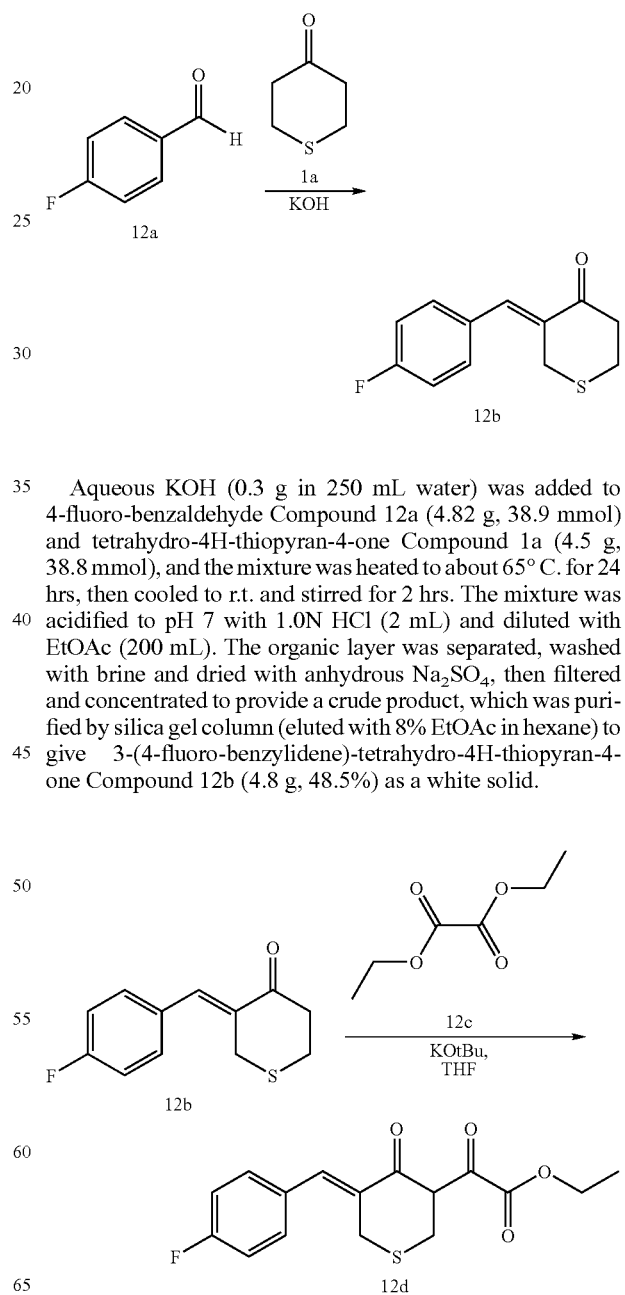

Aqueous KOH (0.3 g in 250 mL water) was added to 4-fluoro-benzaldehyde Compound 12a (4.82 g, 38.9 mmol) and tetrahydro-4H-thiopyran-4-one Compound 1a (4.5 g, 38.8 mmol), and the mixture was heated to about 65° C. for 24 hrs, then cooled to r.t. and stirred for 2 hrs. The mixture was acidified to pH 7 with 1.0N HCl (2 mL) and diluted with EtOAc (200 mL). The organic layer was separated, washed with brine and dried with anhydrous Na$_2$SO$_4$, then filtered and concentrated to provide a crude product, which was purified by silica gel column (eluted with 8% EtOAc in hexane) to give 3-(4-fluoro-benzylidene)-tetrahydro-4H-thiopyran-4-one Compound 12b (4.8 g, 48.5%) as a white solid.

An oxalic acid di-ethyl ester Compound 12c (1.43 g, 10 mmol) in THF (5 mL) was added to a solution of Compound 12b (2.2 g, 10 mmol) in THF (60 mL) at 0° C. followed by the dropwise addition of a 1.0M solution of KOtBu in THF (16.0 mL, 16.0 mmol). The mixture was allowed to warm to r.t. over a 2 hr period, then the reaction was quenched with 1N HCl (2 mL). The organic layer was extracted with $Et_2O$ (100 mL) and washed with brine, separated and dried with anhydrous $Na_2SO_4$, then filtered and concentrated in vacuo to yield a [5-(4-fluoro-benzylidene)-4-oxo-tetrahydro-thiopyran-3-yl]-oxo-acetic acid ethyl ester Compound 12d as a brown solid. Compound 12d was used in the next step without further purification.

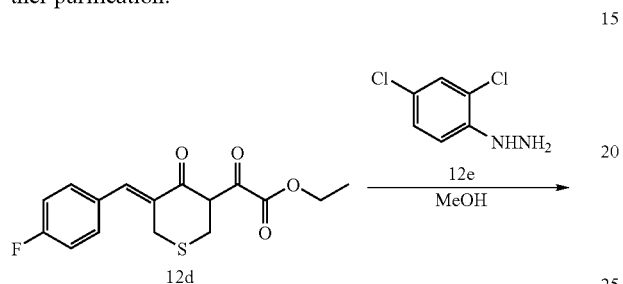

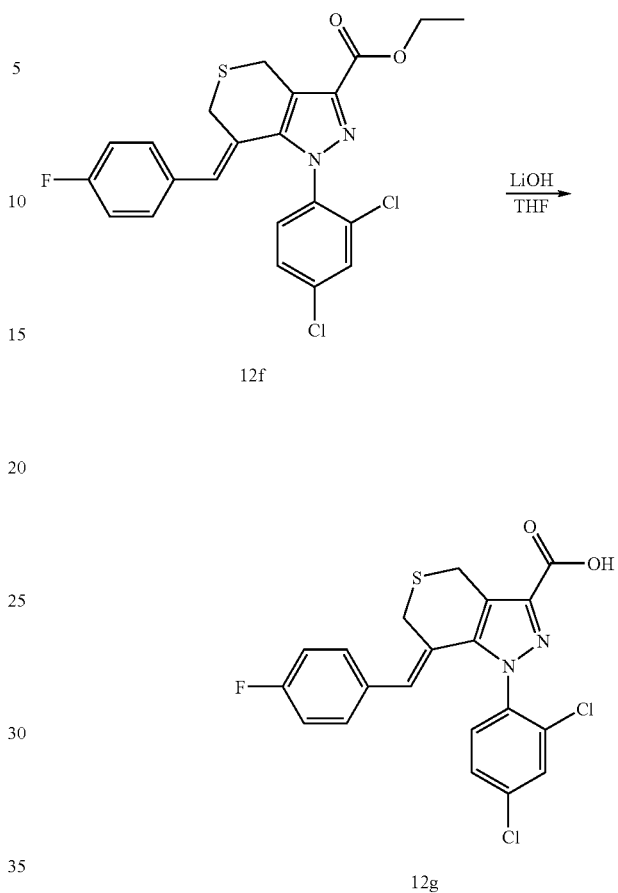

2,4-Dichloro-phenyl-hydrazine Compound 12e (10.8 g, 10 mmol) was added to a solution of Compound 12d (3.38 g, 10.1 mmol) in MeOH (60 mL) at ambient temperature under a $N_2$ atmosphere. The mixture was stirred overnight, and 1 mL of concentrated HCl was added. The reaction mixture was allowed to stir for an additional 6 hrs, concentrated to dryness and then purified by flash chromatography (eluted with 15% EtOAc in hexane) to afford 1-(2,4-dichloro-phenyl)-7-(4-fluoro-benzylidene)-1,4,6,7-tetrahydro-thiopyrano[4,3-c]pyrazole-3-carboxylic acid ethyl ester Compound 12f (2.4 g, 51%) as a solid.

LiOH (1.2 equiv) was added to compound 12f (2.4 g, 5.1 mmol) in a 9:3:1 mixture of THF (65 mL), EtOH (21 mL) and water (7 mL). The mixture was stirred for 24 hrs, acidified to about pH 3 with 1N HCl and extracted with EtOAc (100 mL). The organic layer was washed with brine and dried over $Na_2SO_4$, then filtered and concentrated in vacuo to yield Compound 12g (2.05 g, 93%) as a white solid.

| Cpd | Name | MS |
|---|---|---|
| 1 | 1-benzyl-1,4,6,7-tetrahydro-thiopyrano[4,3-c]pyrazole-3-carboxylic acid [(1R)-1-phenyl-ethyl]-amide | 378 |
| 19 | 1-benzyl-1,4,6,7-tetrahydro-thiopyrano[4,3-c]pyrazole-3-carboxylic acid (1,3,3-trimethyl-bicyclo[2.2.1]hept-2-yl)-amide | 410 |
| 57 | (7Z)-[1-(2,4-dichloro-phenyl)-7-(4-fluoro-benzylidene)-1,4,6,7-tetrahydro-thiopyrano[4,3-c]pyrazol-3-yl]-pyrrolidin-1-yl-methanone | 488 |

EXAMPLE 13

(7Z)-1-(2,4-dichloro-phenyl)-7-(4-fluoro-benzylidene)-1,4,6,7-tetrahydro-thiopyrano[4,3-c]pyrazole-3-carboxylic acid piperidin-1-ylamide (Cpd 54)

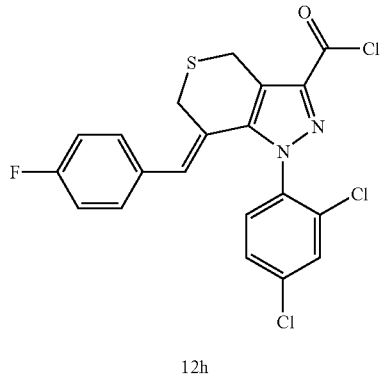

12h

Thionyl chloride (1.8 g, 15 mmol) was added to a solution of Compound 12g (2.0 g) in $CH_2Cl_2$ at ambient temperature under a $N_2$ atmosphere. The reaction was stirred for 12 hrs and concentrated in vacuo to afford an acid chloride Compound 12h.

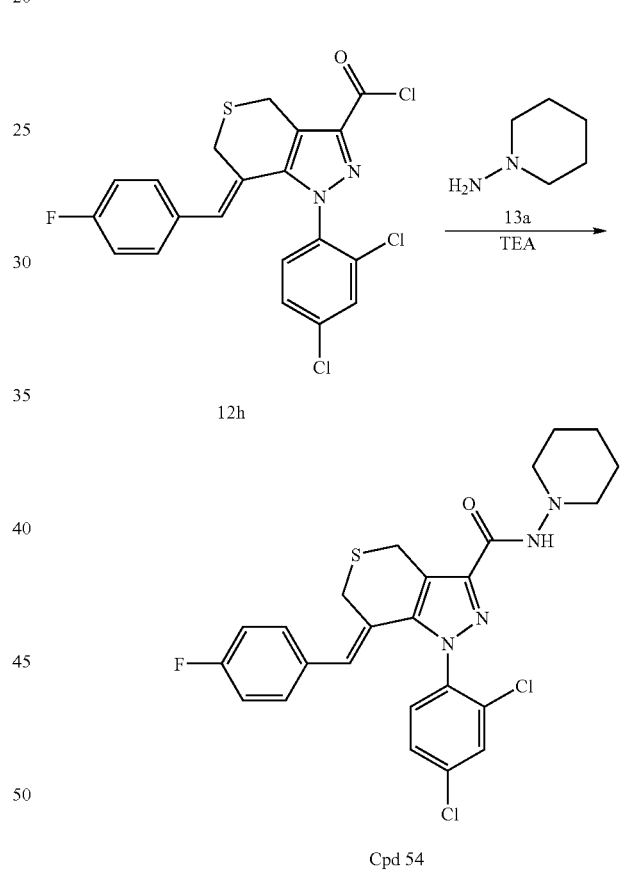

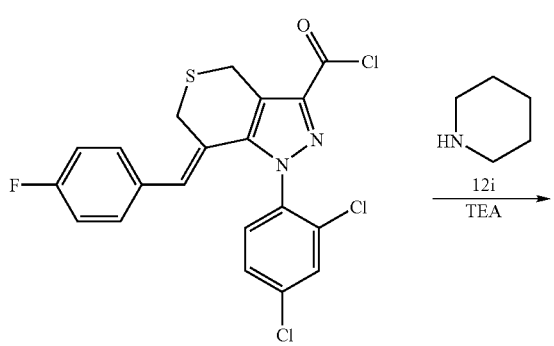

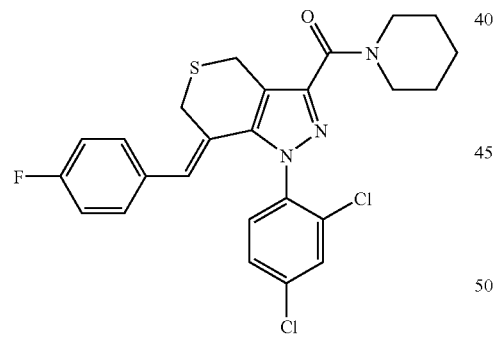

Cpd 55

Compound 12h (0.05 g, 0.10 mmol) was added to a solution of piperidine Compound 12i (0.011 g, 0.11 mmol) in $CH_2Cl_2$ (5 mL) and TEA (0.14 mL, 0.12 mmol). The suspension was stirred at r.t. for 2 hrs, then diluted with $CH_2Cl_2$ (10 mL) and washed with water (10 mL). The organic layer was dried over $Na_2SO_4$, then filtered, concentrated and purified on a silica gel column (eluted with 20% EtOAc in hexane) to provide Compound 55.

Using the procedure of Example 12, other compounds that are representative of the invention may be prepared by varying the starting materials, reagent(s) and conditions used, such as:

Compound 12h (0.045 g, 0.10 mmol) was added to a solution of 1-amino-piperidine Compound 13a (0.01 g, 0.11 mmol) in $CH_2Cl_2$ (6 mL) and TEA (0.14 mL, 0.12 mmol). The suspension was stirred at r.t. for 2 hrs, then diluted with $CH_2Cl_2$ (10 mL) and washed with water (5 mL). The organic layer was dried over $Na_2SO_4$, then concentrated and purified on a silica gel column (eluted with 20% EtOAc in hexane) to provide Compound 54 (0.03 g, 58%) as a light yellow solid. MS m/z 517 ($MH^+$).

Using the procedure of Example 13, other compounds that are representative of the invention may be prepared by varying the starting materials, reagent(s) and conditions used, such as:

| Cpd | Name | MS |
|---|---|---|
| 52 | (7Z)-1-(2,4-dichloro-phenyl)-7-(4-fluoro-benzylidene)-1,4,6,7-tetrahydro-thiopyrano[4,3-c]pyrazole-3-carboxylic acid N'-(2,4-dichloro-phenyl)-hydrazide | 595 |
| 56 | (7Z)-1-(2,4-dichloro-phenyl)-7-(4-fluoro-benzylidene)-1,4,6,7-tetrahydro-thiopyrano[4,3-c]pyrazole-3-carboxylic acid pyrrolidin-1-ylamide | 503 |
| 58 | (7Z)-1-(2,4-dichloro-phenyl)-7-(4-fluoro-benzylidene)-1,4,6,7-tetrahydro-thiopyrano[4,3-c]pyrazole-3-carboxylic acid [(1R,2S)-2-hydroxy-indan-1-yl]-amide | 566.1 |
| 59 | (7Z)-1-(2,4-dichloro-phenyl)-7-(4-fluoro-benzylidene)-1,4,6,7-tetrahydro-thiopyrano[4,3-c]pyrazole-3-carboxylic acid [(1S,2R)-2-hydroxy-indan-1-yl]-amide | 566 |
| 60 | (7Z)-1-(2,4-dichloro-phenyl)-7-(4-fluoro-benzylidene)-1,4,6,7-tetrahydro-thiopyrano[4,3-c]pyrazole-3-carboxylic acid [(1R,2R)-2-hydroxy-cyclopentyl]-amide | 518 |
| 61 | (7Z)-1-(2,4-dichloro-phenyl)-7-(4-fluoro-benzylidene)-1,4,6,7-tetrahydro-thiopyrano[4,3-c]pyrazole-3-carboxylic acid [(1R,2R)-2-hydroxy-cyclohexyl]-amide | 532 |
| 64 | 4-{[(7Z)-1-(2,4-dichloro-phenyl)-7-(4-fluoro-benzylidene)-1,4,6,7-tetrahydro-thiopyrano[4,3-c]pyrazole-3-carbonyl]-amino}-piperazine-1-carboxylic acid tert-butyl ester | 618.8 |
| 72 | (7Z)-1-(2,4-dichloro-phenyl)-7-(4-fluoro-benzylidene)-1,4,6,7-tetrahydro-thiopyrano[4,3-c]pyrazole-3-carboxylic acid (pyridin-2-ylmethyl)-amide | 525.2 |
| 88 | (7Z)-2-(2,4-dichloro-phenyl)-7-(4-fluoro-benzylidene)-2,4,6,7-tetrahydro-thiopyrano[4,3-c]pyrazole-3-carboxylic acid piperidin-1-ylamide | 517 |
| 92 | (7Z)-2-(2,4-dichloro-phenyl)-7-(4-fluoro-benzylidene)-2,4,6,7-tetrahydro-thiopyrano[4,3-c]pyrazole-3-carboxylic acid (hexahydro-cyclopenta[c]pyrrol-2-yl)-amide | 543.1 |
| 93 | (7Z)-1-(4-chloro-phenyl)-7-(4-fluoro-benzylidene)-1,4,6,7-tetrahydro-thiopyrano[4,3-c]pyrazole-3-carboxylic acid piperidin-1-ylamide | 483 |
| 102 | (7Z)-1-(4-chloro-phenyl)-7-(4-fluoro-benzylidene)-1,4,6,7-tetrahydro-thiopyrano[4,3-c]pyrazole-3-carboxylic acid pyrrolidin-1-ylamide | 469 |
| 103 | (7Z)-1-(4-chloro-phenyl)-7-(4-fluoro-benzylidene)-1,4,6,7-tetrahydro-thiopyrano[4,3-c]pyrazole-3-carboxylic acid (hexahydro-cyclopenta[c]pyrrol-2-yl)-amide | 509 |
| 111 | (7Z)-1-(2,4-dichloro-phenyl)-7-(4-fluoro-benzylidene)-1,4,6,7-tetrahydro-thiopyrano[4,3-c]pyrazole-3-carboxylic acid (2,6-dimethyl-piperidin-1-yl)-amide | 545 |
| 112 | (7Z)-1-(2,4-dichloro-phenyl)-7-(4-fluoro-benzylidene)-1,4,6,7-tetrahydro-thiopyrano[4,3-c]pyrazole-3-carboxylic acid azepan-1-ylamide | 531 |
| 113 | (7Z)-1-(2,4-dichloro-phenyl)-7-(4-fluoro-benzylidene)-1,4,6,7-tetrahydro-thiopyrano[4,3-c]pyrazole-3-carboxylic acid (4-methyl-piperazin-1-yl)-amide | 532 |
| 114 | (7Z)-1-(2,4-dichloro-phenyl)-7-(4-fluoro-benzylidene)-1,4,6,7-tetrahydro-thiopyrano[4,3-c]pyrazole-3-carboxylic acid [4-(2-hydroxy-ethyl)-piperazin-1-yl]-amide | 562 |
| 115 | (7Z)-1-(2,4-dichloro-phenyl)-7-(4-fluoro-benzylidene)-1,4,6,7-tetrahydro-thiopyrano[4,3-c]pyrazole-3-carboxylic acid N'-cyclohexyl-hydrazide | 531.1 |
| 116 | (7Z)-1-(2,4-dichloro-phenyl)-7-(4-fluoro-benzylidene)-1,4,6,7-tetrahydro-thiopyrano[4,3-c]pyrazole-3-carboxylic acid (hexahydro-cyclopenta[c]pyrrol-2-yl)-amide | 543 |
| 122 | (7Z)-1-(2,4-dichloro-phenyl)-7-(4-fluoro-benzylidene)-1,4,6,7-tetrahydro-thiopyrano[4,3-c]pyrazole-3-carboxylic acid [(2R)-2-(methoxymethyl)-pyrrolidin-1-yl]-amide | 548 |
| 123 | (7Z)-1-(2,4-dichloro-phenyl)-7-(4-fluoro-benzylidene)-1,4,6,7-tetrahydro-thiopyrano[4,3-c]pyrazole-3-carboxylic acid [(2S)-2-(methoxymethyl)-pyrrolidin-1-yl]-amide | 546.9 |
| 130 | (7Z)-(4-Bromo-benzylidene)-1-(2,4-dichloro-phenyl)-1,4,6,7-tetrahydro-thiopyrano[4,3-c]pyrazole-3-carboxylic acid piperidin-1-ylamide | 577 |

EXAMPLE 14

(7Z)-1-(2,4-dichloro-phenyl)-7-(4-fluoro-benzylidene)-1,4,6,7-tetrahydro-thiopyrano[4,3-c]pyrazole-3-carboxylic acid [(1S)-1-phenyl-ethyl]-amide (Cpd 62)

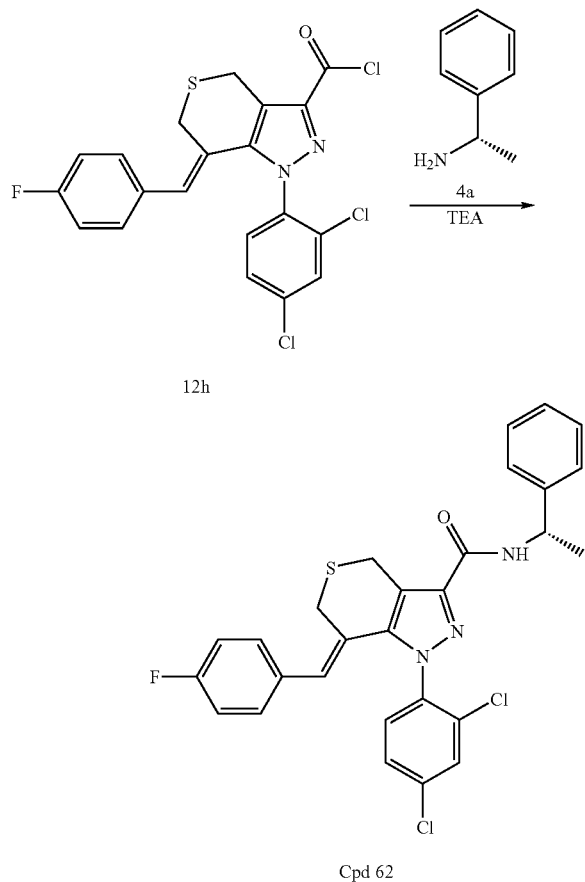

Cpd 62

Compound 12h (0.045 g, 0.1 mmol) was added to a solution of ($\alpha^1$S)-$\alpha$-methyl-benzenemethanamine Compound 4a (0.014 g, 0.12 mmol) in $CH_2Cl_2$ and TEA (0.14 mL, 0.12 mmol). The mixture was stirred at r.t. for 2 hrs, then diluted with $CH_2Cl_2$ (10 mL) and washed with water (5 mL). The organic layer was dried over $Na_2SO_4$, then concentrated and purified on a silica gel column (eluted with 15% EtOAc in hexane) to provide Compound 62 (0.04 g, 74%) as a light yellow solid. MS m/z 538 ($MH^+$).

Using the procedure of Example 14, other compounds that are representative of the invention may be prepared by varying the starting materials, reagent(s) and conditions used, such as:

| Cpd | Name | MS |
|---|---|---|
| 63 | (7Z)-1-(2,4-dichloro-phenyl)-7-(4-fluoro-benzylidene)-1,4,6,7-tetrahydro-thiopyrano[4,3-c]pyrazole-3-carboxylic acid [(1R)-1-phenyl-ethyl]-amide | 538.1 |
| 78 | (7Z)-2-(2,4-dichloro-phenyl)-7-(4-fluoro-benzylidene)-2,4,6,7-tetrahydro-thiopyrano[4,3-c]pyrazole-3-carboxylic acid [(1R)-1-phenyl-ethyl]-amide | |
| 89 | (7Z)-2-(2,4-dichloro-phenyl)-7-(4-fluoro-benzylidene)-2,4,6,7-tetrahydro-thiopyrano[4,3-c]pyrazole-3-carboxylic acid [(1R)-1-cyclohexyl-ethyl]-amide | 545.1 |
| 90 | (7Z)-2-(2,4-dichloro-phenyl)-7-(4-fluoro-benzylidene)-2,4,6,7-tetrahydro-thiopyrano[4,3-c]pyrazole-3-carboxylic acid [(1S)-1-cyclohexyl-ethyl]amide | 544.2 |
| 91 | (7Z)-2-(2,4-dichloro-phenyl)-7-(4-fluoro-benzylidene)-2,4,6,7-tetrahydro-thiopyrano[4,3-c]pyrazole-3-carboxylic acid [(1S)-1-phenyl-ethyl]-amide | 537 |
| 94 | (7Z)-1-(4-chloro-phenyl)-7-(4-fluoro-benzylidene)-1,4,6,7-tetrahydro-thiopyrano[4,3-c]pyrazole-3-carboxylic acid [(1R)-1-phenyl-ethyl]-amide | 504.1 |
| 127 | (7Z)-1-(2,4-dichloro-phenyl)-7-(4-fluoro-benzylidene)-1,4,6,7-tetrahydro-thiopyrano[4,3-c]pyrazole-3-carboxylic acid [(1R)-1-(pyridin-2-yl)-ethyl]-amide | 539.1 |
| 129 | (7Z)-(4-Bromo-benzylidene)-1-(2,4-dichloro-phenyl)-1,4,6,7-tetrahydro-thiopyrano[4,3-c]pyrazole-3-carboxylic acid [(1R)-1-phenyl-ethyl]-amide | 598 |

Using the methods and procedures from the foregoing Schemes and Examples, other compounds and their equivalents that are representative of the invention may be prepared by those skilled in the art by varying the starting materials, reagent(s) and conditions used.

Additional compounds may be made according to the synthetic methods of the present invention by one skilled in the art, differing only in possible starting materials, reagents and conditions used in the instant methods.

BIOLOGICAL EXAMPLES

The following examples illustrate that the compounds of the present invention are CB receptor modulators useful for treating, ameliorating or preventing a CB receptor mediated syndrome, disorder or disease in a subject in need thereof.

Example 1

Binding Assay for CB1 or CB2 Agonists or Inverse Agonists

The human CB-1 and CB-2 receptors were stably expressed in SK-N-MC cells transfected with pcDNA3 CB-1 (human) or pcDNA3 CB-2 (human). The cells were grown in T-180 cell culture flasks under standard cell culture conditions at 37° C. in a 5% $CO_2$ atmosphere. The cells were harvested by trypsinization and homogenized in a homogenization buffer (10 mM Tris, 0.2 mM $MgCl_2$, 5 mM KCl, with protease inhibitors aprotinin, leupeptin, pepstatin A and bacitracin) and centrifuged (2000 g). The supernatant was then centrifuged in 2M sucrose (31,300 g) to produce a semi-purified membrane pellet. The pellet was resuspended in homogenization and store at −80° C.

On the day of the assay, the pellet was thawed on ice and diluted in assay buffer (50 mM Tris-HCl, 5 mM $MgCl_2$, 2.5 mM EDTA, 0.5 mg/mL fatty acid free bovine serum albumin, pH 7.5). The diluted membrane was added with buffer, test compound or standard and the radioligand $[H]^{3+}$-CP-55,940_ (0.2 nM) to the wells of a 96-well polypropylene plate. Non-specific binding was measured in wells containing 10 uM WIN 55,212. The plate was covered and incubated for 90 minutes at 30° C. The contents were then aspirated onto a Packard Unifilter G/C filter bottom plate prewet with 0.5% polyethyleneimine. The wells of the polypropylene plate were rinsed and aspirated seven times with a 0.9% saline-0.5% Tween 20 solution. The Unifilter plate was dried, a scintillation cocktail was added to each well and the counts representing binding were quantitated in a TopCount scintillation counter.

CB1 and CB2 Receptor Binding Results

The $IC_{50}$ binding values for compounds tested were calculated by linear regression and were obtained from studies in which varying compound concentrations were used. Where an $IC_{50}$ was not obtained, test results are provided as percent inhibition at a test concentration of $^a$0.2 µM, $^b$1 µM or $^c$10 µM.

TABLE 1

CANNABINOID CB1 RECEPTOR BINDING $IC_{50}$ (µM)

| Cpd | CB1 $IC_{50}$ (µM) |
|---|---|
| 1 | 0.16 |
| 2 | $^b$13% |
| 3 | $^b$23% |
| 4 | $^b$12% |
| 5 | $^b$9% |
| 6 | $^b$16% |
| 7 | $^b$15% |
| 8 | $^b$8% |
| 9 | $^b$6% |
| 10 | $^b$0% |
| 11 | $^b$29% |
| 12 | $^b$15% |
| 13 | $^b$38% |
| 14 | $^b$0% |
| 15 | $^b$4% |
| 16 | $^b$0% |
| 17 | $^b$0% |
| 18 | $^b$0% |
| 19 | 0.005 |
| 20 | 0.022 |
| 21 | $^b$53% |
| 22 | $^b$11%, $^c$0% |
| 25 | $^c$0%, $^c$6% |
| 26 | $^c$12%, $^c$43% |
| 29 | $^c$8% |
| 32 | $^c$35% |
| 33 | $^b$35%, $^c$9% |
| 34 | $^c$11% |
| 35 | $^c$4% |
| 36 | $^b$25.5%, $^c$1% |
| 37 | $^c$11% |
| 38 | $^a$28% |
| 39 | $^a$55% |
| 40 | $^a$12% |
| 41 | $^a$9% |
| 42 | $^a$31% |
| 43 | $^a$41% |
| 44 | $^a$3% |
| 45 | $^a$33% |
| 46 | $^a$43% |
| 47 | $^a$24% |
| 48 | $^a$15% |
| 49 | $^a$33% |
| 50 | $^a$50% |
| 51 | $^a$35% |
| 52 | $^a$66% |
| 53 | $^a$55% |
| 54 | 0.034 |
| 55 | $^a$52% |
| 56 | 0.035 |
| 57 | $^a$56% |
| 58 | 0.04 |
| 59 | 0.042 |
| 60 | $^a$60% |
| 61 | $^a$60% |
| 62 | 0.048 |

TABLE 1-continued

CANNABINOID CB1 RECEPTOR BINDING $IC_{50}$ (µM)

| Cpd | CB1 $IC_{50}$ (µM) |
|---|---|
| 63 | 0.009 |
| 64 | 0.024 |
| 65 | 0.005 |
| 66 | 0.004 |
| 67 | $^a$46% |
| 68 | $^a$52% |
| 69 | 0.023 |
| 70 | 0.012 |
| 71 | $^a$18% |
| 72 | $^a$48% |
| 73 | $^a$56% |
| 74 | $^a$45% |
| 75 | 0.014 |
| 76 | $^a$20% |
| 77 | $^a$55% |
| 78 | $^a$62% |
| 79 | 0.16 |
| 80 | $^a$21% |
| 81 | 0.032 |
| 82 | 0.048 |
| 83 | 0.027 |
| 84 | 0.002 |
| 85 | 0.035 |
| 86 | 0.021 |
| 87 | 0.018 |
| 88 | $^a$46% |
| 89 | 0.074 |
| 90 | $^a$31% |
| 91 | $^a$38% |
| 92 | $^a$47% |
| 93 | 0.036 |
| 94 | 0.011 |
| 95 | 0.009 |
| 96 | $^a$43% |
| 97 | 0.068 |
| 98 | $^a$51% |
| 99 | $^a$66% |
| 100 | 0.025 |
| 101 | $^a$61% |
| 102 | $^a$76% |
| 103 | $^a$62% |
| 104 | $^a$76% |
| 105 | $^a$50% |
| 106 | $^a$32% |
| 107 | $^a$92% |
| 108 | $^a$88% |
| 109 | $^a$4% |
| 110 | $^a$13% |
| 111 | 0.014 |
| 112 | 0.01 |
| 113 | $^a$17% |
| 114 | $^a$6% |
| 115 | 0.079 |
| 116 | 0.011 |
| 117 | 0.009 |
| 118 | 0.008 |
| 119 | 0.081 |
| 120 | 0.033 |
| 121 | 0.048 |
| 122 | 0.006 |
| 123 | $^a$61% |
| 124 | 0.005 |
| 125 | 0.058 |
| 126 | $^a$55% |
| 127 | 0.007 |
| 128 | $^a$5% |
| 129 | 0.006 |
| 130 | 0.021 |

TABLE 2

Cannabinoid CB2 Receptor Binding IC$_{50}$ (μm)

| Cpd | CB2 IC$_{50}$ (μM) |
|---|---|
| 1 | 0.062 |
| 2 | [b]0% |
| 3 | [b]74% |
| 4 | [b]0% |
| 5 | [b]9% |
| 6 | [b]0% |
| 7 | [b]44% |
| 8 | [b]5% |
| 9 | [b]6% |
| 10 | [b]36% |
| 11 | [b]39% |
| 12 | [b]42% |
| 13 | [b]55% |
| 14 | [b]0% |
| 15 | [b]0% |
| 16 | [b]0% |
| 17 | [b]24% |
| 18 | [b]40% |
| 19 | 0.0007 |
| 20 | 0.005 |
| 21 | 0.056 |
| 22 | [b]0% [c]2% |
| 25 | [c]23%, [c]25%, [c]10% |
| 26 | [c]22%, [c]32% |
| 29 | [c]1%, [c]32% |
| 32 | [c]47% |
| 33 | 6.8 |
| 34 | [c]21% |
| 35 | [c]28% |
| 36 | [c]45%, [c]3% |
| 37 | [c]7% |
| 38 | [a]15% |
| 39 | [a]37% |
| 40 | [a]10% |
| 41 | [a]8% |
| 42 | [a]20% |
| 43 | [a]11% |
| 44 | [a]9% |
| 45 | [a]8% |
| 46 | [a]18% |
| 47 | [a]26% |
| 48 | [a]11% |
| 49 | [a]6% |
| 50 | [a]24% |
| 51 | [a]9% |
| 52 | [a]28% |
| 53 | [a]30% |
| 54 | [a]25% |
| 55 | [a]10% |
| 56 | [a]15% |
| 57 | [a]21% |
| 58 | [a]25% |
| 59 | [a]25% |
| 60 | [a]17% |
| 61 | [a]31% |
| 62 | [a]17% |
| 63 | [a]6% |
| 64 | [a]0% |
| 65 | [a]17% |
| 66 | [a]24% |
| 67 | [a]15% |
| 68 | [a]19% |
| 69 | [a]10% |
| 70 | [a]19% |
| 71 | [a]13% |
| 72 | [a]10% |
| 73 | [a]13% |
| 74 | [a]8% |
| 75 | [a]2% |
| 76 | [a]0% |
| 77 | [a]9% |
| 78 | [a]11% |
| 79 | [a]10% |
| 80 | [a]2% |
| 81 | [a]24% |
| 82 | [a]19% |
| 83 | [a]17% |
| 84 | [a]17% |
| 85 | [a]20% |
| 86 | [a]14% |
| 87 | [a]4% |
| 88 | 9% |
| 89 | [a]10% |
| 90 | [a]18% |
| 91 | [a]14% |
| 92 | [a]8% |
| 93 | [a]26% |
| 94 | [a]22% |
| 95 | [a]15% |
| 96 | [a]9% |
| 97 | [a]8% |
| 98 | [a]14% |
| 99 | [a]12% |
| 100 | [a]9% |
| 101 | [a]24% |
| 102 | [a]23% |
| 103 | [a]5% |
| 104 | [a]10% |
| 105 | [a]11% |
| 106 | [a]6% |
| 107 | [a]23% |
| 108 | [a]18% |
| 109 | [a]6% |
| 110 | [a]7% |
| 111 | [a]16% |
| 112 | [a]8% |
| 113 | [a]0% |
| 114 | [a]5% |
| 115 | [a]19% |
| 116 | [a]18% |
| 117 | [a]18% |
| 118 | [a]11% |
| 119 | [a]17% |
| 120 | [a]12% |
| 121 | [a]15% |
| 122 | [a]18% |
| 123 | [a]12% |
| 124 | [a]12% |
| 125 | [a]8% |
| 126 | [a]0% |
| 127 | [a]19% |
| 128 | [a]10% |
| 129 | [a]26% |
| 130 | [a]34% |

Example 2

Functional Cell-Based Assay for CB1 or CB2 Agonist and Inverse Agonist Effects on Intra-Cellular Adenylate Cyclase Activity The CB1 and CB2 receptors are G-protein coupled receptors (GPCR), which influence cell function via the Gi-protein. These receptors modulate the activity of intracellular adenylate cyclase, which in turn produces the intracellular signal messenger cyclic-AMP (cAMP).

At baseline, or during non-ligand bound conditions, these receptors are constitutively active and tonically suppress adenylate cyclase activity. The binding of an agonist causes further receptor activation and produces additional suppression of adenylate cyclase activity. The binding of an inverse agonist inhibits the constitutive activity of the receptors and results in an increase in adenylate cyclase activity.

By monitoring intracellular adenylate cyclase activity, the ability of compounds to act as agonists or inverse agonists can be determined.

Assay

Test compounds were evaluated in SK-NC cells which, using standard transfection procedures, were stably transfected with human cDNA for pcDNA3-CRE β-gal and pcDNA3 CB-1 (human) or pcDNA3 CB-2 (human). By expressing CRE β-gal, the cells produced β-galactosidase in response to CRE promoter activation by cAMP. Cells expressing CRE β-gal and either the human CB1 or CB2 receptor will produce less β-galactosidase when treated with a CB1/CB2 agonist and will produce more β-galactosidase when treated with a CB1/CB2 inverse agonist.

Cell Growth

The cells were grown in 96-well plates under standard cell culture conditions at 37° C. in a 5% $CO_2$ atmosphere. After 3 days, the media was removed and a test compound in media (wherein the media was supplemented with 2 mM L-glutamine, 1M sodium pyruvate, 0.1% low fatty acid FBS (fetal bovine serum) and antibiotics) was added to the cell. The plates were incubated for 30 minutes at 37° C. and the plate cells were then treated with forskolin over a 4-6 hour period, then washed and lysed. The β-galactosidase activity was quantitated using commercially available kit reagents (Promega Corp. Madison, Wis.) and a Vmax Plate Reader (Molecular Devices, Inc).

CB1 Receptor Mediated Change in CRE β-Gal Expression

For cells expressing CRE β-gal and the CB1 receptor, CB1 agonists reduced β-galactosidase activity in a dose-dependent manner and CB1 inverse agonists increased β-galactosidase activity in a dose-dependent manner.

The change in β-galactosidase activity was determined by setting a vehicle treated cell's activity value at 100% and expressing the β-galactosidase activity measured in a corresponding compound treated cell as a percent of the vehicle treated cell activity.

CB1 Receptor Results

The $EC_{50}$ and $IC_{50}$ values for compounds tested were calculated by linear regression and were obtained from studies in which varying compound concentrations were used.

CB1 Receptor Functional Results

The $EC_{50}$ values for compounds tested were calculated by linear regression and were obtained from studies in which varying compound concentrations were used. Where an $EC_{50}$ was not obtained, test results are provided as percent inhibition at a test concentration of 1 μM. $^a$Test value in $IC_{50}$; indicates agonist activity.

TABLE 3

CB1 RECEPTOR FUNCTIONAL $EC_{50}$ (μM)

| Cpd | CB1 $EC_{50}$ (μM) |
|---|---|
| 1 | $0.07^a$ |
| 3 | 17% |
| 13 | 7.88 |
| 19 | $0.03^a$ |
| 20 | $0.06^a$ |
| 21 | $6.3^a$ |
| 25 | 1% |
| 33 | 24% |

Example 4

Acute Treatment (Ob/Ob Mice)

The effect of acute, single-dose administration of a compound of the present invention was tested in hyperphagic obese ob/ob mice. Animals were orally administered (gavage) either test compound or vehicle. Body weight, plasma triglycerides and plasma glucose were monitored.

Animals administered a test compound had a relatively dose-dependent decrease in body weight, plasma triglycerides and plasma glucose compared to animals administered vehicle.

It is to be understood that the preceding description teaches the principles of the present invention, with examples that have emphasized certain aspects. It will also be understood that the practice of the invention encompasses all of the usual variations, adaptations and modifications as come within the scope of the following claims and their equivalents. However, numerous other equivalents not specifically elaborated on or discussed may nevertheless fall within the spirit and scope of the present invention and claims and are intended to be included.

Throughout this application, various publications are cited. The disclosure of these publications is hereby incorporated by reference into this application to describe more fully the state of the art to which this invention pertains.

What is claimed is:

1. A compound of Formula (I):

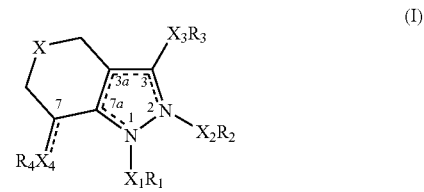

wherein
the dashed lines between positions 2-3 and positions 3a-7a in Formula (I) each represent the location for a double bond when $X_1R_1$ is present;
the dashed lines between positions 3-3a and positions 7a-1 in Formula (I) each represent the location for a double bond when $X_2R_2$ is present;
the dashed line between position 7 and $X_4R_4$ in Formula (I) represents the location for a double bond;
X is sulfur, sulfoxo or sulfonyl;
$X_1$ is absent or is lower alkylene;
$X_2$ is absent or is lower alkylene;
wherein only one of $X_1R_1$ and $X_2R_2$ are present;
$X_3$ is absent or is lower alkylene or lower alkylidene;
when the dashed line between position 7 and $X_4R_4$ is absent, then $X_4$ is absent or is lower alkylene;
when the dashed line between position 7 and $X_4R_4$ is present, then $X_4$ is absent;
$R_1$ is hydrogen, aryl, $C_3$-$C_{12}$ cycloalkyl, or heterocyclyl, wherein each of aryl, $C_3$-$C_{12}$ cycloalkyl, or heterocyclyl is optionally substituted at one or more positions by halogen, lower alkyl, hydroxy or lower alkoxy;
$R_2$ is hydrogen, aryl, $C_3$-$C_{12}$ cycloalkyl, or heterocyclyl, wherein each of aryl, $C_3$-$C_{12}$ cycloalkyl, or heterocyclyl is optionally substituted at one or more positions by halogen, lower alkyl, hydroxy or lower alkoxy;
$R_3$ is —C(O)-heterocyclyl or -Z-N($R_6$)-$Z_1R_7$ (optionally substituted on heterocyclyl by one or more hydroxy, halogen, amino, lower alkyl, carboxy, alkoxycarbonyl, lower alkoxy, lower alkoxy-lower alkylene-, hydroxyalkylene-, aryloxy or arylalkoxy);

when the dashed line between position 7 and $X_4R_4$ is absent, then $R_4$ is hydrogen, hydroxy, lower alkyl, lower alkoxy, halogen, aryl (optionally substituted on aryl at one or more positions by hydroxy, lower alkyl, lower alkoxy or halogen, heterocyclyl (optionally substituted on heterocyclyl at one or more positions by hydroxy, lower alkyl, lower alkoxy or halogen) or $C_3$-$C_{12}$ cycloalkyl (optionally substituted on $C_3$-$C_{12}$ cycloalkyl at one or more positions by hydroxy, lower alkyl, lower alkoxy or halogen);

when the dashed line between position 7 and $X_4R_4$ is present, then $R_4$ is CH-aryl (optionally substituted on aryl at one or more positions by hydroxy, lower alkyl, lower alkoxy or halogen) or CH-heterocyclyl (optionally substituted on heterocyclyl at one or more positions by hydroxy, lower alkyl, lower alkoxy or halogen);

$R_6$ and $R_7$ are each individually hydrogen, lower alkyl, —$NR_8R_9$, aryl (optionally substituted on aryl by one or more hydroxy, halogen, lower alkyl, carboxy, alkoxycarbonyl, lower alkoxy, hydroxy-alkylene-, aryloxy or arylalkoxy), $C_3$-$C_{12}$ cycloalkyl (optionally substituted on $C_3$-$C_{12}$ cycloalkyl by one or more hydroxy, halogen, amino, lower alkyl, carboxy, alkoxycarbonyl, lower alkoxy, hydroxy-alkylene-, aryloxy, arylalkoxy or lower alkylene) or heterocyclyl (optionally substituted on heterocyclyl by one or more hydroxy, halogen, amino, lower alkyl, carboxy, alkoxycarbonyl, lower alkoxy, lower alkoxy-lower alkylene-, hydroxy-alkylene-, aryloxy or arylalkoxy);

$R_8$ and $R_9$ are each individually hydrogen, alkyl, heterocyclyl, $C_3$-$C_{12}$ cycloalkyl, or aryl (optionally substituted on aryl by one or more lower alkyl, hydroxy, alkoxy, halogen, heterocyclyl or aryl-lower alkylene-);

Z is carbonyl or sulfonyl;

$Z_1$ is absent; or is lower alkylene optionally substituted at one or more positions by halogen, hydroxy, lower alkoxy, carboxy or lower alkoxycarbonyl;

or a pharmaceutically acceptable salt, stereoisomer, or prodrug thereof.

2. The compound of claim 1, wherein $X_1$ is absent or is lower alkylene and $R_1$ is hydrogen, $C_3$-$C_{12}$ cycloalkyl or aryl (optionally substituted on aryl at one or more positions by lower alkyl, lower alkoxy or halogen).

3. The compound of claim 1, wherein when the dashed line between position 7 and $X_4R_4$ is absent, then $X_4$ is absent or is lower alkylene and $R_4$ is hydrogen, hydroxy, lower alkyl, lower alkoxy, halogen, aryl (optionally substituted on aryl at one or more positions by lower alkoxy or halogen), heterocyclyl (optionally substituted on heterocyclyl at one or more positions by halogen) or $C_3$-$C_8$ cycloalkyl.

4. The compound of claim 1, wherein when the dashed line between positions 7 and $X_4R_4$ is absent then $X_4$ is absent and $R_4$ is hydrogen.

5. The compound of claim 1, wherein $X_3$ is absent or is lower alkylidene; $R_3$ is —C(O)-heterocyclyl or -Z-N($R_6$)-$Z_1R_7$ (optionally substituted on heterocyclyl by one or more hydroxy, halogen, amino, lower alkyl, carboxy, alkoxycarbonyl, lower alkoxy, lower alkoxy-lower alkylene-, hydroxy-alkylene-, aryloxy or arylalkoxy); Z is carbonyl or sulfonyl; $Z_1$ is absent or is lower alkylene; and $R_6$ and $R_7$ are each individually hydrogen, lower alkyl, —$NR_8R_9$, aryl (optionally substituted on aryl by one or more hydroxy, halogen, lower alkyl, carboxy, alkoxycarbonyl, lower alkoxy, hydroxy-alkylene-, aryloxy or arylalkoxy), $C_3$-$C_{12}$ cycloalkyl (optionally substituted on $C_3$-$C_{12}$ cycloalkyl by one or more hydroxy, halogen, amino, lower alkyl, carboxy, alkoxycarbonyl, lower alkoxy, hydroxy-alkylene-, aryloxy, arylalkoxy or heterocyclyl (optionally substituted on heterocyclyl by one or more hydroxy, halogen, amino, lower alkyl, carboxy, alkoxycarbonyl, lower alkoxy, lower alkoxy-lower alkylene-, hydroxy-alkylene-, aryloxy or arylalkoxy), wherein $R_8$ and $R_9$ are each individually hydrogen, alkyl, heterocyclyl, $C_3$-$C_{12}$ cycloalkyl or aryl (optionally substituted on aryl by one or more lower alkyl, hydroxy, alkoxy, halogen, heterocyclyl or aryl-lower alkylene-).

6. The compound of claim 1, wherein $X_3$ is absent or is lower alkylidene; $R_3$ is —C(O)-heterocyclyl or -Z-N($R_6$)-$Z_1R_7$; Z is carbonyl or sulfonyl; $Z_1$ is absent or is lower alkylene; and $R_6$ and $R_7$ are each individually hydrogen, lower alkyl, —$NR_8R_9$, aryl (optionally substituted on aryl by one or more hydroxy, halogen, lower alkyl, lower alkoxy or hydroxy-alkylene-); $C_3$-$C_{12}$ cycloalkyl (optionally substituted on $C_3$-$C_{12}$ cycloalkyl by one or more hydroxy, halogen, amino, lower alkyl, carboxy, alkoxycarbonyl, lower alkoxy or hydroxy-alkylene-) or heterocyclyl (optionally substituted on heterocyclyl by one or more hydroxy, halogen, amino, lower alkyl, carboxy, alkoxycarbonyl, lower alkoxy, lower alkoxy-lower alkylene- or hydroxy-alkylene-), wherein $R_8$ and $R_9$ are each individually hydrogen, alkyl, heterocyclyl, $C_3$-$C_{12}$ cycloalkyl or aryl (optionally substituted on aryl by one or more lower alkyl, hydroxy, alkoxy or halogen).

7. The compound of claim 1, wherein $X_3$ is absent or is lower alkylidene; $R_3$ is —C(O)-heterocyclyl or -Z-N($R_6$)-$Z_1R_7$; Z is carbonyl or sulfonyl; $Z_1$ is absent or is lower alkylene; and $R_6$ and $R_7$ are each individually hydrogen, lower alkyl, —$NR_8R_9$, aryl, $C_3$-$C_{12}$ cycloalkyl (optionally substituted on $C_3$-$C_{12}$ cycloalkyl by one or more hydroxy, lower alkyl or alkoxycarbonyl) or heterocyclyl (optionally substituted on heterocyclyl by one or more lower alkyl, alkoxycarbonyl, lower alkoxy-lower alkylene- or hydroxy-alkylene-), wherein $R_8$ and $R_9$ are each individually hydrogen, alkyl, $C_3$-$C_{12}$ cycloalkyl or aryl (optionally substituted on aryl by one or more halogen).

8. The compound of claim 1, wherein $X_2$ is absent or is lower alkylene; and, $R_2$ is $C_3$-$C_{12}$ cycloalkyl or aryl (optionally substituted on aryl at one or more positions by lower alkyl, lower alkoxy or halogen).

9. The compound of claim 1, wherein when the dashed line between position 7 and $X_4R_4$ is present, then $X_4$ is absent and $R_4$ is CH-aryl (optionally substituted on aryl at one or more positions by hydroxy, lower alkyl, lower alkoxy or halogen) or CH-heterocyclyl (optionally substituted on heterocyclyl at one or more positions by hydroxy, lower alkyl, lower alkoxy or halogen).

10. The compound of claim 1, wherein when the dashed line between position 7 and $X_4R_4$ is present, then $X_4$ is absent and $R_4$ is CH-aryl (optionally substituted on aryl at one or more positions by lower alkyl, lower alkoxy or halogen) or CH-heterocyclyl (optionally substituted on heterocyclyl at one or more positions by lower alkyl, lower alkoxy or halogen).

11. The compound of claim 1, wherein when the dashed line between position 7 and $X_4R_4$ is present, then $X_4$ is absent and $R_4$ is CH-phenyl, CH-thienyl or CH-furyl (optionally substituted on phenyl, thienyl or furyl at one or more positions by lower alkyl, lower alkoxy or halogen).

12. The compound of claim 1, wherein X is sulfur, sulfoxo or sulfonyl; $X_1$ is absent or is lower alkylene; $R_1$ is hydrogen, $C_3$-$C_{12}$ cycloalkyl or aryl (optionally substituted on aryl at one or more positions by lower alkyl, lower alkoxy or halogen); when the dashed line between positions 7 and $X_4R_4$ is absent, then X₄ is absent and R₄ is hydrogen; X₃ is absent or is lower alkylidene; R₃ is —C(O)-heterocyclyl or -Z-N(R₆)-Z₁R₇; Z is carbonyl or sulfonyl; Z₁ is absent or is lower alkylene; R₆ and R₇ are each individually hydrogen, lower alkyl, —NR₈R₉, aryl, C₃-C₁₂ cycloalkyl (optionally substituted on C₃-C₁₂ cycloalkyl by one or more hydroxy, lower alkyl or alkoxycarbonyl) or heterocyclyl (optionally substituted on heterocyclyl by one or more lower alkyl, alkoxycarbonyl, lower alkoxy-lower alkylene- or hydroxy-alkylene-), wherein R₈ and R₉ are each individually hydrogen, alkyl, C₃-C₁₂ cycloalkyl or aryl (optionally substituted on aryl by one or more halogen); X₂ is absent or is lower alkylene; R₂ is C₃-C₁₂ cycloalkyl or aryl (optionally substituted on aryl at one or more positions by lower alkyl, lower alkoxy or halogen); and, when the dashed line between position 7 and X₄R₄ is present, then X₄ is absent and R₄ is CH-phenyl, CH-thienyl or CH-furyl (optionally substituted on phenyl, thienyl or furyl at one or more positions by lower alkyl, lower alkoxy or halogen).

13. A compound of the formula:

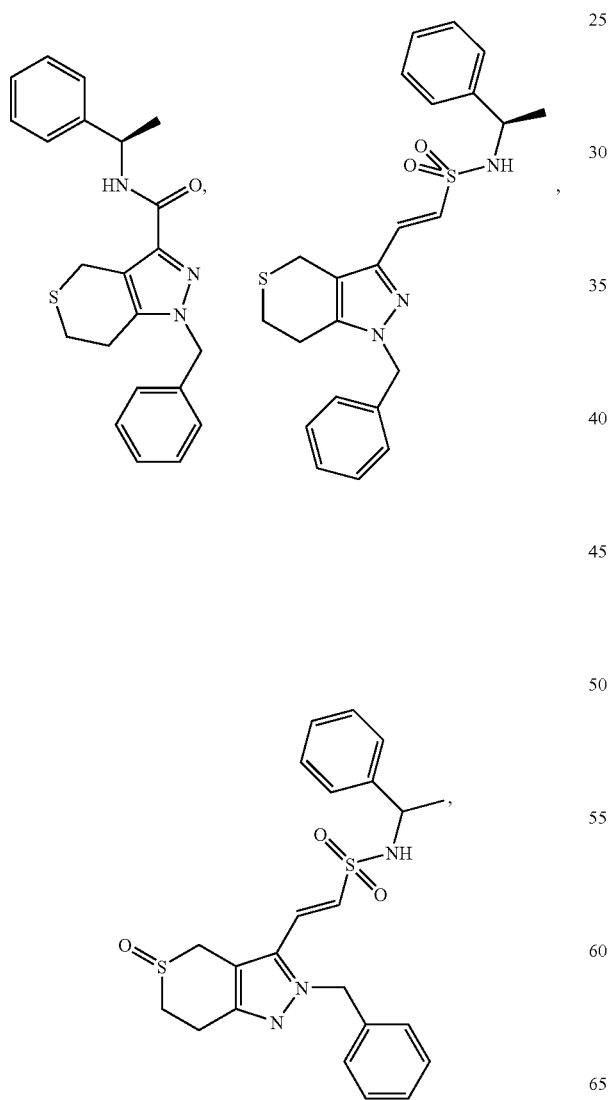

-continued

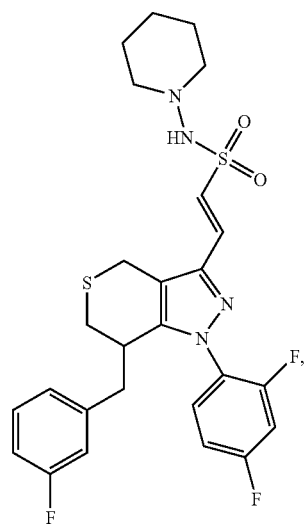

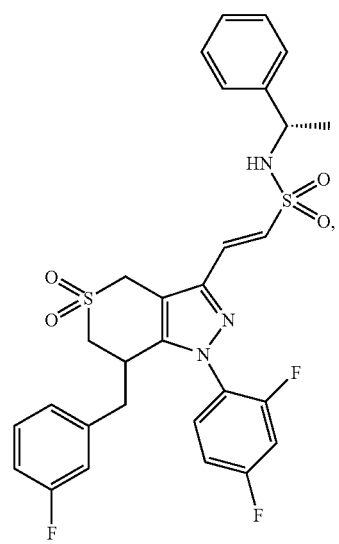

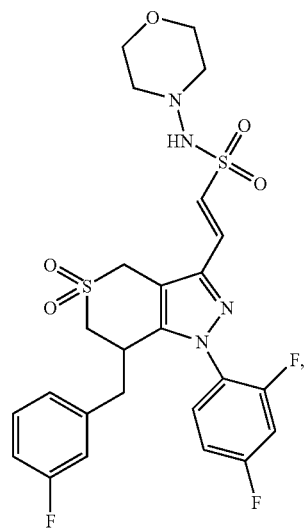

-continued
133
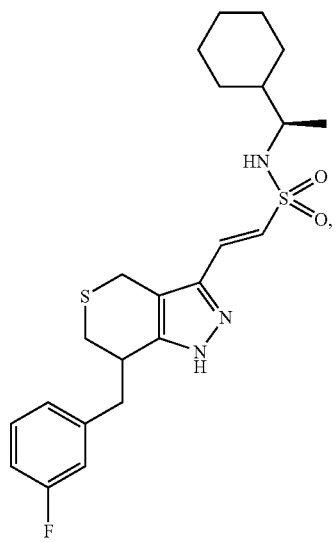
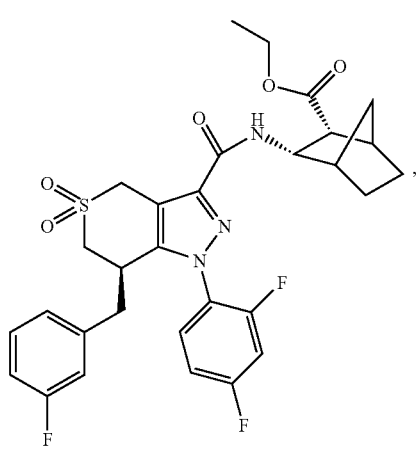
134
-continued
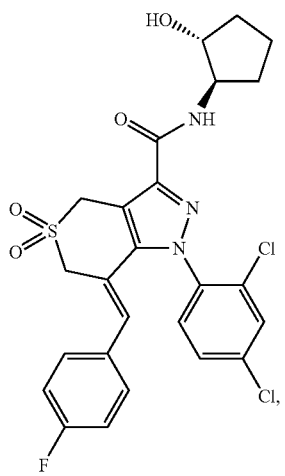
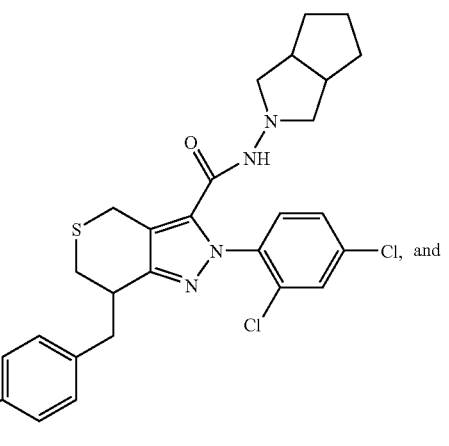

-continued

14. A compound selected from the group consisting of:
1-benzyl-1,4,6,7-tetrahydro-thiopyrano[4,3-c]pyrazole-3-carboxylic acid [(1R)-1-phenyl-ethyl]-amide,
(E)-2-(1-benzyl-1,4,6,7-tetrahydro-thiopyrano[4-3-c]pyrazol-3-yl)-ethenesulfonic acid [(1S)-1-phenyl-ethyl]-amide,
1-benzyl-5,5-dioxo-4,5,6,7-tetrahydro-1H-5$\lambda^6$-thiopyrano[4,3-c]pyrazole-3-carboxylic acid [(1R)-1-phenyl-ethyl]-amide,
1-benzyl-1,4,6,7-tetrahydro-thiopyrano[4,3-c]pyrazole-3-carboxylic acid (1,3,3-trimethyl-bicyclo[2.2.1]hept-2-yl)-amide,
1-benzyl-5,5-dioxo-4,5,6,7-tetrahydro-1H-5$\lambda^6$-thiopyrano[4,3-c]pyrazole-3-carboxylic acid (1,3,3-trimethyl-bicyclo[2.2.1]hept-2-yl)-amide,
1-benzyl-5-oxo-4,5,6,7-tetrahydro-1H-5$\lambda^4$-thiopyrano[4,3-c]pyrazole-3-carboxylic acid (1,3,3-trimethyl-bicyclo[2.2.1]hept-2-yl)-amide,
(E)-2-[1-(2,4-difluoro-phenyl)-7-(3-fluoro-benzyl)-1,4,6,7-tetrahydro-thiopyrano[4,3-c]pyrazol-3-yl]-ethenesulfonic acid [(1R)-1-cyclohexyl-ethyl]-amide,
(2R,3S)-3-{[1-(2,4-difluoro-phenyl)-(7S)-(3-fluoro-benzyl)-5,5-dioxo-4,5,6,7-tetrahydro-1H-5$\lambda^6$-thiopyrano[4,3-c]pyrazole-3-carbonyl]-amino}-bicyclo[2.2.1]heptane-2-carboxylic acid ethyl ester,
(7Z)-1-(2,4-dichloro-phenyl)-7-(4-fluoro-benzylidene)-1,4,6,7-tetrahydro-thiopyrano[4,3-c]pyrazole-3-carboxylic acid N'-(2,4-dichloro-phenyl)-hydrazide,
(7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid N'-(2,4-dichloro-phenyl)-hydrazide,
(7Z)-1-(2,4-dichloro-phenyl)-7-(4-fluoro-benzylidene)-1,4,6,7-tetrahydro-thiopyrano[4,3-c]pyrazole-3-carboxylic acid piperidin-1-ylamide,
(7Z)-[1-(2,4-dichloro-phenyl)-7-(4-fluoro-benzylidene)-1,4,6,7-tetrahydro-thiopyrano[4,3-c]pyrazol-3-yl]-piperidin-1-yl-methanone,
(7Z)-1-(2,4-dichloro-phenyl)-7-(4-fluoro-benzylidene)-1,4,6,7-tetrahydro-thiopyrano[4,3-c]pyrazole-3-carboxylic acid pyrrolidin-1-ylamide,
(7Z)-[1-(2,4-dichloro-phenyl)-7-(4-fluoro-benzylidene)-1,4,6,7-tetrahydro-thiopyrano[4,3-c]pyrazol-3-yl]-pyrrolidin-1-yl-methanone,
(7Z)-1-(2,4-dichloro-phenyl)-7-(4-fluoro-benzylidene)-1,4,6,7-tetrahydro-thiopyrano[4,3-c]pyrazole-3-carboxylic acid [(1R,2S)-2-hydroxy-indan-1-yl]-amide,
(7Z)-1-(2,4-dichloro-phenyl)-7-(4-fluoro-benzylidene)-1,4,6,7-tetrahydro-thiopyrano[4,3-c]pyrazole-3-carboxylic acid [(1S,2R)-2-hydroxy-indan-1-yl]-amide,
(7Z)-1-(2,4-dichloro-phenyl)-7-(4-fluoro-benzylidene)-1,4,6,7-tetrahydro-thiopyrano[4,3-c]pyrazole-3-carboxylic acid [(1R,2R)-2-hydroxy-cyclopentyl]-amide,
(7Z)-1-(2,4-dichloro-phenyl)-7-(4-fluoro-benzylidene)-1,4,6,7-tetrahydro-thiopyrano[4,3-c]pyrazole-3-carboxylic acid [(1R,2R)-2-hydroxy-cyclohexyl]-amide,
(7Z)-1-(2,4-dichloro-phenyl)-7-(4-fluoro-benzylidene)-1,4,6,7-tetrahydro-thiopyrano[4,3-c]pyrazole-3-carboxylic acid [(1S)-1-phenyl-ethyl]-amide,
(7Z)-1-(2,4-dichloro-phenyl)-7-(4-fluoro-benzylidene)-1,4,6,7-tetrahydro-thiopyrano[4,3-c]pyrazole-3-carboxylic acid [(1R)-1-phenyl-ethyl]-amide,
4-{[(7Z)-1-(2,4-dichloro-phenyl)-7-(4-fluoro-benzylidene)-1,4,6,7-tetrahydro-thiopyrano[4,3-c]pyrazole-3-carbonyl]-amino}-piperazine-1-carboxylic acid tert-butyl ester,
(7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1S)-1-phenyl-ethyl]-amide,
(7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1R)-1-phenyl-ethyl]-amide,
(7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1S,2S)-2-hydroxy-cyclohexyl]-amide,
(7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1R,2S)-2-hydroxy-indan-1-yl]-amide,
(7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1S,2R)-2-hydroxy-indan-1-yl]-amide,
(7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (pyridin-2-ylmethyl)-amide,
(7Z)-1-(2,4-dichloro-phenyl)-7-(4-fluoro-benzylidene)-5-oxo-4,5,6,7-tetrahydro-1H-5$\lambda^4$-thiopyrano[4,3-c]pyrazole-3-carboxylic acid [(1R)-1-phenyl-ethyl]-amide,
(7Z)-1-(2,4-dichloro-phenyl)-7-(4-fluoro-benzylidene)-5-oxo-4,5,6,7-tetrahydro-1H-5$\lambda^4$-thiopyrano[4,3-c]pyrazole-3-carboxylic acid N'-(2,4-dichloro-phenyl)-hydrazide,
(7Z)-2-(2,4-dichloro-phenyl)-7-(4-fluoro-benzylidene)-2,4,6,7-tetrahydro-thiopyrano[4,3-c]pyrazole-3-carboxylic acid [(1R)-1-phenyl-ethyl]-amide,
(7Z)-1-(2,4-dichloro-phenyl)-7-(4-fluoro-benzylidene)-5-oxo-4,5,6,7-tetrahydro-1H-5$\lambda^4$-thiopyrano[4,3-c]pyrazole-3-carboxylic acid piperidin-1-ylamide,
(7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid piperidin-1-ylamide,
(7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid [(1R)-1-phenyl-ethyl]-amide, (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid piperidin-1-ylamide, (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid [(1R)-1-cyclohexyl-ethyl]-amide, (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid [(1S)-1-cyclohexyl-ethyl]-amide, (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid [(1S)-1-phenyl-ethyl]-amide, (7Z)-2-(2,4-dichloro-phenyl)-7-(4-fluoro-benzylidene)-5,5-dioxo-4,5,6,7-tetrahydro-2H-5$\lambda^6$-thiopyrano[4,3-c]pyrazole-3-carboxylic acid (hexahydro-cyclopenta[c]pyrrol-2-yl)-amide, (7Z)-2-(2,4-dichloro-phenyl)-7-(4-fluoro-benzylidene)-2,4,6,7-tetrahydro-thiopyrano[4,3-c]pyrazole-3-carboxylic acid[(1R)-1-cyclohexyl-ethyl]-amide, (7Z)-1-(4-chloro-phenyl)-7-(4-fluoro-benzylidene)-1,4,6,7-tetrahydro-thiopyrano[4,3-c]pyrazole-3-carboxylic acid piperidin-1-ylamide, (7Z)-1-(4-chloro-phenyl)-7-(4-fluoro-benzylidene)-1,4,6,7-tetrahydro-thiopyrano[4,3-c]pyrazole-3-carboxylic acid [(1R)-1-phenyl-ethyl]-amide, (7Z)-1-(4-chloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1R)-1-phenyl-ethyl]-amide, (7Z)-1-(4-chloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (hexahydro-cyclopenta[c]pyrrol-2-yl)-amide, (7Z)-[1-(4-chloro-phenyl)-7-(4-fluoro-benzylidene)-5,5-dioxo-4,5,6,7-tetrahydro-1H-5$\lambda^6$-thiopyrano[4,3-c]pyrazol-3-yl]-piperidin-1-yl-methanone, (7Z)-1-(4-chloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid piperidin-1-ylamide, (7Z)-1-(4-chloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid N'-methyl-N'-phenyl-hydrazide, (7Z)-[1-(2,4-dichloro-phenyl)-7-(4-fluoro-benzylidene)-5,5-dioxo-4,5,6,7-tetrahydro-1H-5$\lambda^6$-thiopyrano[4,3-c]pyrazol-3-yl]-piperidin-1-yl-methanone, (7Z)-1-(4-chloro-phenyl)-7-(4-fluoro-benzylidene)-1,4,6,7-tetrahydro-thiopyrano[4,3-c]pyrazole-3-carboxylic acid pyrrolidin-1-ylamide, (7Z)-1-(4-chloro-phenyl)-7-(4-fluoro-benzylidene)-1,4,6,7-tetrahydro-thiopyrano[4,3-c]pyrazole-3-carboxylic acid (hexahydro-cyclopenta[c]pyrrol-2-yl)-amide, (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (hexahydro-cyclopenta[c]pyrrol-2-yl)-amide, (7Z)-1-(2,4-difluoro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (hexahydro-cyclopenta[c]pyrrol-2-yl)-amide, (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid azepan-1-ylamide, (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid (2,6-dimethyl-piperidin-1-yl)-amide, (7Z)-1-(2,4-dichloro-phenyl)-7-(4-fluoro-benzylidene)-1,4,6,7-tetrahydro-thiopyrano[4,3-c]pyrazole-3-carboxylic acid (2,6-dimethyl-piperidin-1-yl)-amide, (7Z)-1-(2,4-dichloro-phenyl)-7-(4-fluoro-benzylidene)-1,4,6,7-tetrahydro-thiopyrano[4,3-c]pyrazole-3-carboxylic acid azepan-1-ylamide, (7Z)-1-(2,4-dichloro-phenyl)-7-(4-fluoro-benzylidene)-1,4,6,7-tetrahydro-thiopyrano[4,3-c]pyrazole-3-carboxylic acid N'-cyclohexyl-hydrazide, (7Z)-1-(2,4-dichloro-phenyl)-7-(4-fluoro-benzylidene)-1,4,6,7-tetrahydro-thiopyrano[4,3-c]pyrazole-3-carboxylic acid (hexahydro-cyclopenta[c]pyrrol-2-yl)-amide, (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid [(1R)-1-phenyl-ethyl]-amide, (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid [(1R)-1-cyclohexyl -ethyl]-amide, (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid piperidin-1-ylamide, (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid azepan-1-ylamide, (7Z)-7-(5-chloro-furan-2-ylmethylene)-1-(2,4-dichloro-phenyl)-5,5-dioxo-4,5,6,7-tetrahydro-1H-5$\lambda^6$-thiopyrano[4,3-c]pyrazole-3-carboxylic acid (hexahydro-cyclopenta[c]pyrrol-2-yl)-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(2R)-2-(methoxymethyl)-pyrrolidin-1-yl]-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(2S)-2-(methoxymethyl)-pyrrolidin-1-yl]-amide, (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(1R)-1-(pyridin-2-yl)-ethyl]-amide, (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(2S)-2-(methoxymethyl)-pyrrolidin-1-yl]-amide, (7Z)-1-(2,4-dichloro-phenyl)-7-(4-fluoro-benzylidene)-5,5-dioxo-4,5,6,7-tetrahydro-1H-5$\lambda^6$-thiopyrano[4,3-c]pyrazole-3-carboxylic acid [(2R)-2-(methoxymethyl)-pyrrolidin-1-yl]-amide, (7Z)-1-(2,4-dichloro-phenyl)-7-(4-fluoro-benzylidene)-1,4,6,7-tetrahydro-thiopyrano[4,3-c]pyrazole-3-carboxylic acid [(1R)-1-(pyridin-2-yl)-ethyl]-amide, (7Z)-(4-Bromo-benzylidene)-1-(2,4-dichloro-phenyl)-1,4,6,7-tetrahydro-thiopyrano[4,3-c]pyrazole-3-carboxylic acid [(1R)-1-phenyl-ethyl]-amide, and (7Z)-(4-Bromo-benzylidene)-1-(2,4-dichloro-phenyl)-1,4,6,7-tetrahydro-thiopyrano[4,3-c]pyrazole-3-carboxylic acid piperidin-1-ylamide.

\* \* \* \* \*